United States Patent
Tcherkassov et al.

(10) Patent No.: US 12,017,975 B2
(45) Date of Patent: Jun. 25, 2024

(54) Myc-Max INHIBITOR COMPOUND THERAPEUTICS FOR CANCER TREATMENT, METHODS AND USES ASSOCIATED THEREWITH

(71) Applicant: THE UNIVERSITY OF BRITISH COLUMBIA, Vancouver (CA)

(72) Inventors: Artem Tcherkassov, Vancouver (CA); Paul S. Rennie, Richmond (CA); Fuqiang Ban, Markham (CA); Eric J. J. Leblanc, Vancouver (CA); Lavinia A. Carabet, Burnaby (CA); Nada Lallous, Vancouver (CA); Kriti Singh, Vancouver (CA); Helene Morin, Vancouver (CA); Anh-Tien Ton, Vancouver (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 0 days.

(21) Appl. No.: 17/966,227

(22) Filed: Oct. 14, 2022

(65) Prior Publication Data

US 2023/0134821 A1    May 4, 2023

Related U.S. Application Data

(63) Continuation of application No. 17/250,810, filed as application No. PCT/CA2019/051243 on Sep. 5, 2019, now abandoned.

(Continued)

(51) Int. Cl.
| | |
|---|---|
| C07C 237/22 | (2006.01) |
| C07C 255/66 | (2006.01) |
| C07C 275/30 | (2006.01) |
| C07C 311/18 | (2006.01) |
| C07C 335/16 | (2006.01) |
| C07C 335/18 | (2006.01) |
| C07D 211/42 | (2006.01) |
| C07D 213/40 | (2006.01) |
| C07D 213/61 | (2006.01) |
| C07D 231/14 | (2006.01) |
| C07D 239/42 | (2006.01) |
| C07D 241/24 | (2006.01) |
| C07D 249/08 | (2006.01) |
| C07D 261/08 | (2006.01) |
| C07D 265/30 | (2006.01) |
| C07D 265/36 | (2006.01) |
| C07D 277/36 | (2006.01) |
| C07D 307/14 | (2006.01) |
| C07D 311/16 | (2006.01) |
| C07D 333/20 | (2006.01) |
| C07D 403/06 | (2006.01) |

(Continued)

(52) U.S. Cl.
CPC .......... *C07C 237/22* (2013.01); *C07C 255/66* (2013.01); *C07C 275/30* (2013.01); *C07C 311/18* (2013.01); *C07C 335/16* (2013.01); *C07C 335/18* (2013.01); *C07D 211/42* (2013.01); *C07D 213/40* (2013.01); *C07D 213/61* (2013.01); *C07D 231/14* (2013.01); *C07D 239/42* (2013.01); *C07D 241/24* (2013.01); *C07D 249/08* (2013.01); *C07D 261/08* (2013.01); *C07D 265/30* (2013.01); *C07D 265/36* (2013.01); *C07D 277/36* (2013.01); *C07D 307/14* (2013.01); *C07D 311/16* (2013.01); *C07D 333/20* (2013.01); *C07D 403/06* (2013.01); *C07D 403/12* (2013.01); *C07D 405/12* (2013.01); *C07D 409/06* (2013.01); *C07D 413/12* (2013.01); *C07D 417/06* (2013.01); *C07D 417/12* (2013.01); *C07D 471/04* (2013.01)

(58) Field of Classification Search
CPC ..................................................... C07C 237/22
See application file for complete search history.

(56) References Cited

U.S. PATENT DOCUMENTS 6,077,869 A    6/2000   Sui et al.

FOREIGN PATENT DOCUMENTS

WO    2007076055 A2    7/2007

OTHER PUBLICATIONS

Damia "Contemporary pre-clinical development of anticancer agents—What are the optimal preclinical models?" European Journal of Cancer 2009, 45, 2768-2781.*

(Continued)

*Primary Examiner* — David K O'Dell
(74) *Attorney, Agent, or Firm* — SALIWANCHIK, LLOYD & EISENSCHENK

(57) ABSTRACT

Provided herein are Myc-Max inhibitory compounds having the structure of Formula (I) and compositions thereof for use in the treatment of cancer. In particular, the Myc-Max inhibitory compounds may be useful for the treatment of cancers selected from one or more of: prostate cancer, breast cancer, colon cancer, cervical cancer, small-cell lung carcinomas, neuroblastomas, osteosarcomas, glioblastomas, melanoma and myeloid leukaemia.

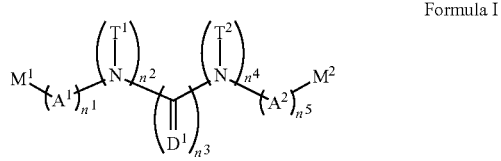

Formula I

12 Claims, 3 Drawing Sheets

Related U.S. Application Data

(60) Provisional application No. 62/727,071, filed on Sep. 5, 2018.

(51) Int. Cl.

| | |
|---|---|
| C07D 403/12 | (2006.01) |
| C07D 405/12 | (2006.01) |
| C07D 409/06 | (2006.01) |
| C07D 413/12 | (2006.01) |
| C07D 417/06 | (2006.01) |
| C07D 417/12 | (2006.01) |
| C07D 471/04 | (2006.01) |

(56) References Cited

OTHER PUBLICATIONS

Karadkhelkar Demystifying the Druggability of the MYC Family of Oncogenes Nishant M. J. Am. Chem. Soc. 2023, 145, 3259-3269.*
Llombart "Therapeutic targeting of "undruggable" MYC" eBioMedicine 2022;75: 103756.*
Tanimori "Copper-catalyzed synthesis of substituted indazoles from 2-chloroarenes at low catalyst-loading" Org. Biomol. Chem., 2012, 10, 1381.*
Bai Discovery of novel selective inhibitors for EGFR-T790M/L858R. Fang; Liu, Hongyan; Bioorganic & Medicinal Chemistry Letters, 2012, 22(3), 1365-1370.*
Cushman "Synthesis and Evaluation of Stilbene and Dihydrostilbene Derivatives as Potential Anticancer Agents That Inhibit Tubulin Polymerization" J. Med. Chem. 1991, 34, 2579-2588.*
Axerio-Cilies, P. et al. "Inhibitors of androgen receptor activation fuction-2 (AF2) site identified through virtual screening" J. Medicinal Chemistry, 2011, 54:6197-6205.
Ban, F. et al. "Discovery of 1H-indole-2-carboxamides as novel inhibitors of the androgen receptor binding function 3 (BF3)" J. Medicinal Chemistry, 2014, 57:6867-6872.
Ban, F. et al. "Best practices of computer-aided drug discovery: Lessons learned from the development of a preclinical candidate for prostate cancer with a new mechanism of action" J. Chem. Inf. Model., 2017, 57:1018-1028.
Cherkasov, A. et al. "QSAR modeling: Where have you been? Where are you going to?" J. Medicinal Chemistry, 2014, 57(12):4977-5010.
Clausen, D.M. et al. "In vitro cytotoxicity and in vivo efficacy, pharmacokinetics, and metabolism of 10074-G5, a novel small-molecule inhibitor of c-Myc/Max dimerization" J. Pharmacol. Exp. Ther., 2010, 335(3):715-727.
Dalal, K. et al. "Selectively targeting the DNA-binding domain of the androgen receptor as a prospective therapy for prostate cancer" J. Biological Chemistry, 2014, 289(38):26417-26429.
Follis, A.V. et al. "Structural rationale for the coupled binding and unfolding of the c-Myc oncoprotein by small molecules" Chem. Biol., 2008, 15:1149-1155.
Guo, J. et al. "Efficacy, pharmacokinetics, tissue distribution, and metabolism of the Myc-Max disruptor, 10058-F4 [Z,E]-5-[4-ethylbenzylidine]-2-thioxothiazolidin-4-one, in mice" Cancer Chemotherapy and Pharmacology, 2009, 63(4):615-625.
Hammoudeh, D.I. et al. "Multiple independent binding sites for small-molecule inhibitors on the oncoprotein c-Myc" J. American Chemical Society, 2009, 131:7390-7401.
Hart, J.R. et al. "Inhibitor of MYC identified in a Krohnke pyridine library" Proc. Natl Acad. Sci., 2014, 111(34):12556-12561.
Koh, C.M. et al. "Targeting MYC in cancer therapy: RNA processing offers new opportunities" Bioessays, 2016, 38:266-275.
Lack, N.A. et al. "Targeting the binding function 3 (BF3) site of the human androgen receptor through virtual screening" J. Medicinal Chemistry, 2011, 54(24):8563-8573.
Lallous, N. et al. "Targeting alternative sites on the androgen receptor to treat castration-resistant prostate cancer" Int. J. Molecular Sciences, 2013, 14:12496-12519.
Li, H. et al. "Characterization of a new class of androgen receptor antagonists with potential therapeutic applications in advanced prostate cancer" Mol. Cancer Ther., 2013, 12(11):2425-2435.
Li, H. et al. "Discovery of small-molecule inhibitors selectively targeting the DNA-binding domain of the human androgen receptor" J. Medicinal Chemistry, 2014, 57:6458-6467.
McKeown, M.R. and Bradner, J.E. "Therapeutic strategies to inhibit MYC" Cold Spring Harbor Perspectives in Medicine, 2014, 4:a014266 (16 pages).
Munuganti, R.S.N. et al. "Identification of a potent antiandrogen that targets the BF3 site of the androgen receptor and inhibits enzalutamide-resistant prostate cancer" Chem. Biol., 2014, 21:1476-1485.
Munuganti, R.S.N. et al. "Targeting the binding function 3 (BF3) site of the androgen receptor through virtual screening. 2. Development of 2-((2-phenoxyethyl) thio)-1H-benzimidazole derivatives" J. Medicinal Chemistry, 2013, 56:1136-1148.
Paul, N. et al. "Cheminformatics modeling of adverse drug responses by clinically relevant mutants of human androgen receptor" J. Chem. Inf. Model., 2016, 56:2507-2516.
Rickman, D.S. et al. "The expanding world of N-MYC-driven tumors" Cancer Discov., 2018, 8(2):150-163.
Screening Compounds, Online: "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Apr. 1, 2015.
Siddique, M.U.M. et al. "Biphenyl urea derivatives as selective CYP1B1 inhibitors" Org. Biomol. Chem., 2016, 14:8931-8936.
Stellas, D. et al. "Therapeutic effects of an anti-Myc drug on mouse pancreatic cancer" J. Natl. Cancer Inst., 2014, 106(12):1-8.
Wang, H. et al. "Improved low molecular weight Myc-Max inhibitors" Mol. Cancer Ther., 2007, 6(9):2399-2408.
Whitfield, J.R. et al. "Strategies to inhibit Myc and their clinical applicability" Front. Cell Dev. Biol., 2017, 5:10 (13 pages).
Wood, T.E. et al. "A novel inhibitor of glucose uptake sensitizes cells to FAS-induced cell death" Mol. Cancer Ther., 2008, 7(11):3546-3555.
Yap, J.L. et al. "Pharmacophore identification of c-Myc inhibitor 10074-G5" Bioorg. Med. Chem. Lett., 2013, 23(1):370-374.
Yin, X. et al. "Low molecular weight inhibitors of Myc-Max interaction and function" Oncogene, 2003, 22:6151-6159.
ZINC Chemical Database entry for N'-[4-cyano-2-(trifluoromethyl)phenyl]-4-(trifluoromethyl)benzohydrazide, ZINC799750908 Entered: Nov. 15, 2017; For-Sale Nov. 15, 2017, Online "https://zinc15.docking.org/substances/ZINC000799750908/" accessed Jul. 7, 2022.

* cited by examiner

FIGURE 2A
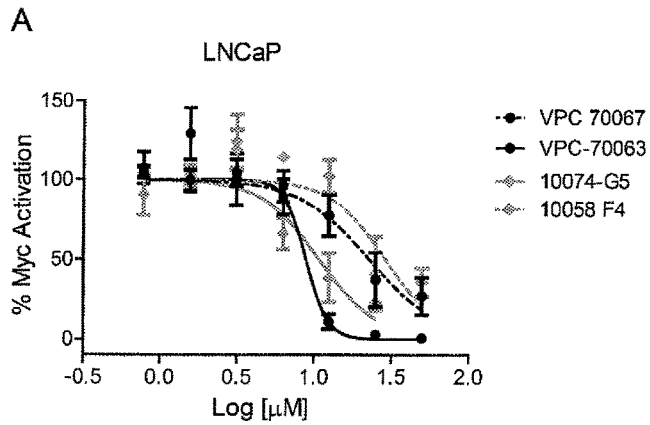
FIGURE 2B
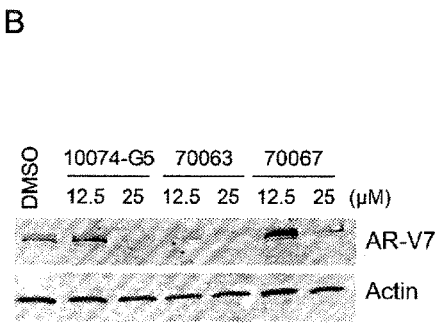
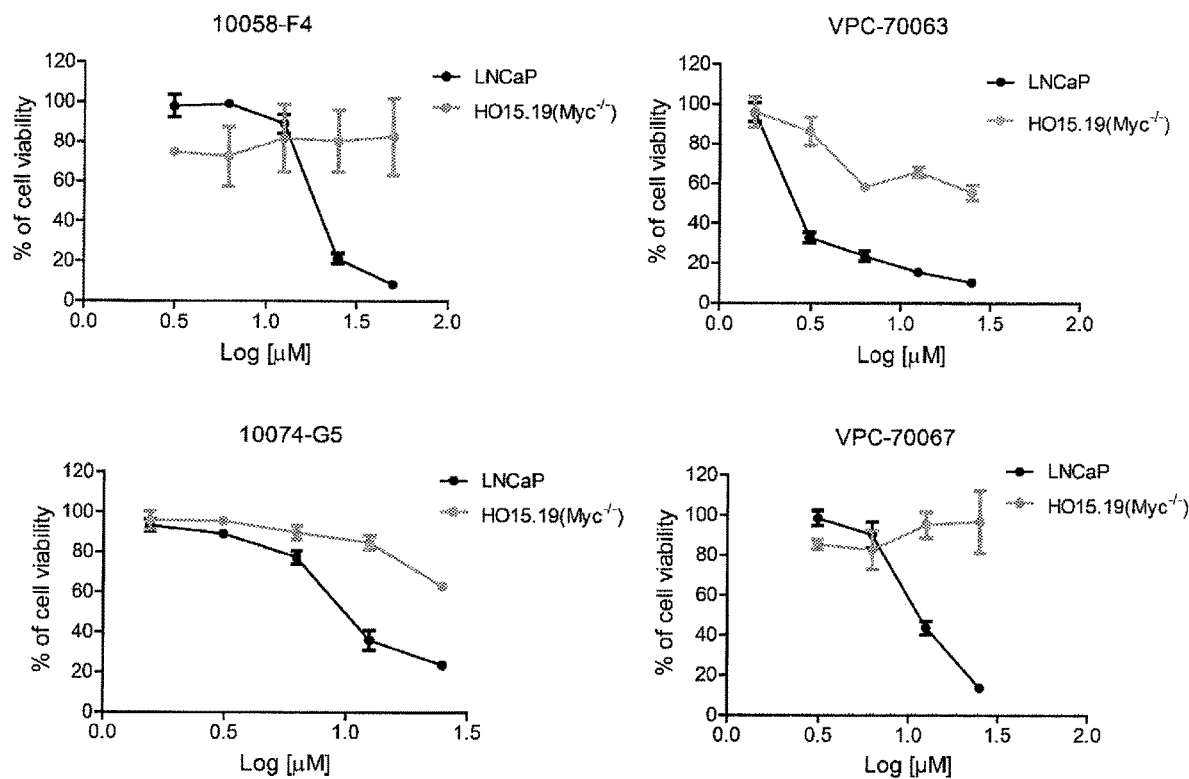
FIGURE 2C

FIGURE 3A
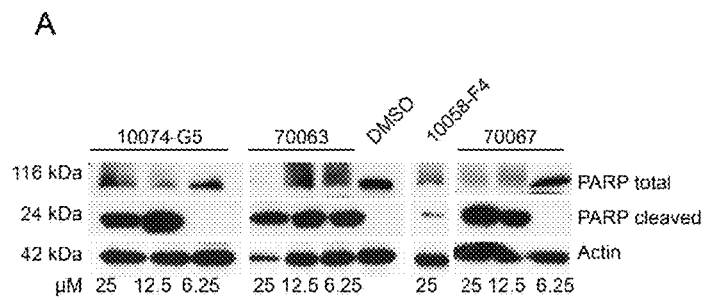
FIGURE 3B
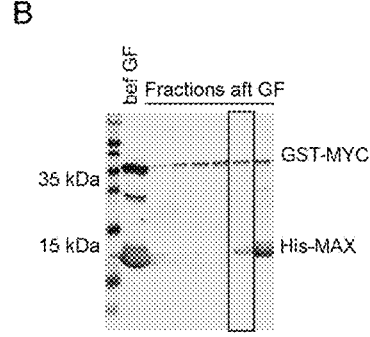
FIGURE 3C
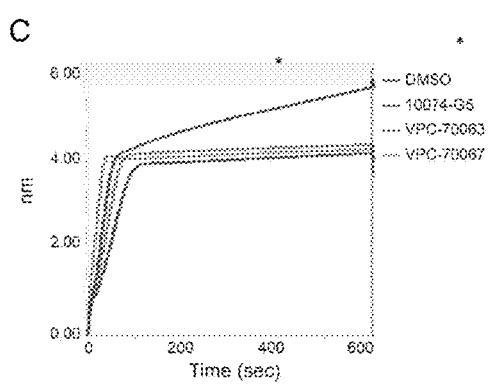
FIGURE 3D
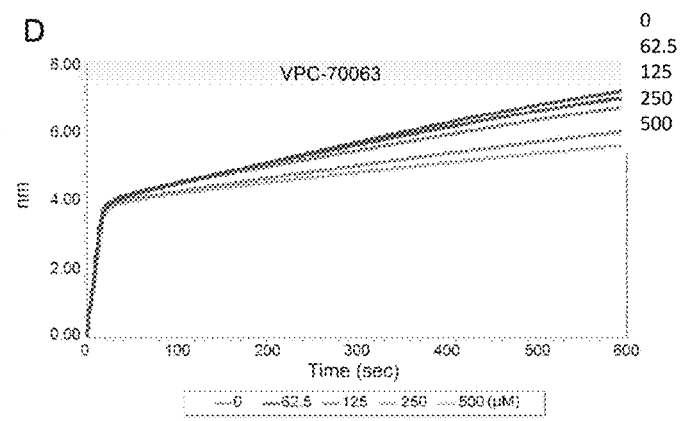
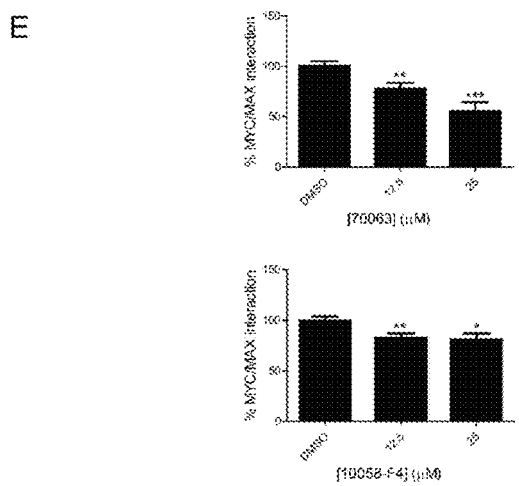
FIGURE 3E

Myc-Max INHIBITOR COMPOUND THERAPEUTICS FOR CANCER TREATMENT, METHODS AND USES ASSOCIATED THEREWITH

CROSS-REFERENCE TO RELATED APPLICATIONS

This application is a continuation application of U.S. application Ser. No. 17/250,810, filed Mar. 5, 2021; which is a National phase application corresponding to International Application No. PCT/CA2019/051243, filed Sep. 5, 2019, which claims the benefit of U.S. Provisional Application Ser. No. 62/727,071, filed Sep. 5, 2018, each of which is hereby incorporated by reference herein in its entirety.

TECHNICAL FIELD

The present invention relates to the field of Myc-Max inhibitors. In particular, the invention relates to Myc-Max inhibitor compounds for use in the treatment of cancer.

BACKGROUND

Myc is a transcription factor that regulates growth in normal cells, but in many cancers over-activity of Myc results in high rates of growth needed for tumor proliferation and progression [1, 2]. Myc drives tumorigenesis by transcriptional programming of a large number of target genes that promote cell growth, proliferation, metabolism and apoptosis, and block differentiation [3-7]. Myc is estimated to contribute to most if not all human cancers, including prostate, breast, colon, cervical cancers, small-cell lung carcinomas, neuroblastomas, osteosarcomas, glioblastomas, melanoma, and myeloid leukaemia, most of which are aggressive and respond poorly to the current therapies [1, 8, 9].

In prostate cancer (PCa), which is the second leading cause of cancer-related death in men, the Myc family members—L-Myc, c-Myc and N-Myc—are implicated in pathogenesis and progression across the full spectrum of PCa, from localized adenocarcinoma to the most advanced and treatment-resistant subtypes—castration-resistant (CRPC) and its neuroendocrine phenotype (NEPC). Amplifications of Myc family members are the most frequently observed genomic alterations associated with specific clinical stages and subtypes of PCa [10-16]. L-Myc is amplified in ~27% of localized PCa, in a mutually exclusive manner to c-Myc [11], whereas c-Myc is commonly amplified in all PCa stages and subtypes [17]. Notably, c-Myc overexpression antagonizes the transcriptional activity of the androgen receptor (AR), which is a driving force in PCa and constitutes the main drug target for advanced cases of disease [18]. Besides influencing clinically relevant AR target genes, c-Myc upregulation also affects critical splicing programs [19] and increases levels of AR-V7—the constitutively active ligand-independent AR splice variant that promotes CRPC [20, 21] and is also observed in NEPC [14]. Importantly, N-Myc amplifications induce the NEPC phenotype [14, 15, 22].

To elicit its oncogenic effects, Myc must form a heterodimer with its obligate partner Max, which together bind to the DNA and activate transcription of the target genes [23-26]. Although Myc could qualify as an ideal cancer target, applying conventional structure-based drug design approaches is inherently challenging in drugging Myc. Myc and Max are intrinsically disordered proteins (IDP), which exist as dynamic ensembles, with no effective pockets on their surfaces [27-29]. The disordered basic-helix-loop-helix-leucine zipper (bHLHLZ) domain of the Myc monomer forms DNA-binding functionalities only via association with the homologous bHLHLZ domain of Max [23, 30]. Only upon such heterodimerization does the resulting Myc-Max complex adopt a stable helical configuration which can bind specific DNA recognition sequences 5'-CACGTG-3', termed E-boxes, at enhancers and promoters of target genes, and thereby trigger the recruitment of chromatin-remodeling complexes and assembly of the transcriptional machinery to drive the transcriptional program [31, 32]. Myc and Max oligomerize through their helix-loop-helix (HLH) and leucine zipper (LZ) regions and bind DNA mainly through highly positively charged basic (b) region and specific residues located in the HLH region [33, 34].

Although Myc inactivation may have undesired effects on normal cells, experimental mouse models of KRAS-driven lung cancer carrying a conditionally inducible Omomyc construct—a Myc dominant negative, 93 residue bHLHZ protein fragment with 4 single-point mutations in the LZ region—established that periodic inhibition is effective at stopping cancer growth with mild and tolerable side effects, suggesting a viable therapeutic strategy [35, 36].

Small molecule inhibition of Myc, a therapeutically compelling oncogenic transcription factor, has been a challenge for a long time. Current strategies that directly target Myc in cancer include inhibitors of Myc-Max protein-protein interactions, such as 10058-F4, 10074-G5, and JY-3-094 [37, 38], or protein-DNA interactions, such as Mycro3 [39] and KJ-Pyr-9 [40], and inhibitors of Myc expression with G-quadruplex stabilizers, antisense oligonucleotides, and siRNA [41, 42]. Indirect approaches have been reviewed elsewhere [41, 43, 44].

Compounds 10058-F4, 10074-A4, and 10074-G5 are among the first identified direct small molecules Myc inhibitors that bind with mid-micromolar range affinity at 3 independent sites on the disordered bHLHLZ domain of the Myc (c- and N-Myc) monomer (as validated by mutagenesis and NMR experiments) [37, 45, 46]. The efforts to identify them relied on functional screening of finite libraries unlikely to contain clinically-optimized structures. Attempts to find more potent and selective analogs have yet to succeed given the inconsistent behavior of compounds in in vitro assays [47, 48]. Moreover, these compounds lack proper antitumor activity in vivo due to rapid metabolism to inactive metabolites, resulting in low tumoral concentrations insufficient to inhibit Myc-Max dimerization [49, 50]. Thus, further more effective small molecule inhibitors of Myc-Max are needed.

SUMMARY

The present invention is based in part, on the surprising discovery that the compounds described herein modulate Myc-Max activity. Specifically, some compounds identified herein, also show inhibition of Myc-Max in prostate cancer cells.

In accordance with one embodiment, there is provided a compound, the compound having the structure of Formula I:

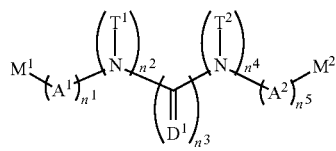

Formula I wherein, M¹ may be selected from:
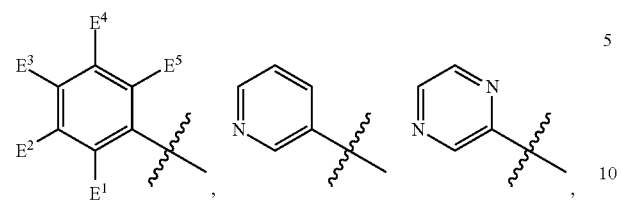
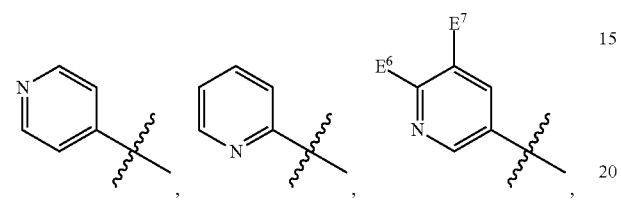
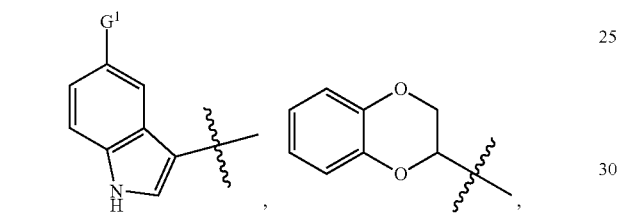
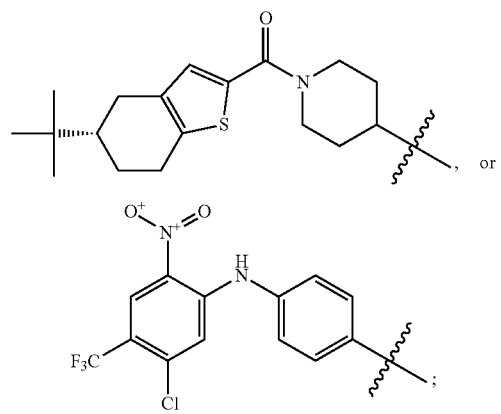, or
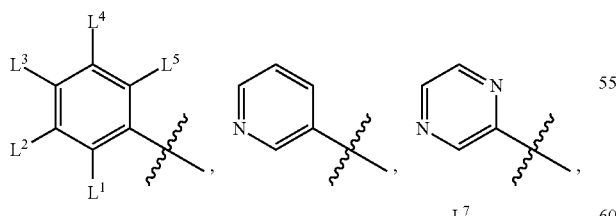
M² may be selected from:
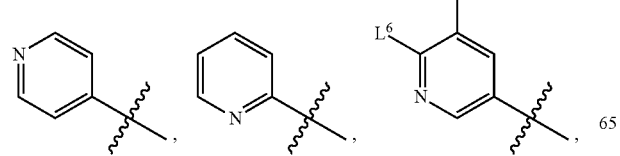
-continued
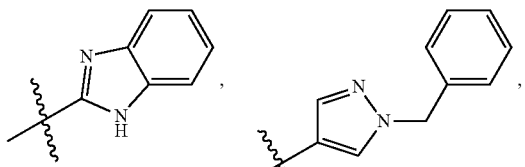
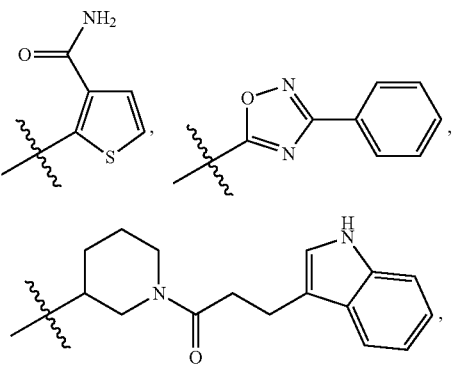
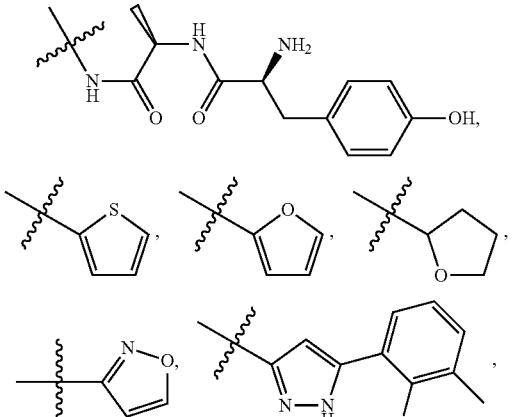
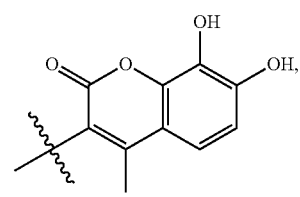
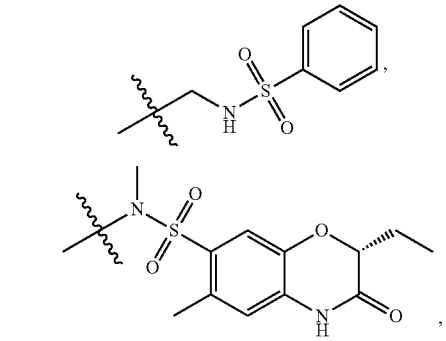
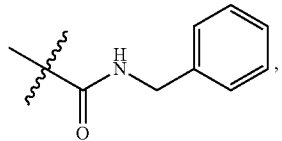

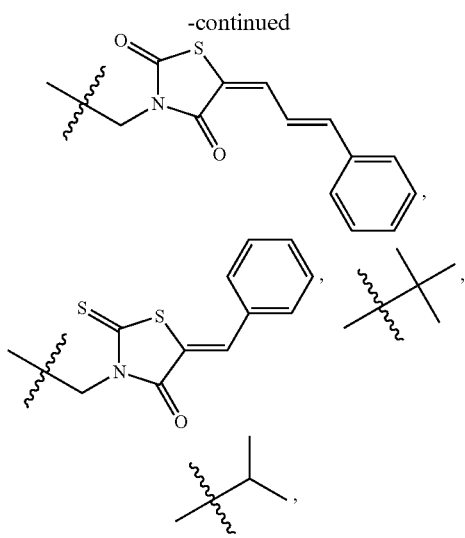

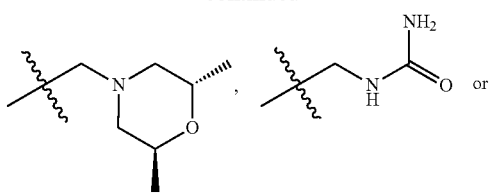

CH₃ or NH₂;
A¹ may be selected from CH₂, CH(CH₃), CH(CH₂CH₃), CH(CH(CH₃)₂), or CHX; A² may be CH₂ or CH(CH₃); T¹ may be H or CH₃; T² may be H or CH₃; D¹ may be O or S; n¹ may be 0-3, wherein if n¹ may be 2 or 3, each A¹ may be independently selected from CH₂, CH(CH₃), CH(CH₂CH₃), CH(CH(CH₃)₂), or CHX; n² may be 0-1; n³ may be 1 or 2, wherein if n³ may be 2, each D¹ may be independently selected from O or S; n⁴ may be 0-3, wherein if n⁴ may be 2 or 3, each T² may be independently selected from H or CH₃; n⁵ may be 0-3, wherein if n⁵ may be 2 or 3, each A² may be independently selected from CH₂, CH(CH₃), CH(CH₂CH₃), CH(CH(CH₃)₂), or CHX;
X may be

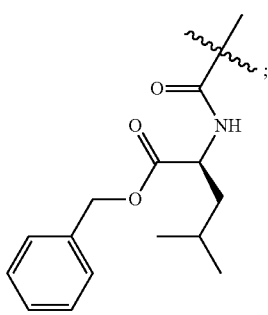 [SMILES: *C(=O)N[C@@H](CC(C)C)C(=O)OCc1ccccc1]

E¹ may be H, CH₃, CH₂CH₃, F, Cl, Br, CF₃, OCF₃, OCF₂, S(=O)₂(NH₂), OCH₂C(CH₃)(CH₂),

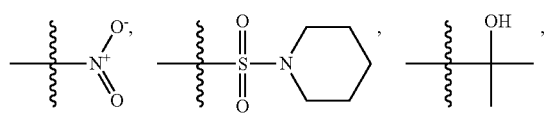

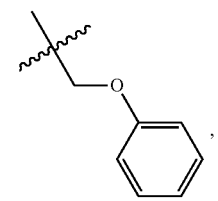

E² may be H, CH₃, CH₂CH₃, F, Cl, Br, CF₃, OCF₃, OCF₂, S(=O)₂(NH₂), OCH₂C(CH₃)(CH₂),

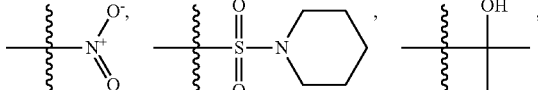

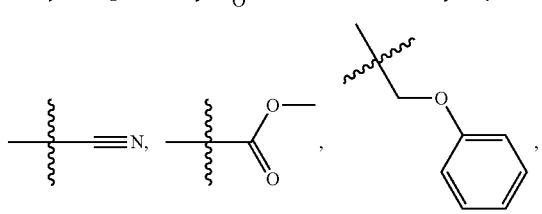

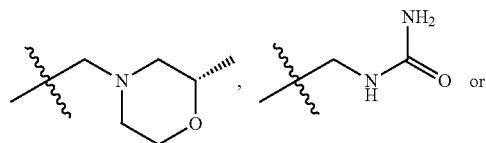

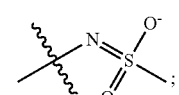

E³ may be H, CH₃, CH₂CH₃, F, Cl, Br, CF₃, OCF₃, OCF₂, S(=O)₂(NH₂), OCH₂C(CH₃)(CH₂),

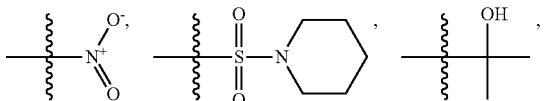

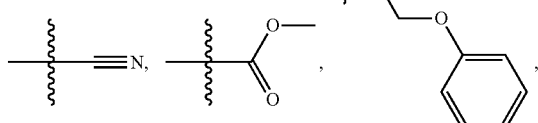

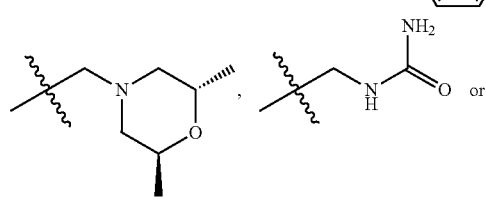

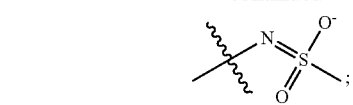

$E^4$ may be H, $CH_3$, $CH_2CH_3$, F, Cl, Br, $CF_3$, $OCF_3$, $OCF_2$, $S(=O)_2(NH_2)$, $OCH_2C(CH_3)(CH_2)$,

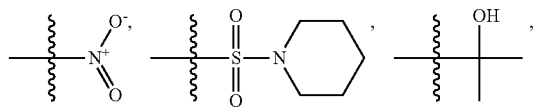

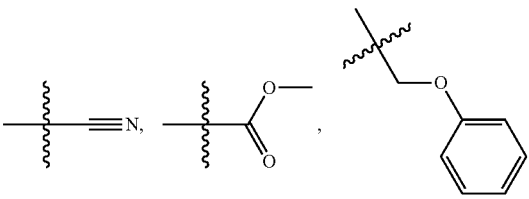

$E^5$ may be H, $CH_3$, $CH_2CH_3$, F, Cl, Br, $CF_3$, $OCF_3$, $OCF_2$, $S(=O)_2(NH_2)$, $OCH_2C(CH_3)(CH_2)$,

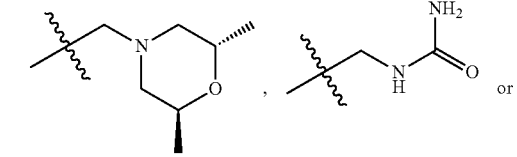

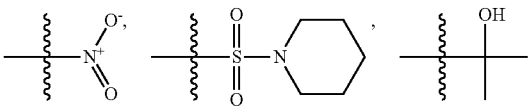

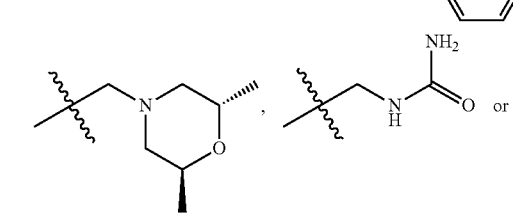

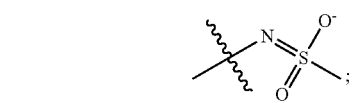

$E^6$ may be H, $CH_3$, $CH_2CH_3$, F, Cl, Br, $CF_3$, $OCF_3$, $OCF_2$, $S(=O)_2(NH_2)$, $OCH_2C(CH_3)(CH_2)$,

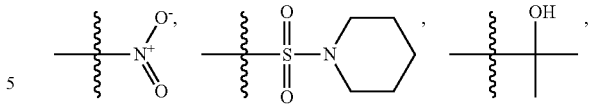

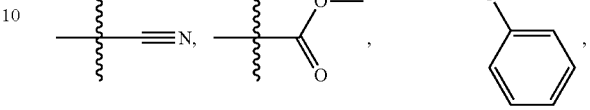

$E^7$ may be H, $CH_3$, $CH_2CH_3$, F, Cl, Br, $CF_3$, $OCF_3$, $OCF_2$, $S(=O)_2(NH_2)$, $OCH_2C(CH_3)(CH_2)$,

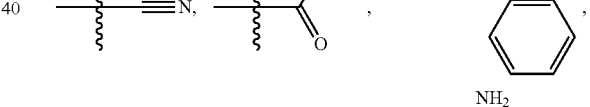

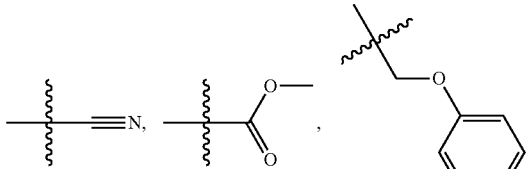

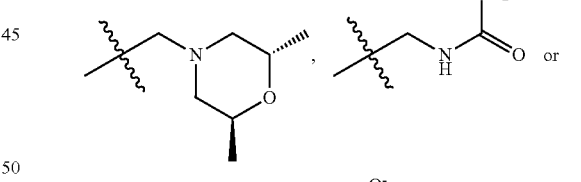

$G^1$ may be H, $OCH_3$, $CH_2CH_3$, F, Cl, Br, $CF_3$, $OCF_3$, $OCF_2$, $S(=O)_2(NH_2)$ or $OCH_2C(CH_3)(CH_2)$;

$L^1$ may be H, $CH_3$, $CH_2CH_3$, F, Cl, Br, $CF_3$, $OCF_3$, $OCF_2$, $S(=O)_2(NH_2)$, $OCH_2C(CH_3)(CH_2)$,

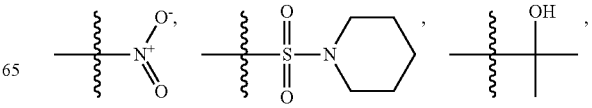

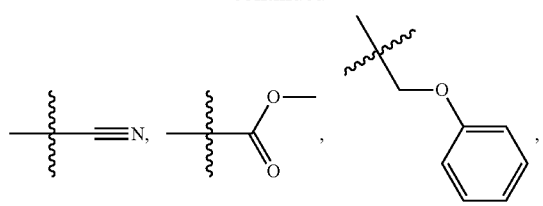
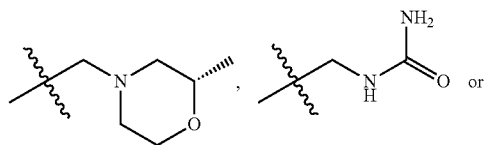
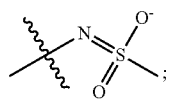
L² may be H, CH₃, CH₂CH₃, F, Cl, Br, CF₃, OCF₃, OCF₂, S(=O)₂(NH₂), OCH₂C(CH₃)(CH₂),
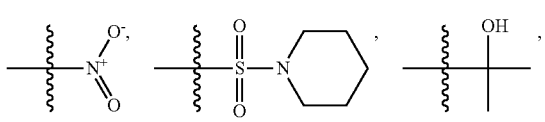
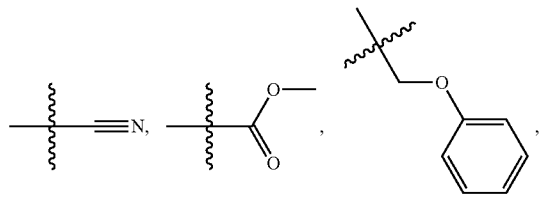
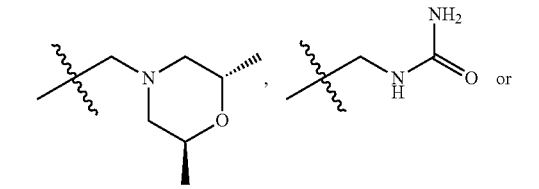
L³ may be H, CH₃, CH₂CH₃, F, Cl, Br, CF₃, OCF₃, OCF₂, S(=O)₂(NH₂), OCH₂C(CH₃)(CH₂),
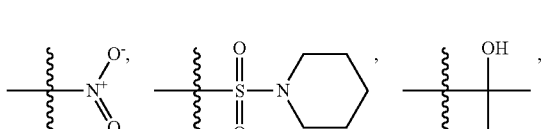
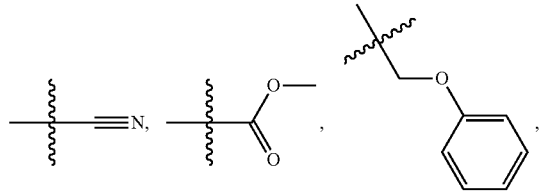
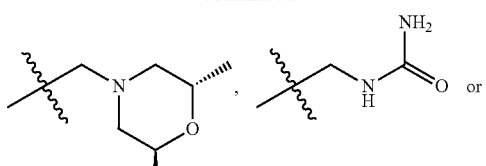
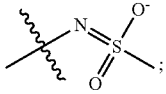
L⁴ may be H, CH₃, CH₂CH₃, F, Cl, Br, CF₃, OCF₃, OCF₂, S(=O)₂(NH₂), OCH₂C(CH₃)(CH₂),
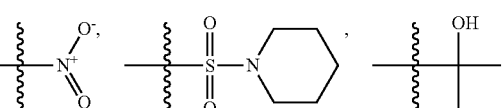
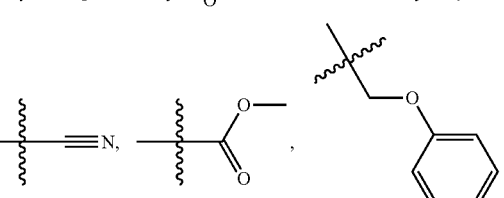
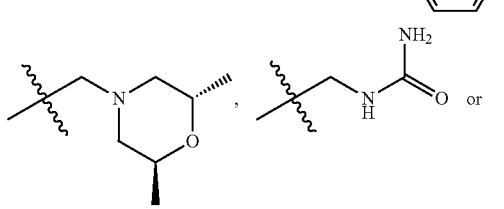
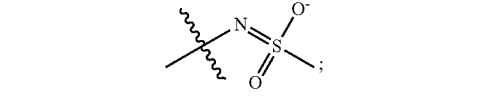
L⁵ may be H, CH₃, CH₂CH₃, F, Cl, Br, CF₃, OCF₃, OCF₂, S(=O)₂(NH₂), OCH₂C(CH₃)(CH₂),
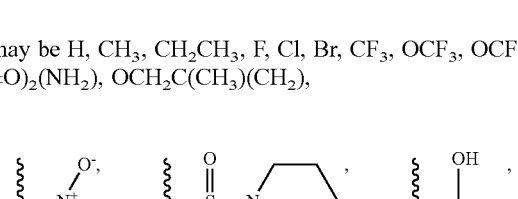
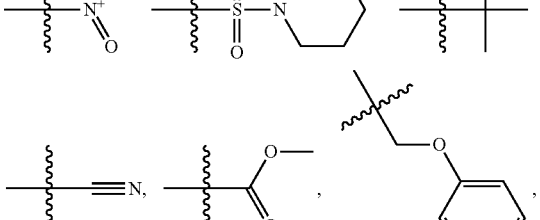
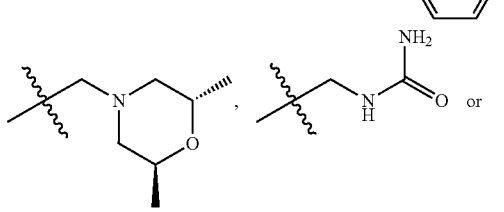

-continued

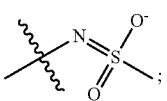

$L^6$ may be H, CH$_3$, CH$_2$CH$_3$, F, Cl, Br, CF$_3$, OCF$_3$, OCF$_2$, S(=O)$_2$(NH$_2$), OCH$_2$C(CH$_3$)(CH$_2$),

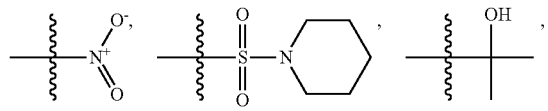

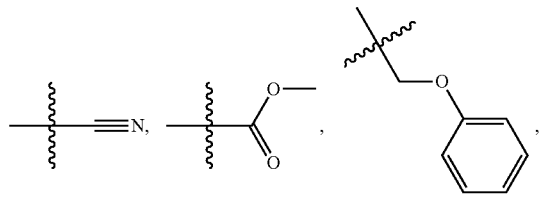

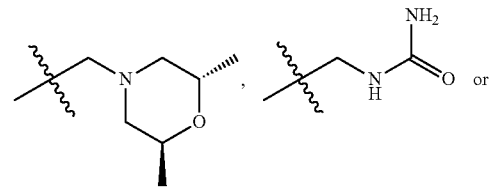

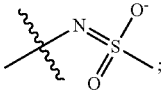

$L^7$ may be H, CH$_3$, CH$_2$CH$_3$, F, Cl, Br, CF$_3$, OCF$_3$, OCF$_2$, S(=O)$_2$(NH$_2$), OCH$_2$C(CH$_3$)(CH$_2$),

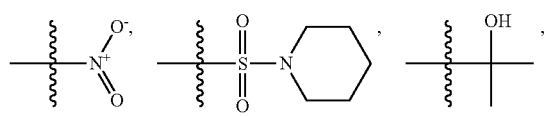

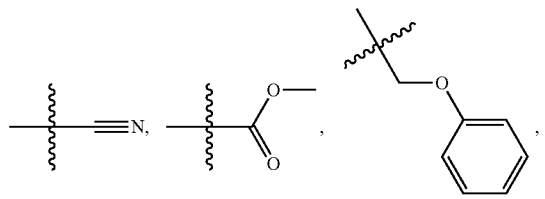

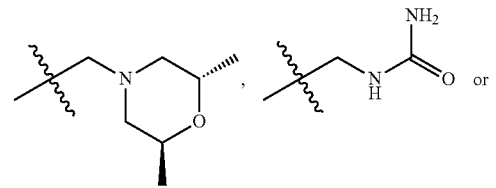

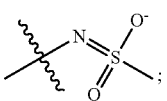

and
provided that when M$^1$ is

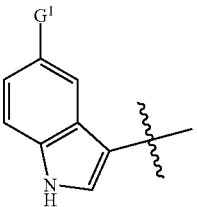

and G$^1$ is H, then n$^3$ is 1; and wherein the compound may be for use in the treatment of one or more of the following: prostate cancer; breast cancer; colon cancer; cervical cancer; small-cell lung carcinoma; neuroblastomas; osteosarcoma; glioblastoma; melanoma; and myeloid leukaemia. Alternatively, n$^2$ may be 0-3, wherein if n$^2$ may be 2 or 3, each T$^1$ may be
independently selected from H or CH$_3$.
M$^1$ may be selected from:

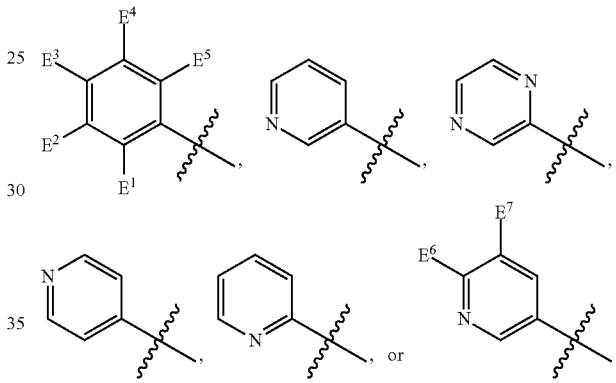

and M$^2$ may be selected from:

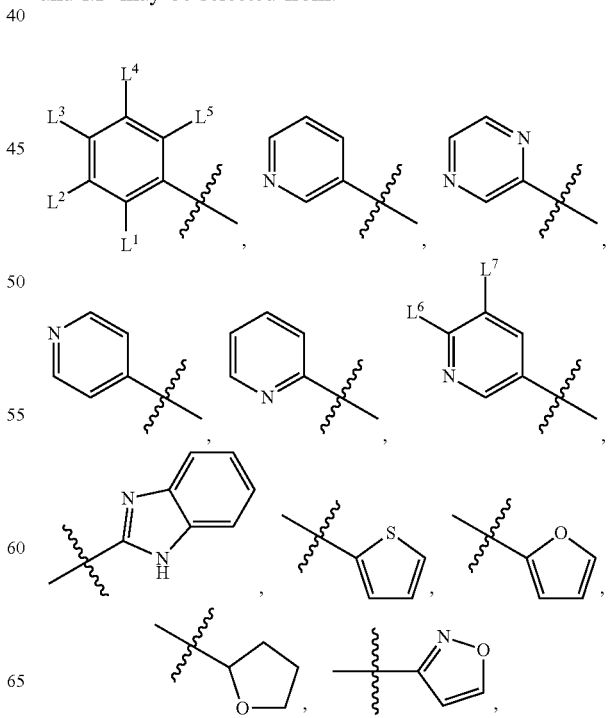

-continued
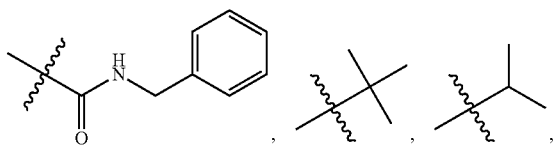
CH₃ or NH₂. M¹ may be selected from:
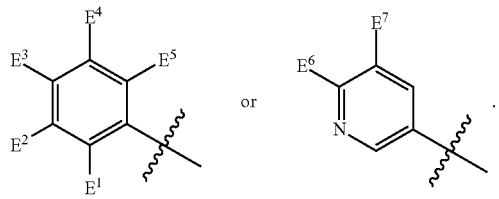
M¹ may be selected from:
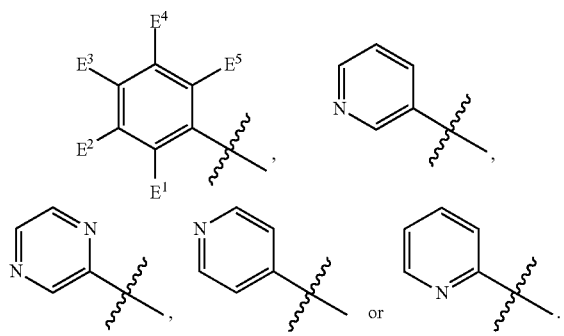
M¹ may be selected from:
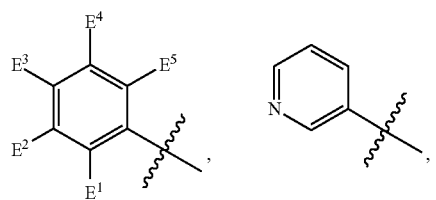
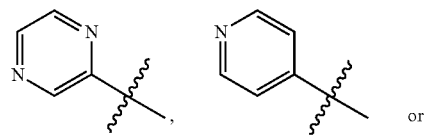
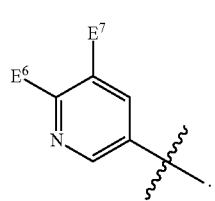
M¹ may be selected from:
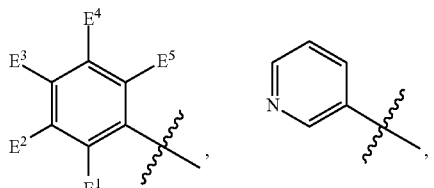
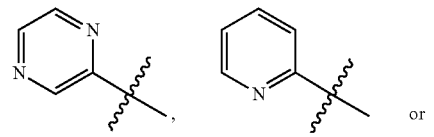
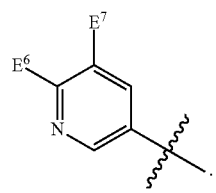
M¹ may be selected from:
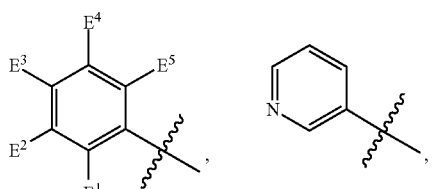
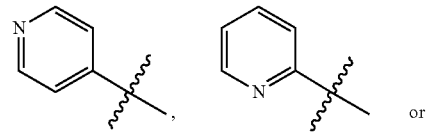
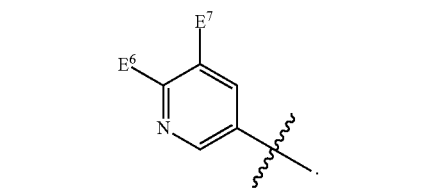
M¹ may be selected from:
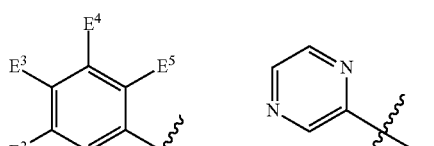
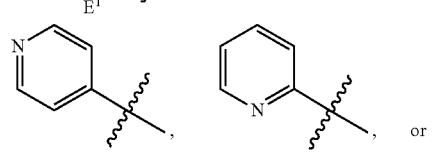

M¹ may be
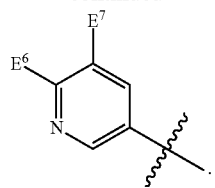
M² may be selected from:
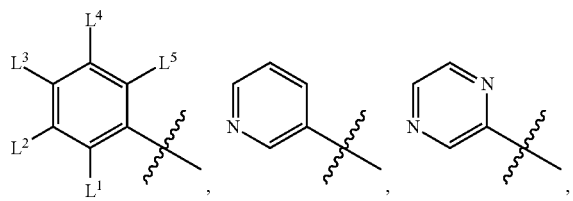
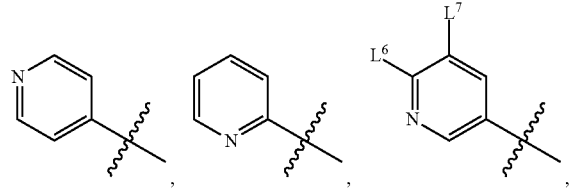
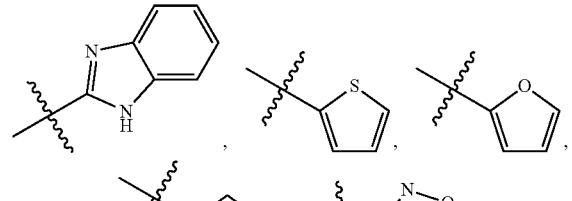
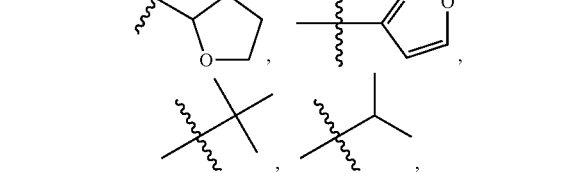
CH₃ or NH₂. M² may be selected from:
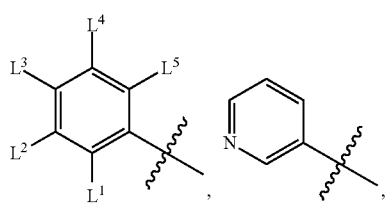
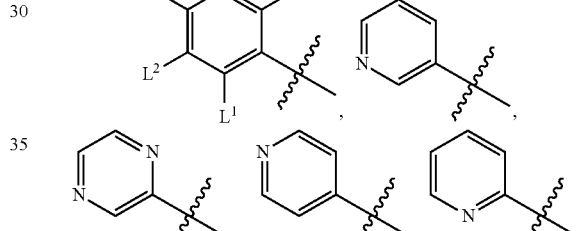
CH₃ or NH₂. M² may be selected from:
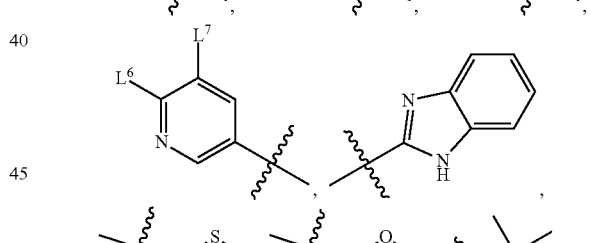
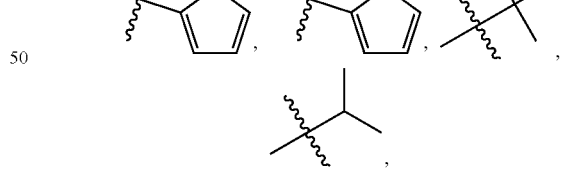
CH₃ or NH₂. M² may be selected from:
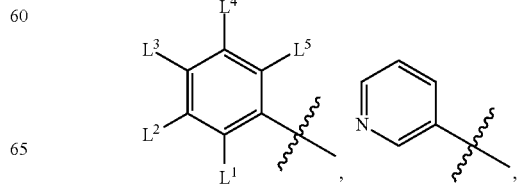

-continued
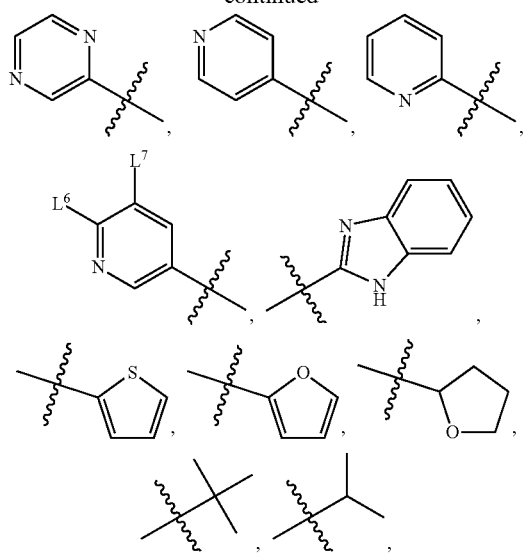
CH₃ or NH₂. M² may be selected from:
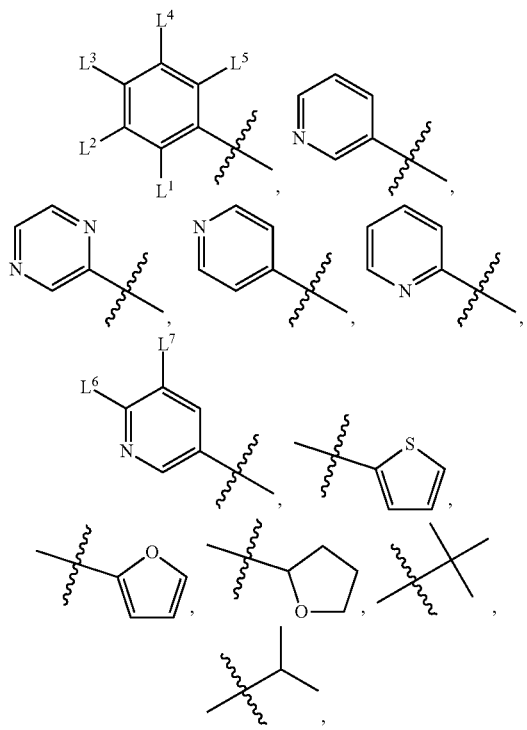
CH₃ or NH₂. M² may be selected from:
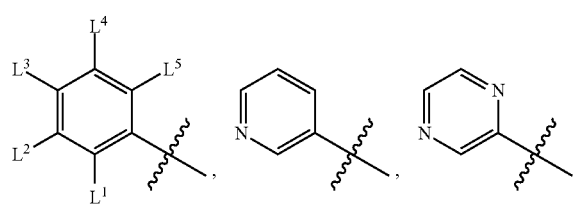
-continued
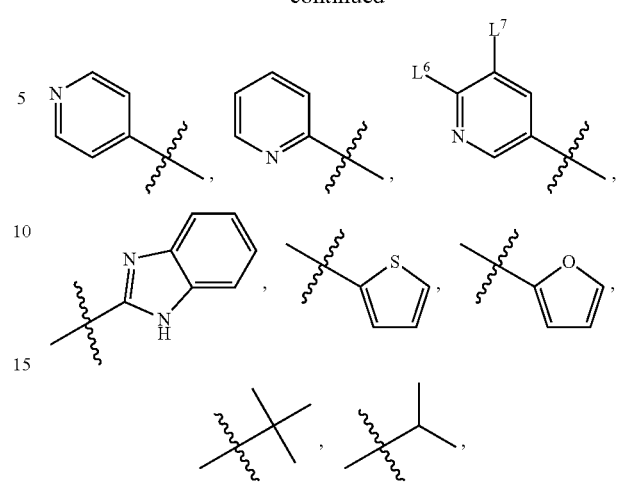
CH₃ or NH₂. M² may be selected from:
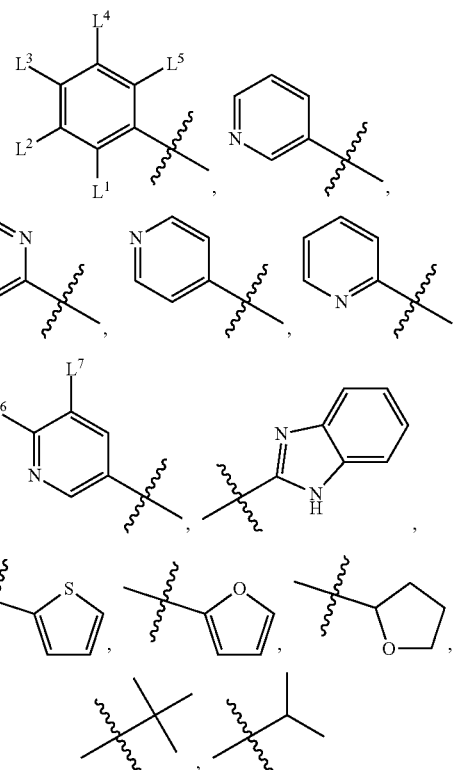
or CH₃. M² may be selected from:
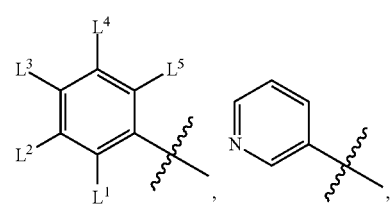

-continued
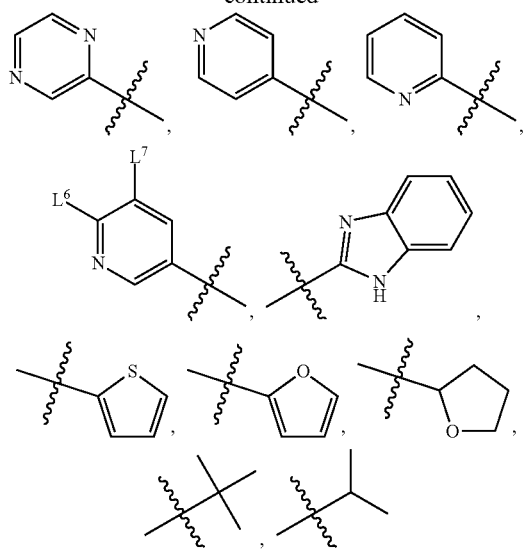
or NH₂. M² may be selected from:
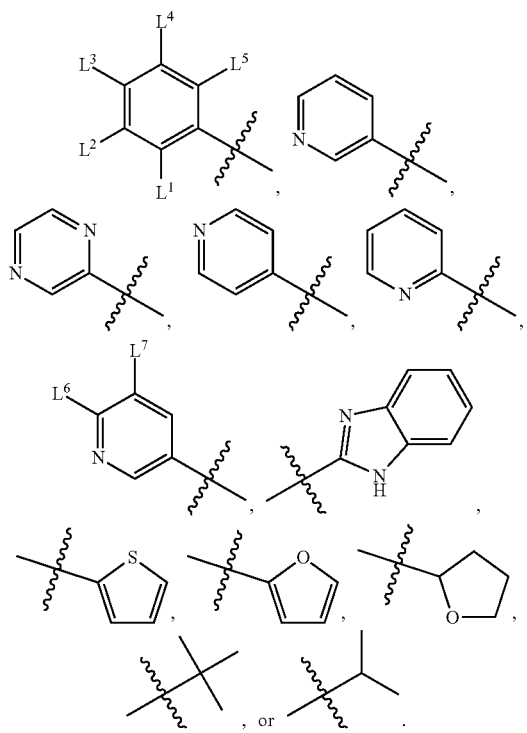
M² may be selected from:
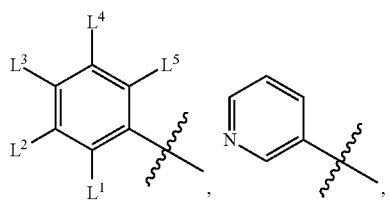
-continued
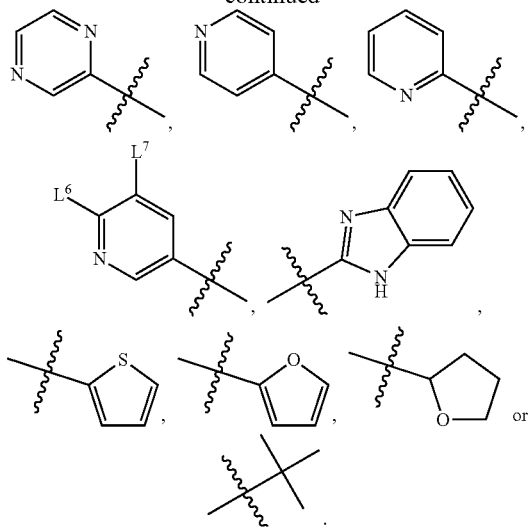
M² may be selected from:
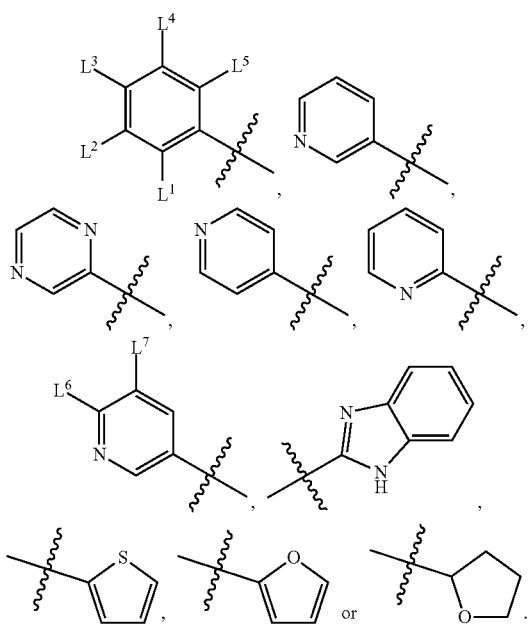
M² may be selected from:
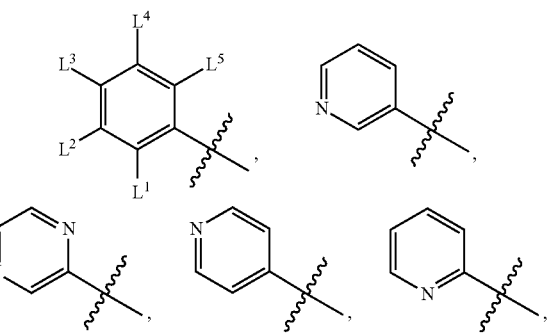

-continued
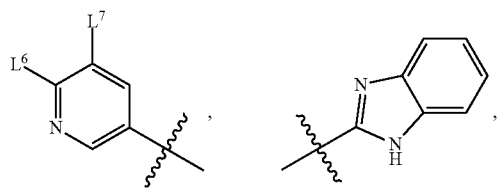
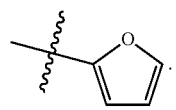
$M^2$ may be selected from:
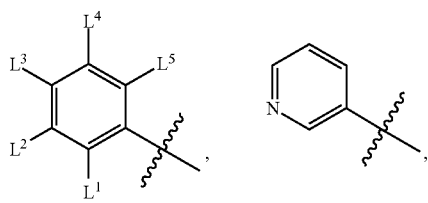
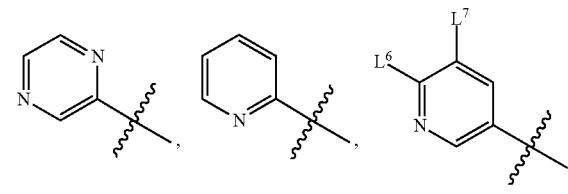
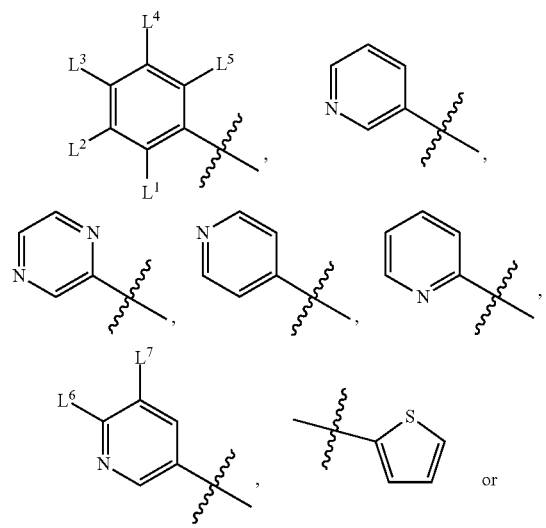
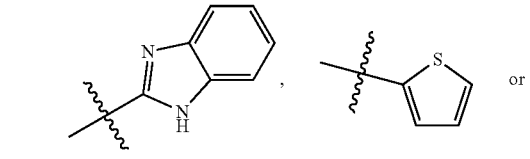
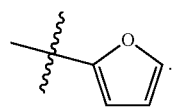
$M^2$ may be selected from:
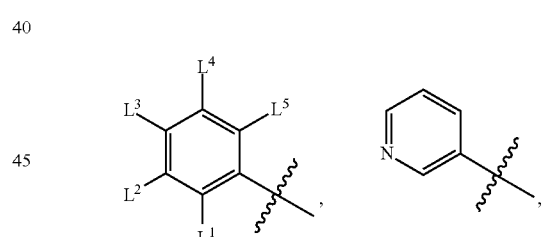
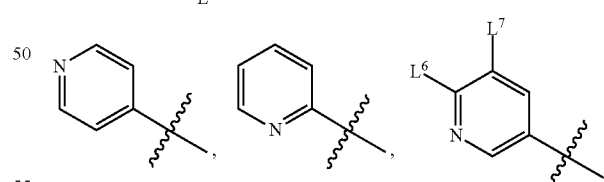
$M^2$ may be selected from:
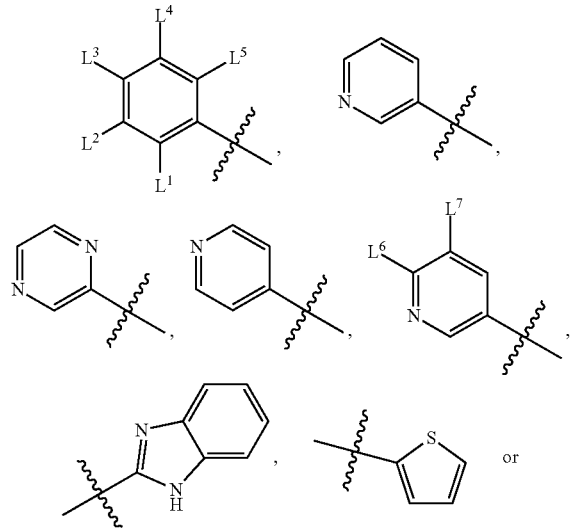
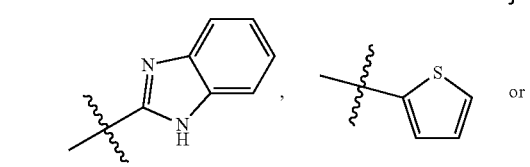
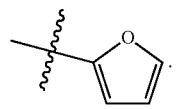

$M^2$ may be selected from:
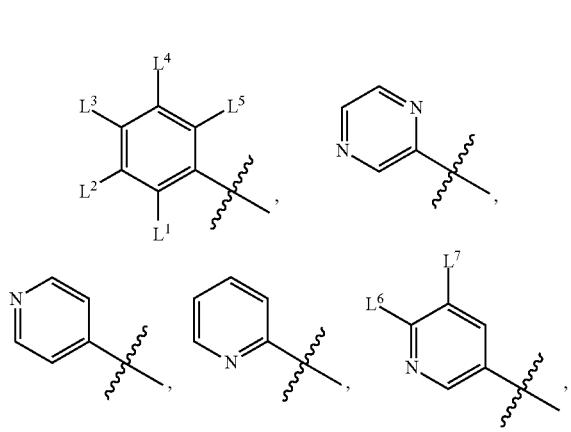
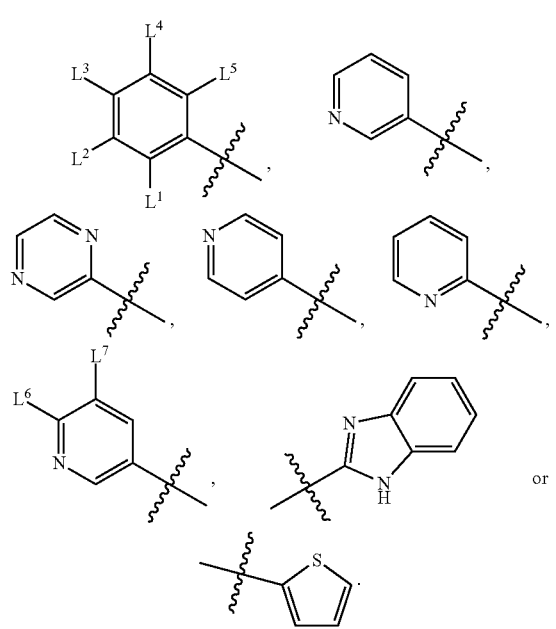
$M^2$ may be selected from:
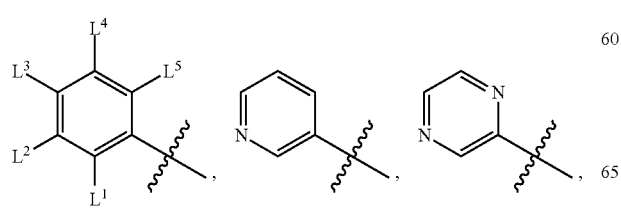
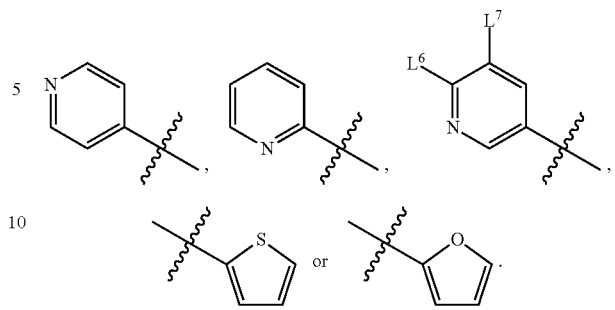
$M^2$ may be selected from:
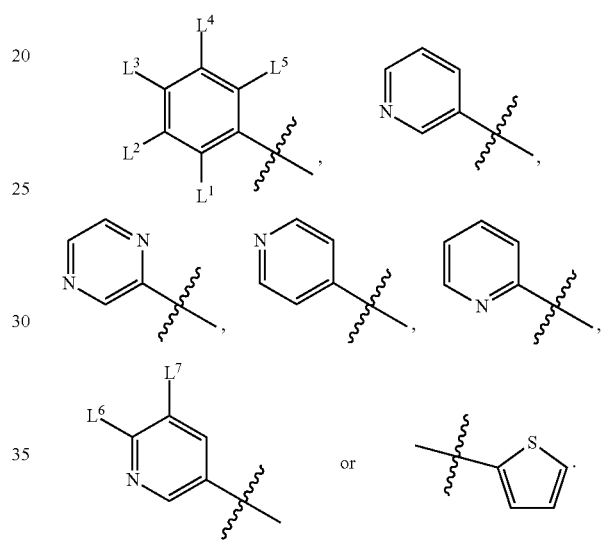
$M^2$ may be selected from:
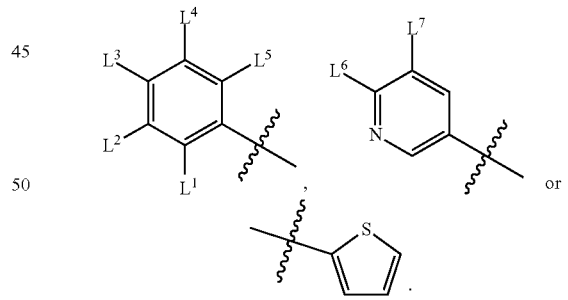
$M^2$ may be selected from:
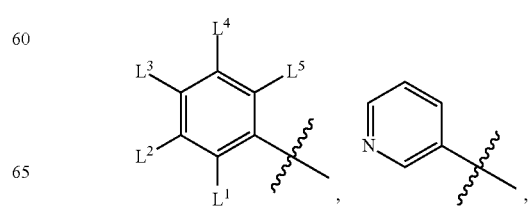

-continued

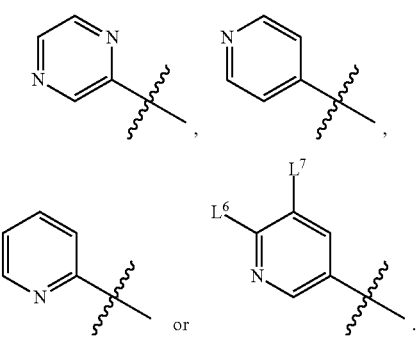

or

M² may be selected from:

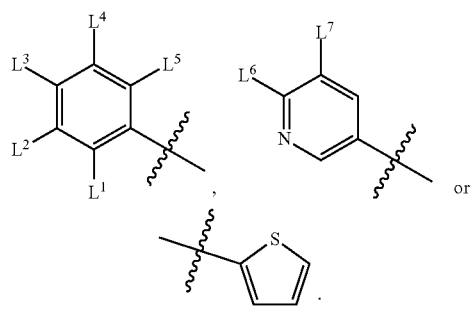

or

A¹ may be selected from CH₂, CH(CH₃) or CH(CH₂CH₃). A² may be CH₂ or CH(CH₃). G¹ may be H, OCH₃, CH₂CH₃, F, Cl, Br, CF₃, OCF₃, OCF₂ or S(=O)₂(NH₂). A¹ may be selected from CH₂ or CH(CH₃). A² may be CH₂. G¹ may be H, OCH₃, CH₂CH₃, F, Cl, Br, CF₃, OCF₃ or OCF₂. A¹ may be selected from CH₂. A² may be CH₂. A¹ may be absent where n¹ is 0. A² may be absent where n⁵ is 0. G¹ may be H, OCH₃, CH₂CH₃, F, Cl, Br, CF₃ or OCF₃. G¹ may be H, OCH₃, CH₂CH₃, F, Cl, Br or CF₃. G¹ may be H, F, Cl, Br or CF₃. G¹ may be H or S(=O)₂(NH₂). G¹ may be H, OCH₃, CH₂CH₃ or S(=O)₂(NH₂). G¹ may be H, F, Cl, Br or S(=O)₂(NH₂). G¹ may be H.

E¹ may be H, CH₃, CH₂CH₃, F, Cl, Br, CF₃, OCF₃, OCF₂, S(=O)₂(NH₂), OCH₂C(CH₃)(CH₂),

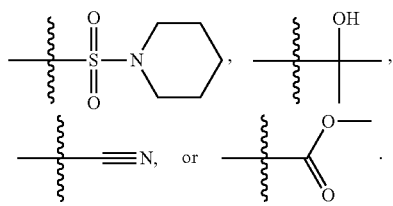

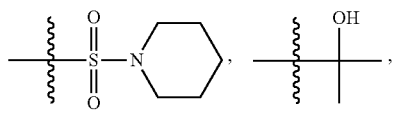

E² may be H, CH₃, CH₂CH₃, F, Cl, Br, CF₃, OCF₃, OCF₂, S(=O)₂(NH₂), OCH₂C(CH₃)(CH₂),

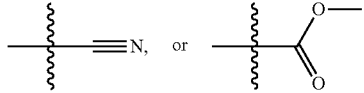

E³ may be H, CH₃, CH₂CH₃, F, Cl, Br, CF₃, OCF₃, OCF₂, S(=O)₂(NH₂), OCH₂C(CH₃)(CH₂),

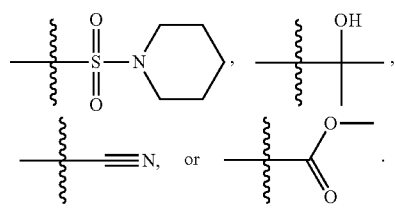

E⁴ may be H, CH₃, CH₂CH₃, F, Cl, Br, CF₃, OCF₃, OCF₂, S(=O)₂(NH₂), OCH₂C(CH₃)(CH₂),

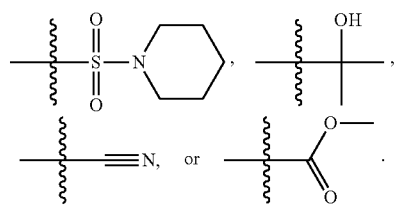

E⁵ may be H, CH₃, CH₂CH₃, F, Cl, Br, CF₃, OCF₃, OCF₂, S(=O)₂(NH₂), OCH₂C(CH₃)(CH₂),

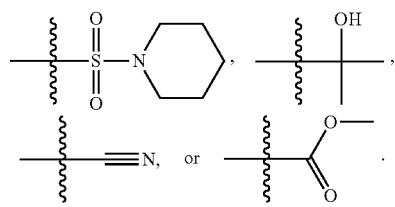

E⁶ may be H, CH₃, CH₂CH₃, F, Cl, Br, CF₃, OCF₃, OCF₂, S(=O)₂(NH₂), OCH₂C(CH₃)(CH₂),

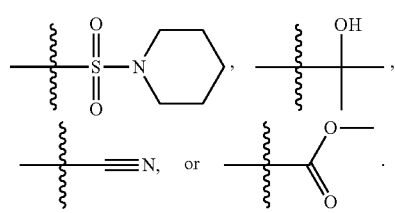

E⁷ may be H, CH₃, CH₂CH₃, F, Cl, Br, CF₃, OCF₃, OCF₂, S(=O)₂(NH₂), OCH₂C(CH₃)(CH₂),

-continued

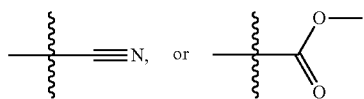

$E^1$ may be H, $CH_3$, $CH_2CH_3$, F, Cl, Br, $CF_3$, $OCF_3$, $OCF_2$, $S(=O)_2(NH_2)$ or $OCH_2C(CH_3)(CH_2)$. $E^2$ may be H, $CH_3$, $CH_2CH_3$, F, Cl, Br, $CF_3$, $OCF_3$, $OCF_2$, $S(=O)_2(NH_2)$ or $OCH_2C(CH_3)(CH_2)$. $E^3$ may be H, $CH_3$, $CH_2CH_3$, F, Cl, Br, $CF_3$, $OCF_3$, $OCF_2$, $S(=O)_2(NH_2)$ or $OCH_2C(CH_3)(CH_2)$. $E^4$ may be H, $CH_3$, $CH_2CH_3$, F, Cl, Br, $CF_3$, $OCF_3$, $OCF_2$, $S(=O)_2(NH_2)$ or $OCH_2C(CH_3)(CH_2)$. $E^5$ may be H, $CH_3$, $CH_2CH_3$, F, Cl, Br, $CF_3$, $OCF_3$, $OCF_2$, $S(=O)_2(NH_2)$ or $OCH_2C(CH_3)(CH_2)$. $E^6$ may be H, $CH_3$, $CH_2CH_3$, F, Cl, Br, $CF_3$, $OCF_3$, $OCF_2$, $S(=O)_2(NH_2)$ or $OCH_2C(CH_3)(CH_2)$. $E^7$ may be H, $CH_3$, $CH_2CH_3$, F, Cl, Br, $CF_3$, $OCF_3$, $OCF_2$, $S(=O)_2(NH_2)$ or $OCH_2C(CH_3)(CH_2)$. $E^1$ may be H, $CH_3$, $CH_2CH_3$, F, Cl, Br, $CF_3$, $OCF_3$ or $OCF_2$. $E^2$ may be H, $CH_3$, $CH_2CH_3$, F, Cl, Br, $CF_3$, $OCF_3$ or $OCF_2$. $E^3$ may be H, $CH_3$, $CH_2CH_3$, F, Cl, Br, $CF_3$, $OCF_3$ or $OCF_2$. $E^4$ may be H, $CH_3$, $CH_2CH_3$, F, Cl, Br, $CF_3$, $OCF_3$ or $OCF_2$. $E^5$ may be H, $CH_3$, $CH_2CH_3$, F, Cl, Br, $CF_3$, $OCF_3$ or $OCF_2$. $E^6$ may be H, $CH_3$, $CH_2CH_3$, F, Cl, Br, $CF_3$, $OCF_3$ or $OCF_2$. $E^7$ may be H, $CH_3$, $CH_2CH_3$, F, Cl, Br, $CF_3$, $OCF_3$ or $OCF_2$. $E^1$ may be H, $CH_3$, $CH_2CH_3$, F, Cl, Br or $CF_3$. $E^2$ may be H, $CH_3$, $CH_2CH_3$, F, Cl, Br or $CF_3$. $E^3$ may be H, $CH_3$, $CH_2CH_3$, F, Cl, Br or $CF_3$. $E^4$ may be H, $CH_3$, $CH_2CH_3$, F, Cl, Br or $CF_3$. $E^5$ may be H, $CH_3$, $CH_2CH_3$, F, Cl, Br or $CF_3$. $E^6$ may be H, $CH_3$, $CH_2CH_3$, F, Cl, Br or $CF_3$. $E^7$ may be H, $CH_3$, $CH_2CH_3$, F, Cl, Br or $CF_3$. $E^1$ may be H, F, Cl, Br or $CF_3$. $E^2$ may be H, F, Cl, Br or $CF_3$. $E^3$ may be H, F, Cl, Br or $CF_3$. $E^4$ may be H, F, Cl, Br or $CF_3$. $E^5$ may be H, F, Cl, Br or $CF_3$. $E^6$ may be H, F, Cl, Br or $CF_3$. $E^7$ may be H, F, Cl, Br or $CF_3$.

$L^1$ may be H, $CH_3$, $CH_2CH_3$, F, Cl, Br, $CF_3$, $OCF_3$, $OCF_2$, $S(=O)_2(NH_2)$, $OCH_2C(CH_3)(CH_2)$,

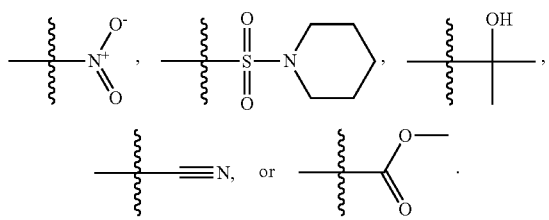

$L^2$ may be H, $CH_3$, $CH_2CH_3$, F, Cl, Br, $CF_3$, $OCF_3$, $OCF_2$, $S(=O)_2(NH_2)$, $OCH_2C(CH_3)(CH_2)$,

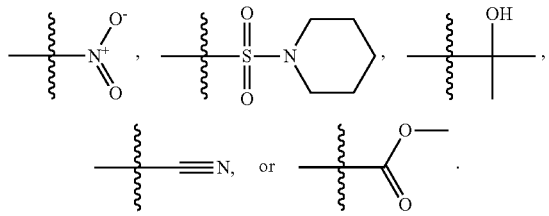

$L^3$ may be H, $CH_3$, $CH_2CH_3$, F, Cl, Br, $CF_3$, $OCF_3$, $OCF_2$, $S(=O)_2(NH_2)$, $OCH_2C(CH_3)(CH_2)$,

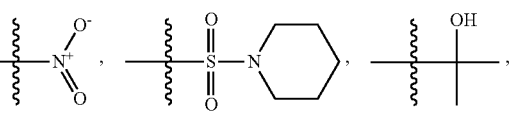

$L^4$ may be H, $CH_3$, $CH_2CH_3$, F, Cl, Br, $CF_3$, $OCF_3$, $OCF_2$, $S(=O)_2(NH_2)$, $OCH_2C(CH_3)(CH_2)$,

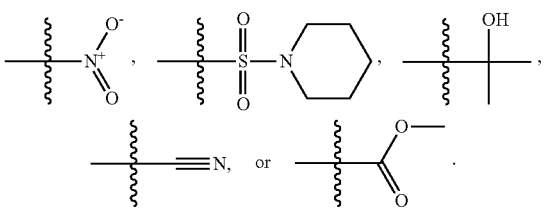

$L^5$ may be H, $CH_3$, $CH_2CH_3$, F, Cl, Br, $CF_3$, $OCF_3$, $OCF_2$, $S(=O)_2(NH_2)$, $OCH_2C(CH_3)(CH_2)$,

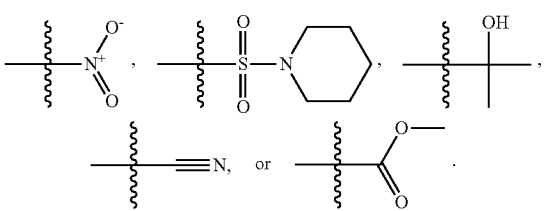

$L^6$ may be H, $CH_3$, $CH_2CH_3$, F, Cl, Br, $CF_3$, $OCF_3$, $OCF_2$, $S(=O)_2(NH_2)$, $OCH_2C(CH_3)(CH_2)$,

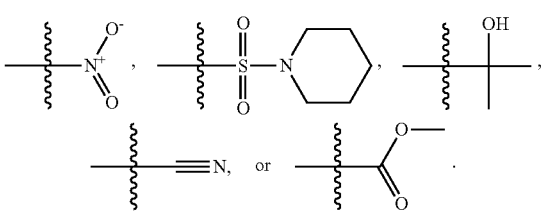

$L^7$ may be H, $CH_3$, $CH_2CH_3$, F, Cl, Br, $CF_3$, $OCF_3$, $OCF_2$, $S(=O)_2(NH_2)$, $OCH_2C(CH_3)(CH_2)$,

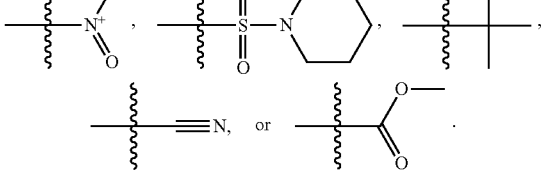

$L^1$ may be H, $CH_3$, $CH_2CH_3$, F, Cl, Br, $CF_3$, $OCF_3$, $OCF_2$, $S(=O)_2(NH_2)$, $OCH_2C(CH_3)(CH_2)$,

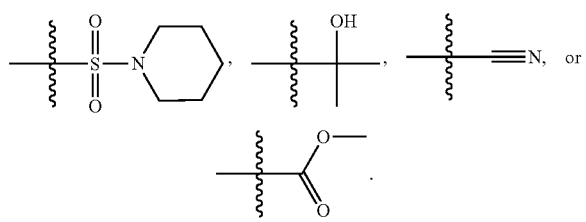

$L^2$ may be H, CH$_3$, CH$_2$CH$_3$, F, Cl, Br, CF$_3$, OCF$_3$, OCF$_2$, S(=O)$_2$(NH$_2$), OCH$_2$C(CH$_3$)(CH$_2$),

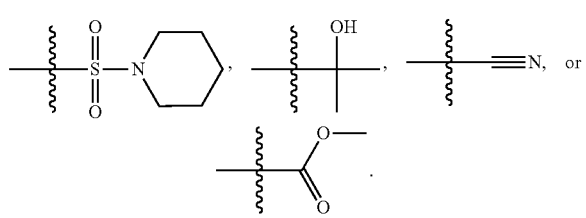

$L^3$ may be H, CH$_3$, CH$_2$CH$_3$, F, Cl, Br, CF$_3$, OCF$_3$, OCF$_2$, S(=O)$_2$(NH$_2$), OCH$_2$C(CH$_3$)(CH$_2$),

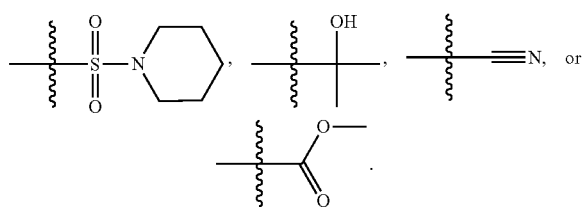

$L^4$ may be H, CH$_3$, CH$_2$CH$_3$, F, Cl, Br, CF$_3$, OCF$_3$, OCF$_2$, S(=O)$_2$(NH$_2$), OCH$_2$C(CH$_3$)(CH$_2$),

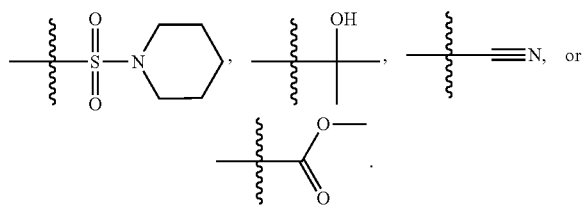

$L^5$ may be H, CH$_3$, CH$_2$CH$_3$, F, Cl, Br, CF$_3$, OCF$_3$, OCF$_2$, S(=O)$_2$(NH$_2$), OCH$_2$C(CH$_3$)(CH$_2$),

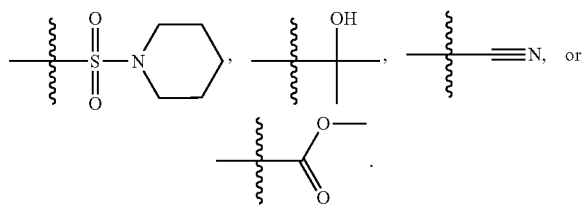

$L^6$ may be H, CH$_3$, CH$_2$CH$_3$, F, Cl, Br, CF$_3$, OCF$_3$, OCF$_2$, S(=O)$_2$(NH$_2$), OCH$_2$C(CH$_3$)(CH$_2$),

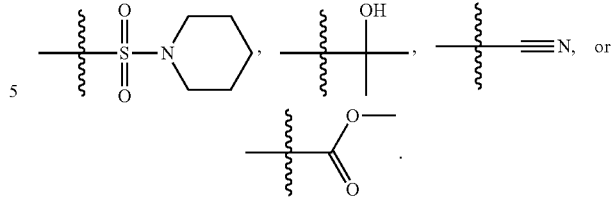

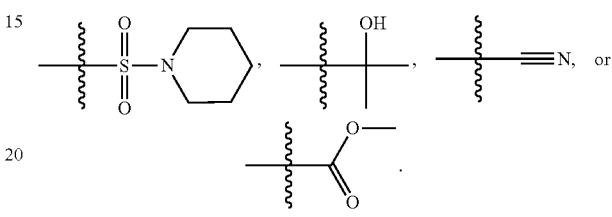

$L^7$ may be H, CH$_3$, CH$_2$CH$_3$, F, Cl, Br, CF$_3$, OCF$_3$, OCF$_2$, S(=O)$_2$(NH$_2$), OCH$_2$C(CH$_3$)(CH$_2$),

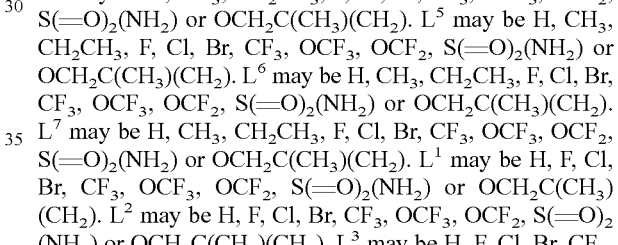

$L^1$ may be H, CH$_3$, CH$_2$CH$_3$, F, Cl, Br, CF$_3$, OCF$_3$, OCF$_2$, S(=O)$_2$(NH$_2$) or OCH$_2$C(CH$_3$)(CH$_2$). $L^2$ may be H, CH$_3$, CH$_2$CH$_3$, F, Cl, Br, CF$_3$, OCF$_3$, OCF$_2$, S(=O)$_2$(NH$_2$) or OCH$_2$C(CH$_3$)(CH$_2$). $L^3$ may be H, CH$_3$, CH$_2$CH$_3$, F, Cl, Br, CF$_3$, OCF$_3$, OCF$_2$, S(=O)$_2$(NH$_2$) or OCH$_2$C(CH$_3$)(CH$_2$). $L^4$ may be H, CH$_3$, CH$_2$CH$_3$, F, Cl, Br, CF$_3$, OCF$_3$, OCF$_2$, S(=O)$_2$(NH$_2$) or OCH$_2$C(CH$_3$)(CH$_2$). $L^5$ may be H, CH$_3$, CH$_2$CH$_3$, F, Cl, Br, CF$_3$, OCF$_3$, OCF$_2$, S(=O)$_2$(NH$_2$) or OCH$_2$C(CH$_3$)(CH$_2$). $L^6$ may be H, CH$_3$, CH$_2$CH$_3$, F, Cl, Br, CF$_3$, OCF$_3$, OCF$_2$, S(=O)$_2$(NH$_2$) or OCH$_2$C(CH$_3$)(CH$_2$). $L^7$ may be H, CH$_3$, CH$_2$CH$_3$, F, Cl, Br, CF$_3$, OCF$_3$, OCF$_2$, S(=O)$_2$(NH$_2$) or OCH$_2$C(CH$_3$)(CH$_2$). $L^1$ may be H, F, Cl, Br, CF$_3$, OCF$_3$, OCF$_2$, S(=O)$_2$(NH$_2$) or OCH$_2$C(CH$_3$)(CH$_2$). $L^2$ may be H, F, Cl, Br, CF$_3$, OCF$_3$, OCF$_2$, S(=O)$_2$(NH$_2$) or OCH$_2$C(CH$_3$)(CH$_2$). $L^3$ may be H, F, Cl, Br, CF$_3$, OCF$_3$, OCF$_2$, S(=O)$_2$(NH$_2$) or OCH$_2$C(CH$_3$)(CH$_2$). $L^4$ may be H, F, Cl, Br, CF$_3$, OCF$_3$, OCF$_2$, S(=O)$_2$(NH$_2$) or OCH$_2$C(CH$_3$)(CH$_2$). $L^5$ may be H, F, Cl, Br, CF$_3$, OCF$_3$, OCF$_2$, S(=O)$_2$(NH$_2$) or OCH$_2$C(CH$_3$)(CH$_2$). $L^6$ may be H, F, Cl, Br, CF$_3$, OCF$_3$, OCF$_2$, S(=O)$_2$(NH$_2$) or OCH$_2$C(CH$_3$)(CH$_2$). $L^7$ may be H, F, Cl, Br, CF$_3$, OCF$_3$, OCF$_2$, S(=O)$_2$(NH$_2$) or OCH$_2$C(CH$_3$)(CH$_2$). $L^1$ may be H, CH$_3$, CH$_2$CH$_3$, F, Cl, Br, CF$_3$, OCF$_3$ or OCF$_2$. $L^2$ may be H, CH$_3$, CH$_2$CH$_3$, F, Cl, Br, CF$_3$, OCF$_3$ or OCF$_2$. $L^3$ may be H, CH$_3$, CH$_2$CH$_3$, F, Cl, Br, CF$_3$, OCF$_3$ or OCF$_2$. $L^4$ may be H, CH$_3$, CH$_2$CH$_3$, F, Cl, Br, CF$_3$, OCF$_3$ or OCF$_2$. $L^5$ may be H, CH$_3$, CH$_2$CH$_3$, F, Cl, Br, CF$_3$, OCF$_3$ or OCF$_2$. $L^6$ may be H, CH$_3$, CH$_2$CH$_3$, F, Cl, Br, CF$_3$, OCF$_3$ or OCF$_2$. $L^7$ may be H, CH$_3$, CH$_2$CH$_3$, F, Cl, Br, CF$_3$, OCF$_3$ or OCF$_2$. $L^1$ may be H, F, Cl, Br, CF$_3$, OCF$_3$ or OCF$_2$. $L^2$ may be H, F, Cl, Br, CF$_3$, OCF$_3$ or OCF$_2$. $L^3$ may be H, F, Cl, Br, CF$_3$, OCF$_3$ or OCF$_2$. $L^4$ may be H, F, Cl, Br, CF$_3$, OCF$_3$ or OCF$_2$. $L^5$ may be H, F, Cl, Br, CF$_3$, OCF$_3$ or OCF$_2$. $L^6$ may be H, F, Cl, Br, CF$_3$, OCF$_3$ or OCF$_2$. $L^7$ may be H, F, Cl, Br, CF$_3$, OCF$_3$ or OCF$_2$. $L^1$ may be H, CH$_3$, F, Cl, Br, CF$_3$, OCF$_3$ or OCF$_2$. $L^2$ may be H, CH$_3$, F, Cl, Br, CF$_3$, OCF$_3$ or OCF$_2$. $L^3$ may be H, CH$_3$, F, Cl, Br, CF$_3$, OCF$_3$ or OCF$_2$. $L^4$ may be H, CH$_3$, F, Cl, Br, CF$_3$, OCF$_3$ or OCF$_2$. $L^5$ may be H, CH$_3$, F, Cl, Br, CF$_3$, OCF$_3$ or OCF$_2$. $L^6$ may be H, CH$_3$, F, Cl, Br, CF$_3$, OCF$_3$ or OCF$_2$. $L^7$ may be H, CH$_3$, F, Cl, Br, CF$_3$, OCF$_3$ or OCF$_2$. $L^1$ may be H, F, Cl, Br or CF$_3$. $L^2$ may be H, F, Cl, Br or CF$_3$. $L^3$ may be H, F, Cl, Br or CF$_3$. $L^4$ may be H, F, Cl, Br or CF$_3$. L$^5$ may be H, F, Cl, Br or CF$_3$. L$^6$ may be H, F, Cl, Br or CF$_3$. L$^7$ may be H, F, Cl, Br or CF$_3$.

In accordance with another embodiment, there is provided a compound of any one of claims 1-4, wherein the compound has the structure of Formula II:

Formula II

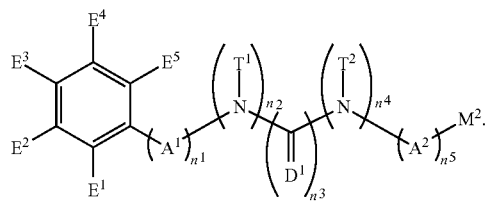

In accordance with another embodiment, there is provided a compound of any one of claims 1-5, wherein the compound has the structure of Formula III:

Formula III

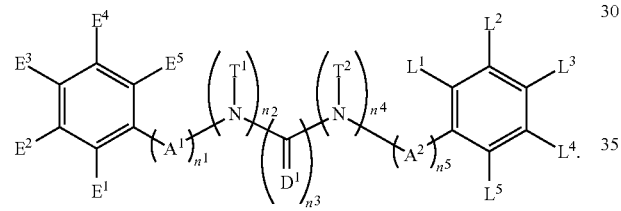

The compound may be selected from TABLE 3. The compound may be one or more of VPC-70063 or VPC-70063. The compound may be one or more of VPC-70063, VPC-70223; VPC-70215; VPC-70021; VPC-70277; VPC-70314; VPC-70033; VPC-70084; VPC-70413; VPC-70511; VPC-70514; VPC-70523; VPC-70524; VPC-70525; VPC-70532; VPC-70498; VPC-70495; VPC-70489; VPC-70477; VPC-70390; VPC-70393; VPC-70496; VPC-70535; VPC-70561; VPC-70526; VPC-70529; VPC-70530; VPC-70465; VPC-70527; VPC-70478; VPC-70501; VPC-70506; VPC-70437; VPC-70458; VPC-70466; VPC-70387; and VPC-70531.

In accordance with another embodiment, there is provided a compound, the compound having the structure of Formula IV:

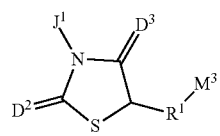

Formula IV, wherein, D$^2$ may be O or S; D$^3$ may be O or S; J$^1$ may be H, CH$_3$, CH$_2$CH$_3$,

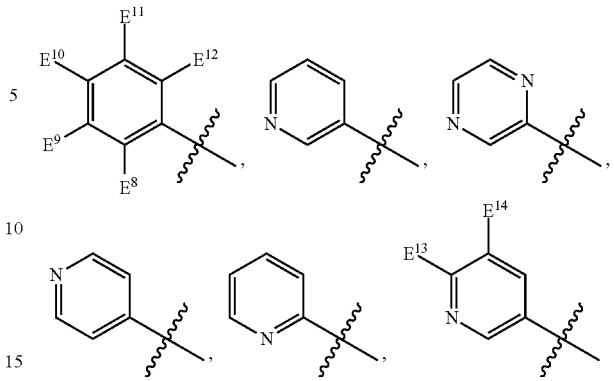

or may be absent (+); R$^1$ may be

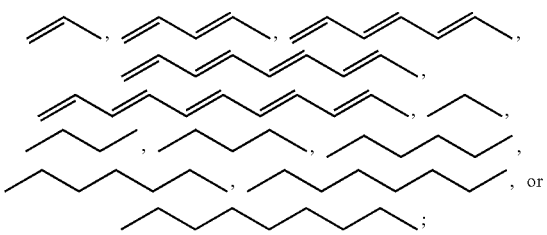

M$^3$ may be selected from:

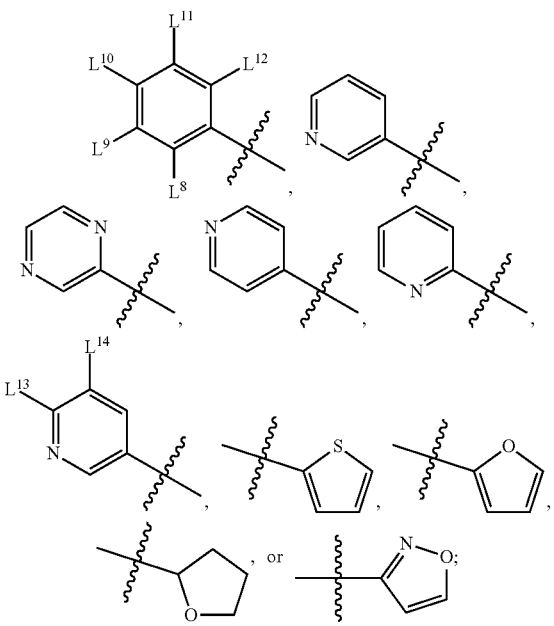

E$^8$ may be H, CH$_3$, CH$_2$CH$_3$, F, Cl, Br, or CF$_3$; E$^9$ may be H, CH$_3$, CH$_2$CH$_3$, F, Cl, Br, or CF$_3$; E$^{10}$ may be H, CH$_3$, CH$_2$CH$_3$, F, Cl, Br, or CF$_3$; E$^{11}$ may be H, CH$_3$, CH$_2$CH$_3$, F, Cl, Br, or CF$_3$; E$^{12}$ may be H, CH$_3$, CH$_2$CH$_3$, F, Cl, Br, or CF$_3$; E$^{13}$ may be H, CH$_3$, CH$_2$CH$_3$, F, Cl, Br, or CF$_3$; E$^{14}$ may be H, CH$_3$, CH$_2$CH$_3$, F, Cl, Br, or CF$_3$; L$^8$ may be H, CH$_3$, CH$_2$CH$_3$, F, Cl, Br, CF$_3$, OCF$_3$, OCF$_2$, S(=O)$_2$(NH$_2$), OCH$_2$C(CH$_3$)(CH$_2$),

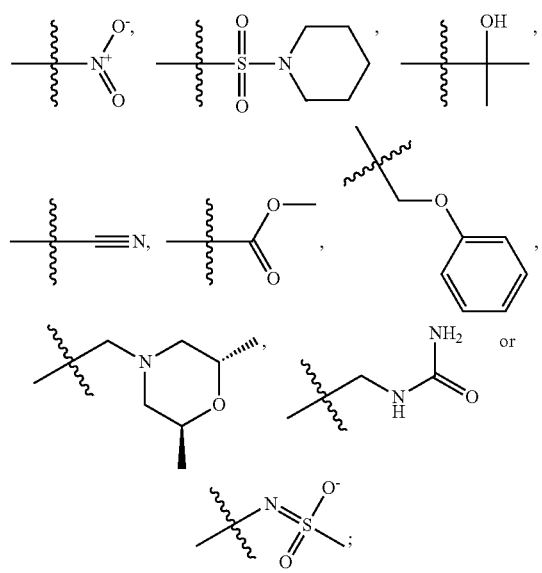

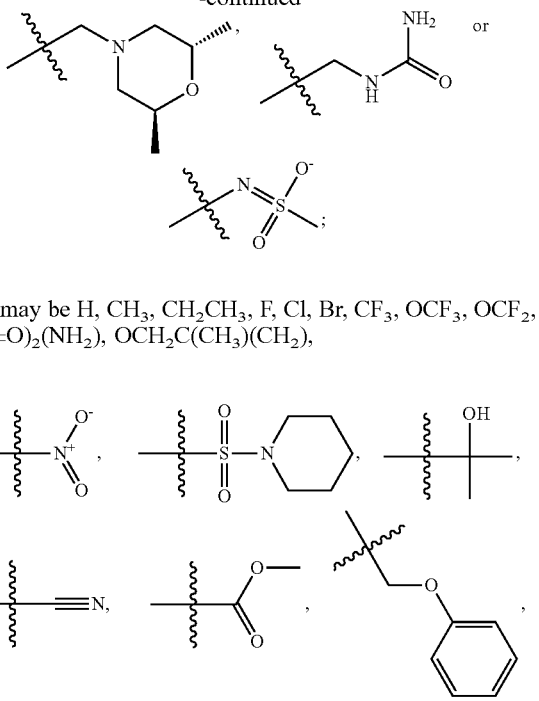

$L^{11}$ may be H, CH$_3$, CH$_2$CH$_3$, F, Cl, Br, CF$_3$, OCF$_3$, OCF$_2$, S(=O)$_2$(NH$_2$), OCH$_2$C(CH$_3$)(CH$_2$),

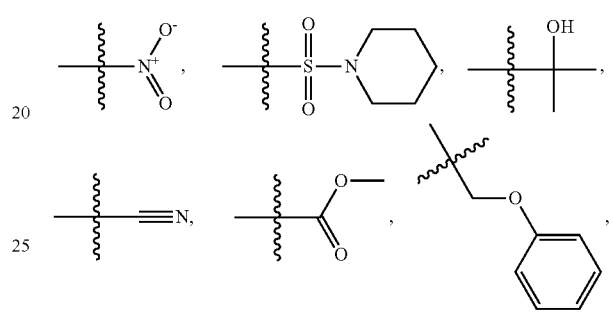

$L^9$ may be H, CH$_3$, CH$_2$CH$_3$, F, Cl, Br, CF$_3$, OCF$_3$, OCF$_2$, S(=O)$_2$(NH$_2$), OCH$_2$C(CH$_3$)(CH$_2$),

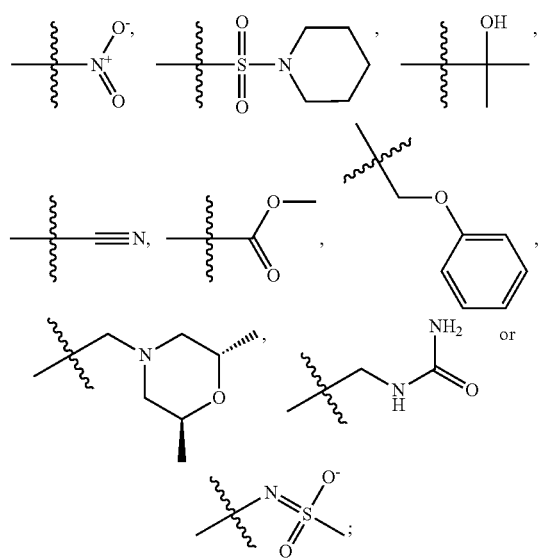

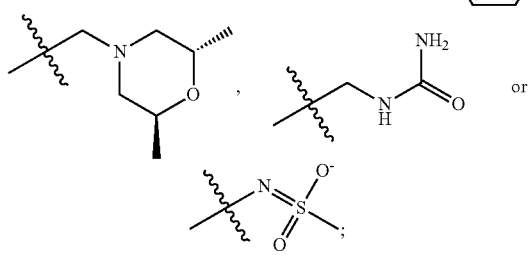

$L^{12}$ may be H, CH$_3$, CH$_2$CH$_3$, F, Cl, Br, CF$_3$, OCF$_3$, OCF$_2$, S(=O)$_2$(NH$_2$), OCH$_2$C(CH$_3$)(CH$_2$),

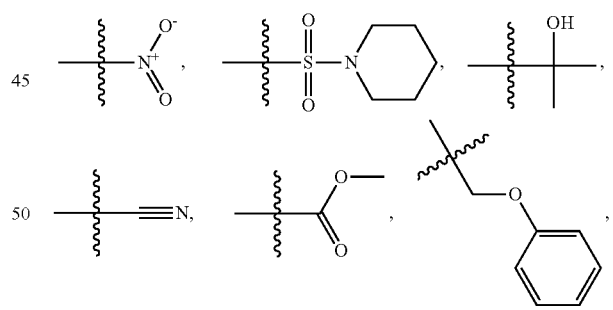

$L^{10}$ may be H, CH$_3$, CH$_2$CH$_3$, F, Cl, Br, CF$_3$, OCF$_3$, OCF$_2$, S(=O)$_2$(NH$_2$), OCH$_2$C(CH$_3$)(CH$_2$),

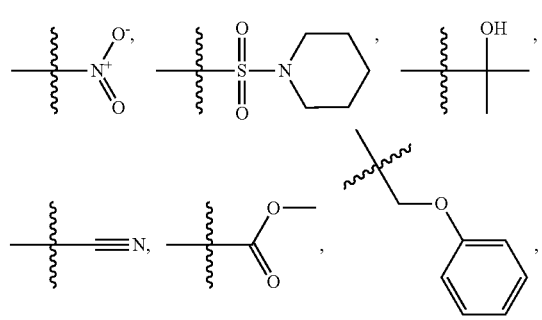

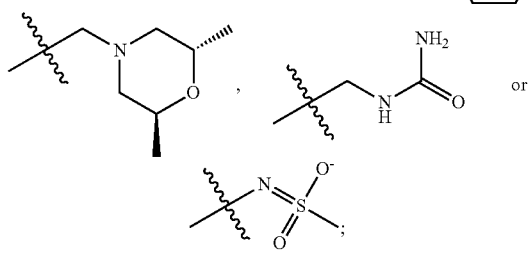

$L^{13}$ may be H, CH$_3$, CH$_2$CH$_3$, F, Cl, Br, or CF$_3$; and $L^{14}$ may be H, CH$_3$, CH$_2$CH$_3$, F, Cl, Br, or CF$_3$; and wherein the compound may be for use in the treatment of one or more of the following: prostate cancer; breast cancer; colon cancer; cervical cancer; small-cell lung carcinoma; neuroblastomas; osteosarcoma; glioblastoma; melanoma; and myeloid leukaemia.
M³ may be selected from:
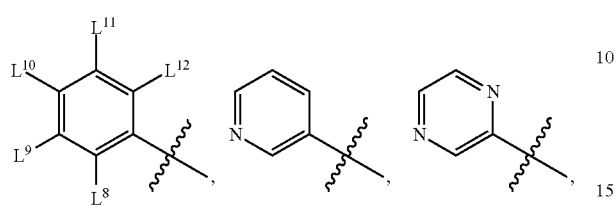
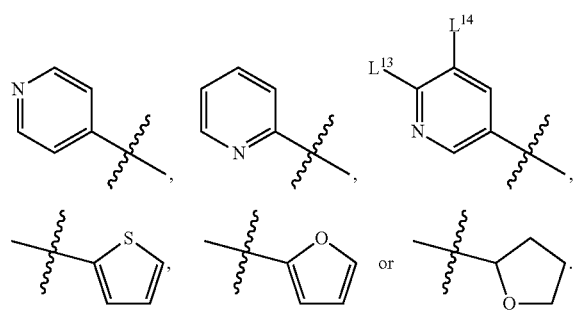
M³ may be selected from:
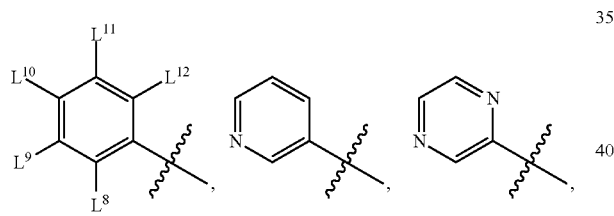
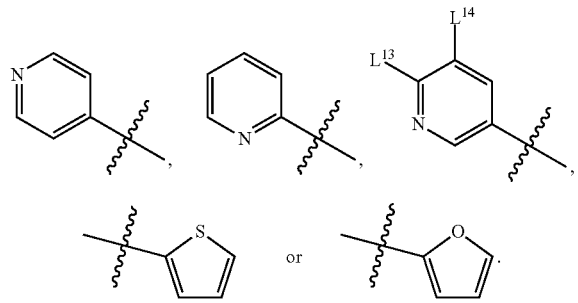
M³ may be selected from:
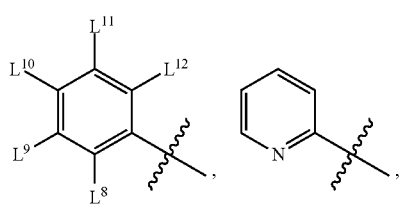
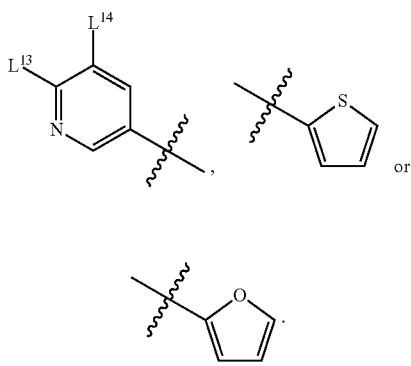
M³ may be selected from:
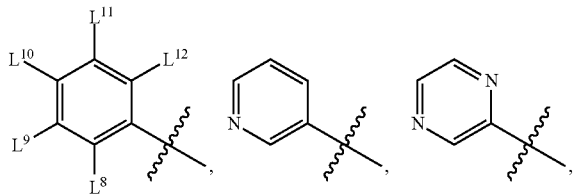
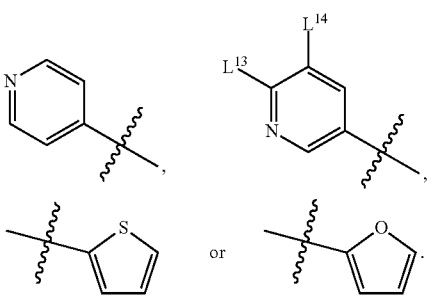
M³ may be selected from:
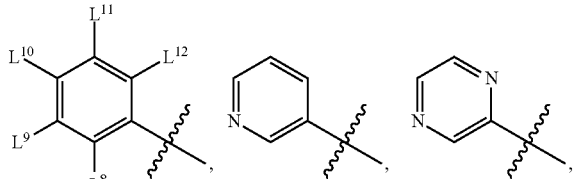
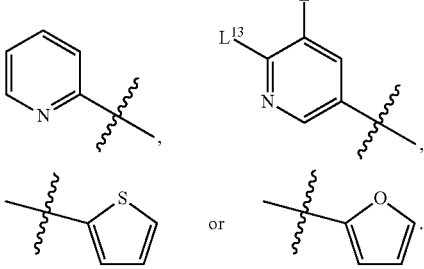

M³ may be selected from:

[structures: substituted phenyl with L⁸–L¹², pyridin-3-yl, pyridin-4-yl]

[structures: pyridin-2-yl, pyridine with L¹³,L¹⁴, thiophen-2-yl, furan-2-yl] or

M³ may be selected from:

[structures: substituted phenyl with L⁸–L¹², pyrazinyl, pyridin-4-yl]

[structures: pyridin-2-yl, pyridine with L¹³,L¹⁴, thiophen-2-yl, furan-2-yl] or

M³ may be selected from:

[structures: substituted phenyl with L⁸–L¹², pyridin-3-yl, pyrazinyl, pyridin-4-yl, pyridin-2-yl, pyridine with L¹³,L¹⁴, or thiophen-2-yl]

M³ may be selected from:

[structures: substituted phenyl with L⁸–L¹², pyridine with L¹³,L¹⁴]  or $E^8$ may be H, $CH_3$, F, Cl, Br, or $CF_3$. $E^9$ may be H, $CH_3$, F, Cl, Br, or $CF_3$. $E^{10}$ may be H, $CH_3$, F, Cl, Br, or $CF_3$. $E^{11}$ may be H, $CH_3$, F, Cl, Br, or $CF_3$. $E^{12}$ may be H, $CH_3$, F, Cl, Br, or $CF_3$. $E^{13}$ may be H, $CH_3$, F, Cl, Br, or $CF_3$. $E^{14}$ may be H, $CH_3$, F, Cl, Br, or $CF_3$. $L^8$ may be H, $CH_3$, $CH_2CH_3$, F, Cl, Br, $CF_3$, $OCF_3$, $OCF_2$, $S(=O)_2(NH_2)$ or $OCH_2C(CH_3)(CH_2)$. $L^9$ may be H, $CH_3$, $CH_2CH_3$, F, Cl, Br, $CF_3$, $OCF_3$, $OCF_2$, $S(=O)_2(NH_2)$ or $OCH_2C(CH_3)(CH_2)$. $L^{10}$ may be H, $CH_3$, $CH_2CH_3$, F, Cl, Br, $CF_3$, $OCF_3$, $OCF_2$, $S(=O)_2(NH_2)$ or $OCH_2C(CH_3)(CH_2)$. $L^{11}$ may be H, $CH_3$, $CH_2CH_3$, F, Cl, Br, $CF_3$, $OCF_3$, $OCF_2$, $S(=O)_2(NH_2)$ or $OCH_2C(CH_3)(CH_2)$. $L^{12}$ may be H, $CH_3$, $CH_2CH_3$, F, Cl, Br, $CF_3$, $OCF_3$, $OCF_2$, $S(=O)_2(NH_2)$ or $OCH_2C(CH_3)(CH_2)$. $L^{13}$ may be H, $CH_3$, F, Cl, Br, or $CF_3$. $L^{14}$ may be H, $CH_3$, F, Cl, Br, or $CF_3$.

The compound may be selected from one or more of:

[structure: 2-thioxothiazolidin-4-one with 5-(2-(trifluoromethyl)benzylidene)];

[structure: 3-methyl-2-thioxo-5-(3-(furan-2-yl)allylidene)thiazolidin-4-one]; and

[structure: 3-(3-hydroxyphenyl)-2-thioxo-5-(thiophen-2-ylmethylene)thiazolidin-4-one].

In a further embodiment there is provided a compound having the structure

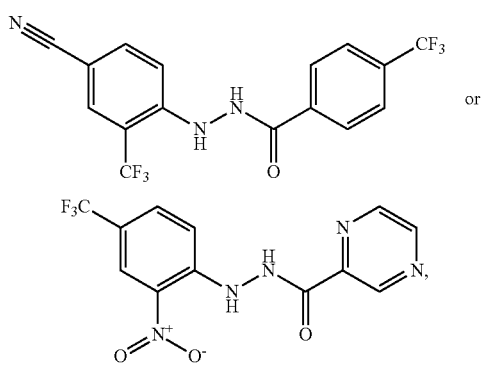

or

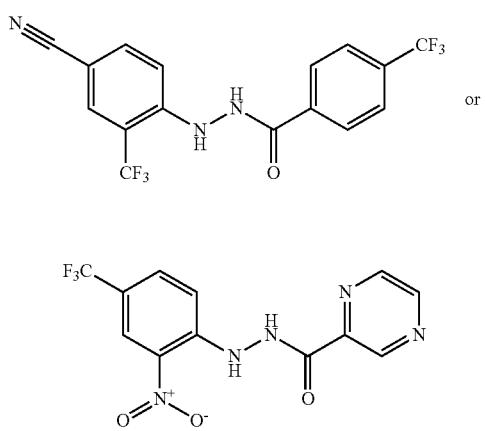

for use in the treatment of cancer.

In a further embodiment there is provided a pharmaceutical composition for treating cancer, including a compound having the structure

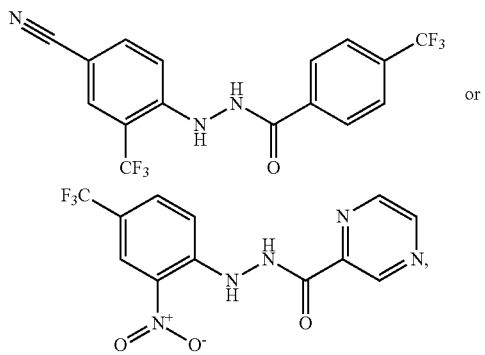

and a pharmaceutically acceptable carrier.

In a further embodiment there is provided a use of compound having the structure

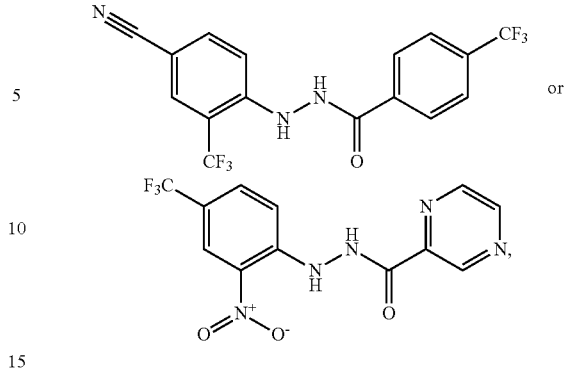

for treating cancer.

In a further embodiment there is provided a use of compound having the structure for treating cancer.

The cancer may be selected from one or more of the following: prostate cancer; breast cancer; colon cancer; cervical cancer; small-cell lung carcinoma; neuroblastomas; osteosarcoma; glioblastoma; melanoma; and myeloid leukaemia.

In accordance with another embodiment, there is provided a compound as described herein for use in the treatment of cancer.

In accordance with another embodiment, there is provided a pharmaceutical composition for treating cancer, comprising compound as described herein and a pharmaceutically acceptable carrier.

The pharmaceutical composition of claim 12, wherein the cancer is selected from one or more of the following: prostate cancer; breast cancer; colon cancer; cervical cancer; small-cell lung carcinoma; neuroblastomas; osteosarcoma; glioblastoma; melanoma; and myeloid leukaemia.

In accordance with another embodiment, there is provided a use of compound described herein for treating cancer.

In accordance with another embodiment, there is provided a use of compound described herein for the manufacture of a medicament for treating cancer.

In accordance with another embodiment, there is provided a commercial package comprising (a) compound as described herein and a pharmaceutically acceptable carrier; and (b) instructions for the use thereof for treating cancer.

In accordance with another embodiment, there is provided a commercial package comprising (a) a pharmaceutical composition comprising compound described herein and a pharmaceutically acceptable carrier; and (b) instructions for the use thereof for treating cancer.

In accordance with another embodiment, there is provided a compound of any one of Formulas I-IV, provided that the compound excludes all of the compounds set out in TABLES 3 and 4.

The cancer may be one or more of the following: prostate cancer; breast cancer; colon cancer; cervical cancer; small-cell lung carcinoma; neuroblastomas; osteosarcoma; glioblastoma; melanoma; and myeloid leukaemia. The cancer may be prostate cancer.

Alternatively, the compounds of TABLE 5 may be used for treating cancer, or may be combined with a pharmaceutically acceptable carrier for the treatment of cancer. The cancer may be selected from one or more of the following: prostate cancer; breast cancer; colon cancer; cervical cancer; small-cell lung carcinoma; neuroblastomas; osteosarcoma; glioblastoma; melanoma; and myeloid leukaemia.

BRIEF DESCRIPTION OF THE DRAWINGS

FIGS. 2A-2C show (A) dose response effect of selected hits in LNCaP PCa cells on the transcriptional activity of c-Myc by using a c-myc mediated luciferase reporter as compared to literature inhibitors 10058-F4 and 10074-G5 used as positive controls, with the data presented as mean±SEM of triplicates and expressed as a percentage of luciferase activity relative to DMSO control; (B) inhibition of Myc-Max reduces the levels of AR variant 7 in 22rv1 cells; and (C) the effect of VPC-70063 and VPC-70067 in comparison with 10058-F4 and 10074-G5 on cell viability of Myc positive (LNCaP) and Myc negative (HO15.19) cell lines, where the percent of cell viability is plotted in dose dependent manner. Data points represent the mean±95% CI (confidence interval) of triplicates and expressed as percent of cell viability relative to DMSO control.

FIGS. 3A-3E show (A) inhibition of Myc with VPC-70067 and VPC-70063 resulted in apoptosis of LNCaP cells as indicated by cleavage of PARP in Western blot; (B) purification of GST-Myc and His-Max using size exclusion chromatography, where the fraction highlighted with a black rectangle on the Western blot corresponds to the fraction used for the binding assay; (C) inhibition of Myc-Max interaction with the biotinylated E-box quantified by bilayer interferometry (BLI) in presence of 500 μM of the studied compounds; (D) dose response inhibition of Myc-Max binding to DNA in presence of best compound VPC-70063; and (E) mammalian 2-hybrid assay showing the effect of inhibitors on the interaction between Myc and Max, with data points represent the mean±SEM of at least three independent experiments. $P<0.05$ (*), $P<0.01$ () and $P<0.001$ (*) were considered statistically significant compared with vehicle control (two-tailed t-test).

DETAILED DESCRIPTION

Figure 1A:
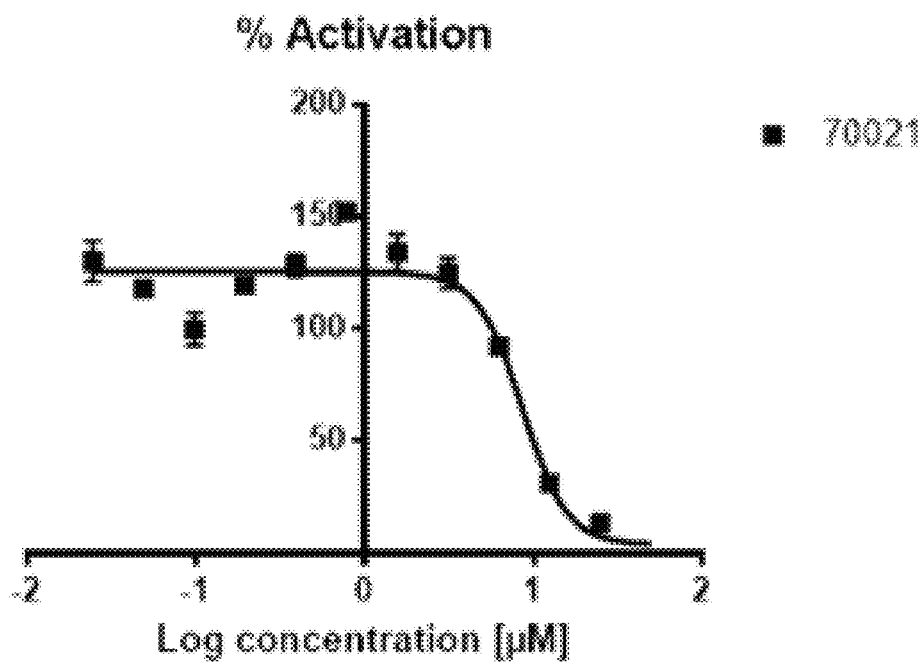
FIGS. 1A-1B show (A) a the $IC_{50}$ of 8.5 µM for VPC-70021 using the Cignal c-Myc kit using a range of concentrations from 24 nM to 50 μM; and (B) the effect of VPC-70021 on growth of LNCaP cells stimulated with androgen; PC3 cells; HL60 cells and; PC12 cells (Max negative).
Figure 1B:
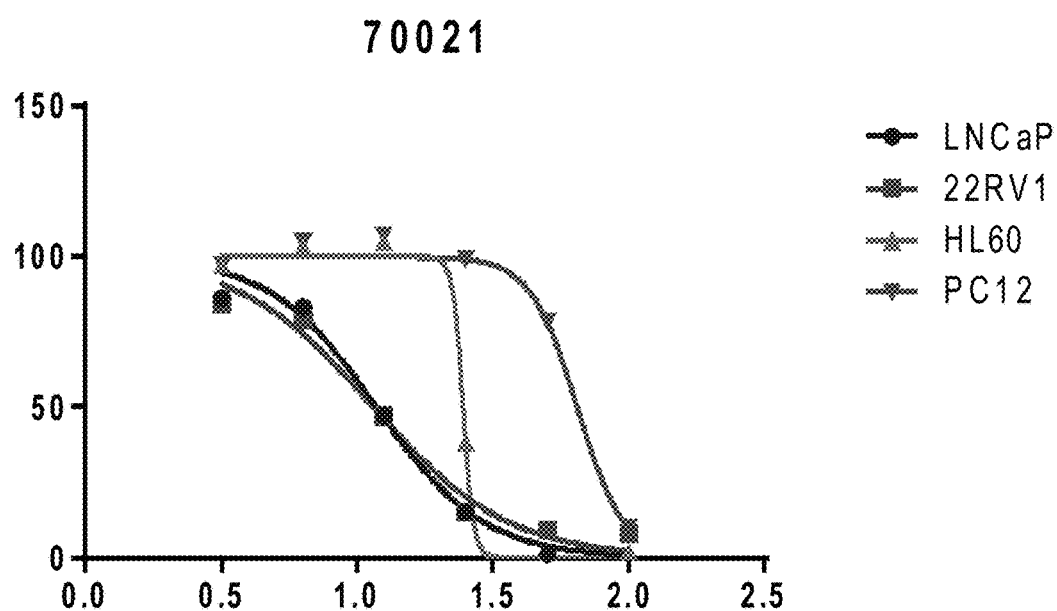

The following detailed description will be better understood when read in conjunction with the appended figures. For the purpose of illustrating the invention, the figures demonstrate embodiments of the present invention. However, the invention is not limited to the precise arrangements, examples, and instrumentalities shown.

Any terms not directly defined herein shall be understood to have the meanings commonly associated with them as understood within the art of the invention.

The Myc-Max complex is an attractive target for direct inhibition. In silico computational drug discovery methods were used to conduct a virtual screen of more than 6 million purchasable compounds from the ZINC database (Irwin, J. et al. Abstracts of Papers Am. Chem. Soc. (2005) 230: U1009) to identify potential Myc-Max complex binders. The in silico methods included large-scale docking, in-site rescoring and consensus voting procedures.

It will be understood by a person of skill that COOH and NR2 may include the corresponding ions, for example carboxylate ions and ammonium ions, respectively. Alternatively, where the ions are shown, a person of skill in the art will appreciate that the counter ion may also be present.

Those skilled in the art will appreciate that the point of covalent attachment of the moiety to the compounds as described herein may be, for example, and without limitation, cleaved under specified conditions. Specified conditions may include, for example, and without limitation, in vivo enzymatic or non-enzymatic means. Cleavage of the moiety may occur, for example, and without limitation, spontaneously, or it may be catalyzed, induced by another agent, or a change in a physical parameter or environmental parameter, for example, an enzyme, light, acid, temperature or pH. The moiety may be, for example, and without limitation, a protecting group that acts to mask a functional group, a group that acts as a substrate for one or more active or passive transport mechanisms, or a group that acts to impart or enhance a property of the compound, for example, solubility, bioavailability or localization.

In some embodiments, compounds of Formulas I-IV, as described herein, may be used for systemic treatment of at least one indication selected from the group consisting of: prostate cancer, breast cancer, ovarian cancer, endometrial cancer, hair loss, acne, hirsutism, ovarian cysts, polycystic ovary disease, precocious puberty and age related macular degeneration. Alternatively, the compounds of Formulas I-IV may be used for systemic treatment of at least one indication selected from the group consisting of: prostate cancer; breast cancer; colon cancer; cervical cancer; small-cell lung carcinoma; neuroblastomas; osteosarcoma; glioblastoma; melanoma; and myeloid leukaemia. the In some embodiments, compounds of Formulas I-IV may be used in the preparation of a medicament or a composition for systemic treatment of an indication described herein. In some embodiments, methods of systemically treating any of the indications described herein are also provided.

Compounds as described herein may be in the free form or in the form of a salt thereof. In some embodiment, compounds as described herein may be in the form of a pharmaceutically acceptable salt, which are known in the art (Berge S. M. et al., J. Pharm. Sci. (1977) 66(1):1-19). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g., free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g., free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g., free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formulas illustrated for the sake of convenience.

In some embodiments, pharmaceutical compositions as described herein may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents (used interchangeably herein) are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in Remington: the Science & Practice of Pharmacy by Alfonso Gennaro, 20th ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene polyoxypropylene copolymers may be used to control the release of the compounds. Other potentially useful parenteral delivery systems for modulatory compounds include ethylene vinyl acetate copolymer particles, osmotic pumps, implantable infusion systems, and liposomes. Formulations for inhalation may contain excipients, for example, lactose, or may be aqueous solutions containing, for example, polyoxyethylene 9 lauryl ether, glycocholate and deoxycholate, or may be oily solutions for administration in the form of nasal drops, or as a gel.

Compounds or pharmaceutical compositions as described herein or for use as described herein may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition as described herein includes a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to an androgen independent form. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, compounds and all different forms thereof as described herein may be used, for example, and without limitation, in combination with other treatment methods for at least one indication selected from the group consisting of: prostate cancer, breast cancer, ovarian cancer, endometrial cancer, hair loss, acne, hirsutism, ovarian cysts, polycystic ovary disease, precocious puberty and age related macular degeneration. Alternatively, the compounds described herein may be useful for the treatment of one or more of the following: prostate cancer; breast cancer; colon cancer; cervical cancer; small-cell lung carcinoma; neuroblastomas; osteosarcoma; glioblastoma; melanoma; and myeloid leukaemia. For example, compounds and all their different forms as described herein may be used as neoadjuvant (prior), adjunctive (during), and/or adjuvant (after) therapy with surgery, radiation (brachytherapy or external beam), or other therapies (for example, HIFU).

In general, compounds as described herein should be used without causing substantial toxicity. Toxicity of the compounds as described herein can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be appropriate to administer substantial excesses of the compositions. Some compounds as described herein may be toxic at some concentrations. Titration studies may be used to determine toxic and non-toxic concentrations. Toxicity may be evaluated by examining a particular compound's or composition's specificity across cell lines using PC3 cells as a negative control that do not express AR. Animal studies may be used to provide an indication if the compound has any effects on other tissues. Systemic therapy that targets the AR will not likely cause major problems to other tissues since anti-androgens and androgen insensitivity syndrome are not fatal.

Compounds as described herein may be administered to a subject. As used herein, a "subject" may be a human, non human primate, rat, mouse, cow, horse, pig, sheep, goat, dog, cat, etc. The subject may be suspected of having or at risk for having a cancer, such as prostate cancer, breast cancer, ovarian cancer or endometrial cancer, or suspected of having or at risk for having acne, hirsutism, alopecia, benign prostatic hyperplasia, ovarian cysts, polycystic ovary disease, precocious puberty, or age related macular degeneration. Diagnostic methods for various cancers, such as prostate cancer, breast cancer, ovarian cancer or endometrial cancer, and diagnostic methods for acne, hirsutism, alopecia, benign prostatic hyperplasia, ovarian cysts, polycystic ovary disease, precocious puberty, or age related macular degeneration and the clinical delineation of cancer, such as prostate cancer, breast cancer, ovarian cancer or endometrial cancer, diagnoses and the clinical delineation of acne, hirsutism, alopecia, benign prostatic hyperplasia, ovarian cysts, polycystic ovary disease, precocious puberty, or age related macular degeneration are known to those of ordinary skill in the art.

Various alternative embodiments and examples are described herein. These embodiments and examples are illustrative and should not be construed as limiting the scope of the invention.

Materials and Methods

Virtual Screening of Potential Myc-Max DBD Inhibitors.

The published 1.9 Å crystal structure of c-Myc-Max heterodimer bound to its DNA-recognition sequence (PDB ID:1NKP [34], chains A, B; waters and DNA excluded) was subjected to the Site Finder algorithm implemented in MOE [51]. Site Finder is a geometric method which uses alpha spheres (virtual atoms) to probe a protein surface for suitable small molecule binding pockets. Briefly, Site Finder first identifies regions of tight atomic packing, filters out highly solvent exposed sites, calculates alpha spheres on sites and classifies them as either hydrophobic or hydrophilic depending on whether the virtual atom is in a good hydrogen bonding spot in the receptor, and then produces a collection of sites based on pruning (alpha spheres corresponding to inaccessible regions or exposed to solvent are eliminated) and clustering (by number and chemical type) of alpha spheres. The sites are then ranked according to their Propensity for Ligand Binding (PLB) score. The top PDB-ranked pocket was used for subsequent in silico screening. Virtual screening of the ZINC12 database [53, 54] was performed using structure-based methods including molecular docking algorithms and pharmacophore screening. The Glide™ program [55, 56], part of Maestro 9.3™ suite, Schrödinger LLC™ [57], was used as the starting point to perform rigid docking of 4.7 million drug-like chemicals. Following Maestro's standard protein preparation protocol [87, 88], applied to the Myc-Max X-ray structure, a docking grid was defined as a 20 Å box centered on the residues of predicted Myc-Max DBD binding site for Glide sampling and scoring of screening compounds. Prior to docking, each chemical was washed and energy-minimized under the MMFF94x force field and Born solvation as per ligand preparation protocol implemented in MOE [51]. Docking was conducted using Glide standard precision mode with all other settings set to default. The generated docking poses were ranked by the Glide score, an interaction energy score that includes hydrogen bonding and hydrophobic interactions contributions. Potentially weak binders (Glide score>−5.5 kcal/mol) were discarded. The remaining top-ranked 12503 remaining compounds were further filtered by structure-based pharmacophore screening using MOE's tools [51]. A pharmacophore model of two essential hydrophobic features (1.5 Å diameter each) of the binding site (formed primarily by Leu917, Ile218, Phe921 and Phe222) was built and used to search for matching hits in the database of top ranked Glide poses. 1019 pharmacophore-matching hits were then selected for manual inspection using the 3D visual environment in MOE. 69 compounds having a good balance of Glide docking score and ligand efficiency and making favorable interactions with the surrounding side chains in the pocket were purchased for subsequent experimental testing.

Cell Culture and Reagents

LNCaP and PC3 cells were purchased from the ATCC and grown in RPMI 1640 supplemented with 10% fetal bovine serum (FBS). HO15.19 cells were a generous gift from John Sidivy at Brown University and were cultured in Dulbecco's modified Eagle's medium DMEM (ATCC 30-2002) supplemented with 10% FBS. 10058-F4 and 10074-G5 were obtained from Sigma™. The UBE2C reporter plasmid was purchased from GeneCopoeia (product ID #HPRM16429). The Biolux Gaussia™ luciferase assay kit was purchased from New England Biolab™ (#E3300L). PrestoBlue™ cell viability reagent was purchased from Invitrogen™ (#A-13262).

Transfection and Reporter Assays

Cell transfection was performed using TransIT-2020™ transfection reagents according to the manufacturer's instructions (Mirus™). LNCaP cells were plated at 10000 cells per well and treated for 1 day with the indicated concentration of compound. Myc reporter activity was measured using the Cignal Myc Reporter Assay Kit™ from Qiagen™ (#336841) according to the manufacturer's instructions. For the UBE2C reporter assay, 22rv1 cells were plated at 10000 cells per well in 96-well plates in RPMI media supplemented with 5% charcoal-stripped serum (CSS) and treated for 1 day with 1 µM, 10 µM and 25 µM of compound.

Cell Viability Assays

LNCaP were plated at 5000 cells per well in RPMI 1640 containing 5% CSS in a 96-well plate, treated with test compounds (0-25 µM) for 96 hours. Cell density was measured using the PrestoBlue™ assay according to the manufacturer's protocol. The percentage of cell survival was normalized to the cell density of control wells treated by vehicle. Viability of Myc-negative 14015.19 cells was done similarly but in DMEM supplemented with 5% CSS.

c-Myc-Max Purification

Histidine tagged Max (residues 23-102) and GST tagged Myc (residues 368-454) were overexpressed in *E. coli* BL21-DE3 cells. Cells were co-lyzed in lysis buffer (20 mM Tris pH 8, 500 mM NaCl, 5% glycerol, 10 mM imidazole, 8 mM BME, 2.1 mM PMSF). After sonication and centrifugation, the complex was first purified by using a Ni-NTA affinity resin. After overnight dialysis to remove the imidazole, the protein sample was applied to a size exclusion chromatography equilibrated with (20 mM Tris pH 8, 150 mM NaCl, 5% glycerol, 0.2 mM TCEP). Fractions containing equal amount of Myc and Max on SDS PAGE were collected and used for the binding assay. The presence of both proteins was validated by Western blot using a specific antibody of each protein (Max (h2) Sc-8011 and c-Myc (9E10) Sc-40, Santa Cruz Biotechnology™)

Biolayer Interferometry Assay

The direct interaction between biotinylated E-box oligo (TGAAGCAGACCACGTGGTCGTCTTCA) immobilized on a streptavidin biosensor and a purified Myc-Max complex (0.05 mg/ml) was quantified by BLI using OctetRED (ForteBio™). The DNA was first bound to the super-streptavidin sensors over 1000 sec at 25° C. The sensors were next moved into wells containing the reaction buffer (20 mM Tris pH 8, 150 mM NaCl, 5% glycerol, 0.2 mM TCEP, 5% dimethylsulfoxide) for measuring the baseline and next into the Myc-Max complex alone or in presence of the tested inhibitors to study the association of the complex to the DNA.

Western Blotting

After 48 hours of treatment with Myc compounds, LNCaP cells were lysed, and protein sample preparation followed by Western blotting were performed. Blots were incubated with primary antibodies against c-Myc, PARP (Sigma™ 084M4766V), PARP cleaved-Asp214 (Sigma™ SAB4500487) and β-Actin (Sigma™ A2066) overnight at 4° C., followed by appropriate peroxidase-conjugated secondary antibodies. β-actin served as an internal control. Visualization of the immunocomplexes was done by an enhanced chemiluminescence detection system (Millipore™) followed by exposure to X-ray films.

Mammalian Two-Hybrid Assay

Full lengths Myc and Max were cloned in pBIND and pACT plasmids (CheckMate™, Promega™), respectively. PC3 cells in RPMI 1640 supplemented with 5% FBS were seeded in 96-well plates at 5,000 cells/well. After 24 hours, cells were transfected with 15 ng of pACT-Max, 19.5 ng of pBIND-Myc, and 13.6 ng of the reporter plasmid PG5-luciferase. After 24 hours, cells were treated with various concentrations of the tested inhibitors. Cells were lysed the next day, and the luminescence signal was measured after adding 50 µL of luciferase assay reagent (Promega™). Each measurement was done in 4 replicates with biological replicates of 3. Luciferase levels corresponding to Myc-Max interactions were measured and normalized to a control provided by the commercial kit to discard non-specific effect due to toxicity or direct luciferase inhibition.

Microsomal (Half-Life) Stability

For the metabolic (half-life) stability assay, microsomes (MLM) were incubated with 100 µM of test compound at 37° C. in the presence of the co-factor, NADPH, which initiates the reaction. For each MLM mix we prepare a series of 4 tubes (t=0, t=10 min, t=20 min, t=45 min) to monitor the disappearance of test compounds over a 45 minute time period. The reaction is stopped at specific time points using 300 µl stopping buffer (Acetonitrile+0.05% formic acid with internal standard (150 ng/ml d3T)). Following centrifugation, the supernatant is analyzed on the LC-MS/MS.

EXAMPLES

Example 1: In Silico Identification of Hit Compounds Targeting the Myc-Max DBD Site The drug-like subset of the ZINC12 molecular database [53, 54], containing more than 6 million purchasable chemicals, was further reduced to 4.7 million compounds by filtering by physicochemical properties such as charge, number of rings and rotatable bonds. The resulting set of 4.7 million structures was virtually screened against the identified pocket on the Myc-Max dimer DBD. Glide™ (Maestro 9.3™ suite, Schrödinger LLC™) software [55-57] was employed as the primary structure-based docking technique (with the standard precision mode). The generated docking poses were then filtered by the Glide™ docking score (binding energy score used to rank docking poses and distinguish strong binders in their optimal placement in the respective pocket from compounds that bind weakly) using a −5.5 kcal/mol cutoff. The top ranked 12503 remaining compounds were further filtered by structure-based pharmacophore screening using MOE's tools. A pharmacophore model of two essential hydrophobic features (1.5 Å diameter each) of the binding site (formed primarily by Leu917, Ile218, Phe921 and Phe222) was built and used to search for matching hits in the database of top ranked Glide™ poses. 1019 pharmacophore-matching hits were then selected for visual inspection and 116 compounds having a good balance of Glide™ docking score and ligand efficiency (the ratio of binding affinity over the number of heavy atoms) made additional side-chain or backbone hydrogen bonds with the charged residues in the site. Sixty nine (69) compounds were selected for purchase, in particular those predicted to form hydrogen bonds with the backbone carbonyl oxygen of Arg215. The purchased compounds were then subjected to rapid evaluation using a primary screening transcriptional assay as described below. From the primary cell-based screening 10 hits were identified (TABLE 1) showing better than 50% inhibition of Myc-Max transcriptional activity. Hits with more than 70% inhibition were further investigated for effect on the downstream pathway using UBE2C reporter assay.

TABLE 1

Docking scores and activities of hit compounds that bind the ordered Myc-Max DBD at the identified site.

| Compound ID | Structure | Glide docking score (kcal/mol) | Myc-Max transcriptional activity % inhibition (25 μM) | Myc-Max/UBE2C downstream pathway % inhibition (25 μM) |
|---|---|---|---|---|
| VPC-70005 | 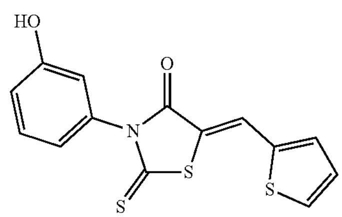 [SMILES: O=C1/C(=C/c2cccs2)SC(=S)N1c1cccc(O)c1] | −5.53 | 65 | n/a |
| VPC-70021 | 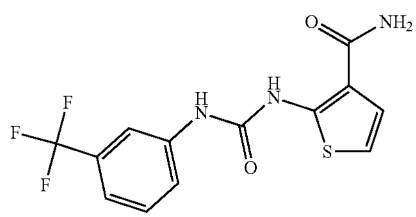 [SMILES: NC(=O)c1ccsc1NC(=O)Nc1cccc(C(F)(F)F)c1] | −5.63 | 95 | 73 |
| VPC-70027 | 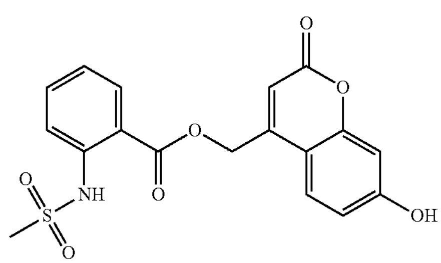 [SMILES: CS(=O)(=O)Nc1ccccc1C(=O)OCc1cc(=O)oc2cc(O)ccc12] | −5.69 | 53 | n/a |
| VPC-70033 | 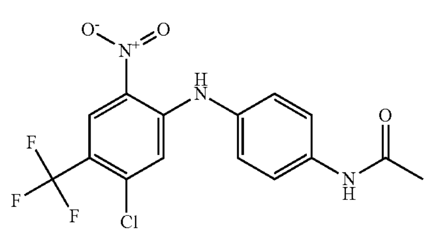 [SMILES: CC(=O)Nc1ccc(Nc2cc(Cl)c(C(F)(F)F)cc2[N+](=O)[O-])cc1] | −5.77 | 81 | 51 |

TABLE 1-continued

Docking scores and activities of hit compounds that bind the ordered Myc-Max DBD at the identified site.

| Compound ID | Structure | Glide docking score (kcal/mol) | Myc-Max transcriptional activity % inhibition (25 μM) | Myc-Max/UBE2C downstream pathway % inhibition (25 μM) |
|---|---|---|---|---|
| VPC-70053 | 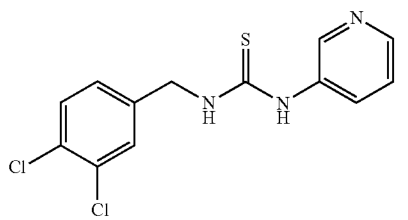 [SMILES: S=C(NCc1ccc(Cl)c(Cl)c1)Nc1cccnc1] | −5.66 | 73 | 50 |
| VPC-70063 | 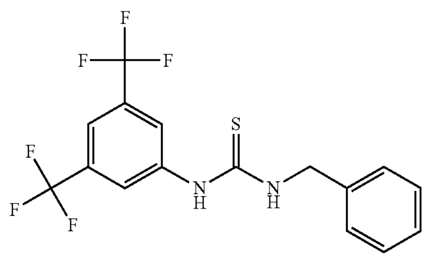 [SMILES: FC(F)(F)c1cc(NC(=S)NCc2ccccc2)cc(C(F)(F)F)c1] | −5.51 | 106 | 94 |
| VPC-70064 | 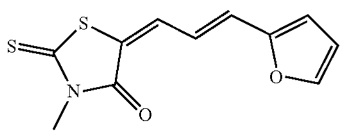 [SMILES: CN1C(=O)/C(=C\C=C\c2ccco2)SC1=S] | −5.59 | 78 | 64 |
| VPC-70066 | 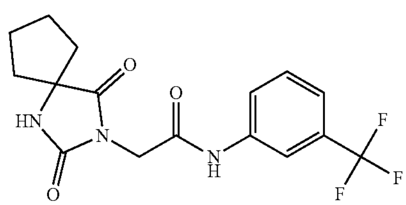 [SMILES: O=C(CN1C(=O)NC2(CCCC2)C1=O)Nc1cccc(C(F)(F)F)c1] | −5.77 | 65 | n/a |
| VPC-70067 | 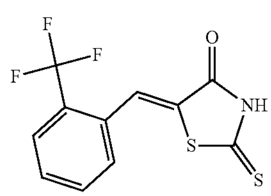 [SMILES: O=C1NC(=S)S/C1=C\c1ccccc1C(F)(F)F] | −5.67 | 98 | 71 |
| VPC-70068 | 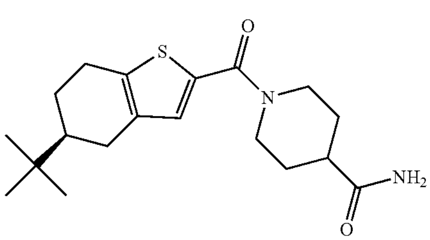 [SMILES: CC(C)(C)[C@H]1CCc2sc(C(=O)N3CCC(C(N)=O)CC3)cc2C1] | −5.68 | 73 | 58 |

TABLE 1-continued

Docking scores and activities of hit compounds that bind the ordered Myc-Max DBD at the identified site.

| Compound ID | Structure | Glide docking score (kcal/mol) | Myc-Max transcriptional activity % inhibition (25 μM) | Myc-Max/UBE2C downstream pathway % inhibition (25 μM) |
|---|---|---|---|---|
| 10058-F4 | (structure) | n/a | 91 | 70 |
| 10074-G5 | (structure) | n/a | 88 | n/a |

Example 2: Effects of Hit Compounds on Myc-Max Transcriptional Activity

Compounds were subjected to experimental evaluation using the commercially available transcriptional assay Cignal c-Myc luciferase reporter assay in LNCaP cells. Compounds 10058-F4 and 10074-G5, known Myc inhibitors from the literature, were used as positive controls. A transiently transfected Myc-driven luciferase reporter allowed the monitoring of Myc-regulated signal in LNCaP upon treatment with the in silico identified compounds. From a larger number of hits, 10 compounds caused more than 50% reduction of the Myc-driven luciferase levels at 25 μM (see TABLE 1). A thorough dose response analysis was performed using LNCaP cells to evaluate the potency of hit compounds. The compounds inhibit Myc-Max transcriptional activity with low to mid-micromolar potency, with the following IC50 values (half-maximal inhibitory concentration with 95% Confidence Intervals) established as: 22.7 μM [16.6 to 31.2 μM] for VPC-70067 comparable to that of the control compound 10058-F4 (28.9 μM; [19.7 to 42.5 μM]), and 8.9 μM [6.6 to 11.8 μM] for VPC-70063 (FIG. 2A).

Example 3: Effects of Hit Compounds on Myc-Max Downstream-Regulated Pathways Myc inhibition was recently reported to reduce levels of the constitutively active androgen receptor splice variant AR-V7 in 22rv1 cells [20]. AR-V7 has been shown to specifically regulate the expression level of the Ubiquitin Conjugating Enzyme E2C (UBE2C) in androgen-deprived 22rv1, through the UBE2C promoter [21]. Hence, a complementary transcriptional screening assay was developed in house to monitor the expression levels of the AR-V7 isoform in 22rv1 cells by using a plasmid containing a UBE2C promoter linked to a luciferase reporter. The dose-dependent reduction of luciferase levels by the identified hits indicates a Myc-related reduction of AR-V7 level in the cells (see TABLE 1). Compound VPC-70063 showed the highest reduction of UBE2C promotor activity suggesting the reduction of V7 levels in 22rv1. The AR-V7 reduction with the hits was confirmed by Western blot (FIG. 2B).

Example 4: Effects of Hit Compounds on Cell Viability

The effect of hit compounds on Myc-driven cell proliferation was evaluated by measuring the cell viability of LNCaP cells after treatment with increasing concentrations of compounds. Again, VPC-70063 showed the best inhibition of LNCaP cell proliferation (IC50=2.5 μM; [95% CI: 2.1-2.8 μM]. To rule out that this inhibition was due to non-specific cytotoxicity of VPC-70063 we therefore treated the c-Myc knockout 11015.19 cell line (FIG. 2C) with this compound. The proliferation of the 11015.19 cell line was slightly affected by VPC-70063, up to a maximum of 40% inhibition at 25 μM. However, at a VPC-70063 concentration of 3 μM where 70% of LNCaP cells are inhibited there was no significant effect on the c-Myc knockout cells. VPC-70067, 10058-F4 and 10074-G5 have IC50 of 11.1 μM [95% CI: 10.6-11.4 μM], 18.31 μM [95% CI: 17.7-18.8 μM] and 8.7 μM [95% CI: 8.3-9.1 μM], respectively (FIG. 2C).

Example 5: Mechanism of Action of Hit Compounds

Apoptosis. Myc inhibition induces cell death by cell cycle arrest and apoptosis [58]. Cleavage of PARP-1 by caspases is considered a hallmark of apoptosis and so we measured the ability of compounds to induce PARP cleavage after treatment. As predicted, VPC-70063 and VPC-70067 were inducing PARP cleavage suggesting that the effect of these two compounds were through apoptotic pathways (FIG. 3A and TABLE 2).

Direct Binding and disruption of protein-DNA interaction. To study the direct effect of our hit compounds VPC-70063 and VPC-70067 on the interaction between Myc-Max heterodimer and the DNA, we used Bio-Layer Interferometry (BLI, ForteBio™). This technique is a label-free technology allowing the measurement of direct interactions between two partners, one immobilized on a sensor and the other one present in a solution. We applied this technology to study the disruption of the interaction between a biotinylated E-box oligo immobilized on a streptavidin biosensor and a purified Myc-Max complex in presence of our compounds. Therefore, histidine-tagged Max (residues 23-102) and GST tagged Myc (residues 368-454) were overexpressed and co-purified. The fraction containing equal amount of Myc and Max was collected and used for the binding assay (FIG. 3B). The presence of both proteins was validated by Western blot using a specific antibody of each protein. Using BLI, we were able to show that Myc-Max heterodimer was prevented from interacting with the immobilized DNA in presence of both VPC-70063 and VPC-70067 similarly to the control 10074-G5 (FIG. 3C and TABLE 2). Additionally, we tested the ability of our best compound VPC-70063 to disrupt the interaction of MYC/MAX with DNA in a dose dependent manner. At a concentration below 100 μM, we did not see any significant effect on the complex dissociation, but at higher concentration we noticed a dose response decrease of the MYC/MAX binding to DNA showing that VPC-70063 was able to disrupt the complex formation (FIG. 3D).

TABLE 2

Compound Testing Results

| Compound# | $IC_{50}$ (uM) | PARP effect | % inhibition Myc K.O cells (12 uM) | BLI binding |
|---|---|---|---|---|
| 70511 | 2 | | | |
| 70495 | 5 | | | |
| 70465 | 10 | | | |
| 70127 | 1 | strong | 19 | weak |
| 70084 | 20 | weak | | |
| 70021 | 10 | nil | 0 | average |
| 70388 | 20 | | | |
| 70381 | 20 | | | |
| 70413 | 15 | weak | | weak |
| 70395 | >25 | | | |
| 70314 | 15 | | | |
| 70327 | >25 | | | |
| 70346 | >25 | | | |
| 70390 | 9 | | | |
| 70219 | >25 | | | |
| 70277 | >25 | | | |
| 70223 | 10 | | 40 | |
| 70215 | 20 | weak | 29 | |
| 70033 | 10 | nil | | weak |
| 70053 | 11 | | | |
| 70067 | 22 | good | 3 | strong |
| 70063 | 9 | strong | 35 | strong |
| 70005 | >25 | | | |
| 70068 | | average | | |

Example 6: Effect of Inhibitors on Myc-Max Interaction Using Mammalian 2-Hybrid Assay The effect of inhibitors of Myc-Max interaction was studied by using a mammalian two hybrid assay. Full lengths Myc and Max were cloned in pBIND and pACT plasmids (CheckMate™, Promega™), respectively. Luciferase levels corresponding to Myc-Max interactions were measured and normalized to a control provided by the commercial kit to discard non-specific effect due to toxicity or direct luciferase inhibition. VPC-70063 showed a dose response inhibition of the interaction between the two proteins (FIG. 3E). Unexpectedly, 10074-G5 did not show any effect on Myc-Max interaction in this assay. As VPC-70063 is more potent than 10074-G5 in most of the other assays, higher concentrations of the latter may be needed to see an inhibition of the interaction.

Example 7: In Silico Binding Mode of VPC-70063

As described above, compound VPC-70063 was the best performer in all the cell-based and cell-free assays designed for this study. The predicted binding pose of VPC-70063 (1-benzyl-3-(3,5-bis(trifluoromethyl)phenyl)thiourea), obtained using computational modeling methods. The chemical structure of VPC-70063 is composed of a benzyl ring at one end, a thiourea linker and a highly hydrophobic 3,5-bis(trifluoromethyl)phenyl moiety at the other end. Within the binding pocket of the Myc-Max DBD domain, VPC-70063 is predicted to form 2 hydrogen bonds between the 2 thiourea amine hydrogens and the backbone carbonyl of Arg215, as well as a large number of strong hydrophobic interactions formed by the 3,5-bis(trifluoromethyl)phenyl moiety with the hydrophobic core of the pocket, including aliphatic and aromatic side-chains of Leu917, Phe921, and Lys939 of Myc, and Ile218, Phe222, and Arg215 of Max, and those formed by the benzyl ring with aliphatic side chains of Arg215 and Arg212 of Max. The 3,5-bis(trifluoromethyl)phenyl group of VPC-70063 is matching the hydrophobic features of the constructed pharmacophore, it is deeply buried in the hydrophobic core of the Myc-Max DBD pocket being stabilized via hydrophobic interactions. Furthermore, in the binding pose, the benzyl ring of VPC-70063 is predicted to overlap significantly with the DNA backbone. Therefore, it was expected that VPC-70063, in as much as other hits having similar interactions, would overcome the binding of DNA to the Myc-Max DBD site. It is not surprising then, that VPC-70063 blocks the binding of Myc-Max to DNA as determined by BLI measurements. Further experiments are required to unequivocally prove the binding mode and direct disruption of protein-DNA interactions with our current hits and future derivatives.

Findings reported in this study prompted us to leverage the full power of our in silico drug discovery platform that proved successful in targeting unconventional sites on protein surfaces and in yielding promising preclinical drug candidates for previously uncharted targets [59-67]. Consequently, we have initiated ligand-based similarity searches followed by molecular docking and consensus scoring computations to identify analogs of the initial hit compounds. Briefly, three-dimensional similarity searches were conducted utilizing the ROCS program from OpenEye™ [68, 69] against a large ensemble of conformers consisting of at most 200 conformers for each of the approximately 9 million entries of the drug-like purchasable chemical space of the ZINC15 database [70]. Conformers are generated using Omega2 of OpenEye™ [71]. Current hits are used as query molecules. ROCS is a fast shape-based superposition method, which uses a combination of global three-dimensional shape overlay and color-based chemical complementarity in terms of hydrogen-bond donors, hydrogen-bond acceptors, hydrophobes, anions, cations and rings, to compare the query to a large collection of molecules and rank the matching hitlist according to the TanimotoCombo score, a rigorous measure of shape and color overlap. Molecular docking, using 3 docking programs differing in their underlying scoring functions and sampling algorithms: Glide [55, 56], ICM [72] and Hybrid [73, 74], is employed to position analogs into the Myc-Max DBD. Consensus voting and filtering using various thresholds is subsequently performed. The consensus is built based on top-ranking docking scores (the more negative the stronger the binding affinity; e.g. Glide score≤−5.5 kcal/mol) and calculation, using MOE scripts [75, 76], of two indicators: root mean square deviation (RMSD), an atom-based metric reflecting the deviation in atomic coordinates between poses obtained from the three docking programs, and predicted pKi, a good indicator of potency. The filtering thresholds used are: RMSD≤3 Å (an RMSD of 0 indicates perfect superposition; the higher the RMSD the greater the deviation), and pKi≥5 (the larger more potent theoretically). All high-confidence analogs are subsequently subjected to full experimental profiling. Quantitative (QSAR) models based on our in house developed 3D and 4D inductive descriptors [77, 78] are currently customized for Myc-Max target to serve as an additional scoring function for accurate activity prediction of analogs and future derivative series.

In the longer term and as per our usual practices [79], the target affinity and drug-like profile of the most promising analogs will be optimized based on observed structure activity relationships (SAR) in iterative rounds of in silico modeling, medicinal chemistry and biological validation, until a lead is found. In this process, for more elaborate and accurate scoring, computationally-demanding classical molecular dynamics (MD) and free energy perturbation MD simulations [80-85] will be executed on GPU-accelerated clusters. Moreover, the drug-like profile of promising derivatives will be improved by eliminating toxic moieties and metabolically labile centers as predicted by SimulationsPlus ADMET Predictor software [86]. This approach will allow us to achieve highly potent binding while maintaining the ligand properties required for safety and biological efficacy.

In the absence of clinically approved anti-Myc drugs, targeting the Myc-Max complex represents a critical step towards creating new therapeutics for lethal CRPC and NEPC. In this study, we identified a possible druggable site on the DNA-binding domain (DBD) of the structurally ordered Myc-Max complex and employed a computer-aided rational drug discovery approach to identify small molecules that inhibit Myc-Max functionality. A large-scale virtual screening protocol was utilized to select a set of top-ranked compounds that were subsequently characterized experimentally. A number of compounds were identified that inhibit Myc-Max activity with low to mid-micromolar potency and with no or minimal cytotoxicity, including VPC-70067, a compound highly similar in structure, potency and mechanism of action to 10058-F4. In addition, a novel compound VPC-70063 with a chemically different scaffold was identified as the best performer in a panel of in vitro assays as it inhibits Myc-Max transcriptional activity (IC50=8.9 µM; [95% CI: 6.6 to 11.8 µM]), Myc-Max downstream functions, levels of the AR-V7 splice variant in CRPC cells, and cell growth in various PCa cell lines. In addition, VPC-70063 induces apoptosis as expected with a Myc inhibitor. Its specificity was confirmed by the inhibitory effect on the MYC/MAX association with DNA and on the cell viability of MYC negative HO15.19 where the inhibition due to some cytotoxicity occurred at much higher concentrations than the effect on MYC positive LNCaP cells. At the IC50 value of VPC-70063 (2.5 µM in LNCaP cells), the inhibition of Myc negative HO15.19 cells was ~7%. This cytotoxicity that is myc independent increased gradually with the increasing concentrations of the compound to reach 40% at 25 µM of VPC-70063. It is noteworthy to mention that the literature compound 10074-G5 also showed some cytotoxicity of 37% at 25 µM. Future work with chemoinformatics optimization will be performed to remove this undesirable effect from VPC-70063 while keeping its specific inhibition of Myc-Max complex. As before, our integrative approach to drug discovery proved successful insofar in discovering novel Myc-Max inhibitors as promising far-reaching therapeutics for advanced prostate and other cancers.

The compounds shown in TABLE 3 below represent those compounds tested falling under Formula I and having 70% or greater Myc-Max inhibitory activity. Similarly, the compounds shown in TABLE 4 below represent those compounds tested falling under Formula IV and having 65% or greater Myc-Max inhibitory activity. Lastly, the compounds shown in TABLE 5 below represent those compounds tested and having less than 70% Myc-Max inhibitory activity.

TABLE 3

FORMULA I STRUCTURES

| Compound # | Structure | ZINC # | % Inhibition | | | |
|---|---|---|---|---|---|---|
| | | | 5 µM | 10 µM | 12.5 µM | 25 µM |
| VPC-70413 | 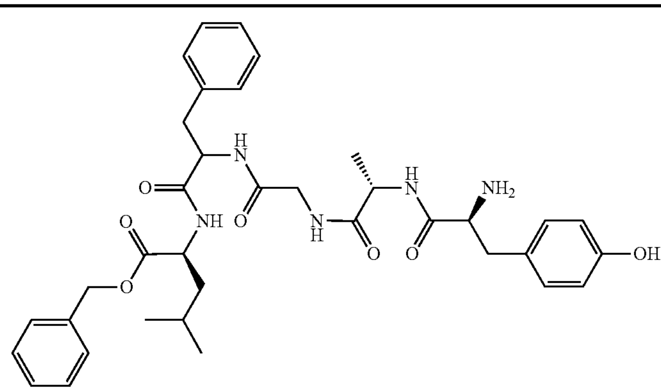 | ZINC000254739879 | | | | 114 |

TABLE 3-continued

FORMULA I STRUCTURES

| Compound # | Structure | ZINC # | % Inhibition ||||
| --- | --- | --- | --- | --- | --- | --- |
| | | | 5 μM | 10 μM | 12.5 μM | 25 μM |
| VPC-70063 | 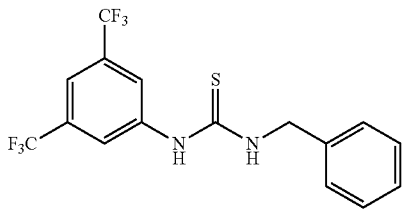 [SMILES: FC(F)(F)c1cc(NC(=S)NCc2ccccc2)cc(C(F)(F)F)c1] | ZINC06276840 | | | | 106 |
| VPC-70223 | 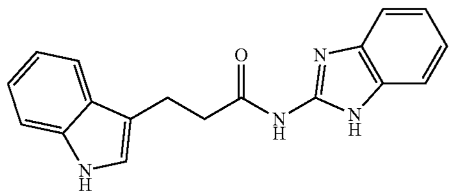 [SMILES: O=C(CCc1c[nH]c2ccccc12)Nc1nc2ccccc2[nH]1] | ZINC000006566969 | | | | 103 |
| VPC-70511 | 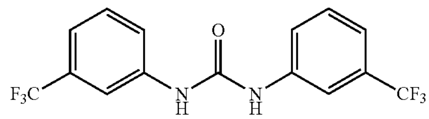 [SMILES: O=C(Nc1cccc(C(F)(F)F)c1)Nc1cccc(C(F)(F)F)c1] | ZINC1514731 | 108 | 112 | | 102 |
| VPC-70514 | 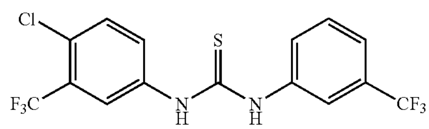 [SMILES: FC(F)(F)c1cccc(NC(=S)Nc2ccc(Cl)c(C(F)(F)F)c2)c1] | ZINC3444542 | 109 | 110 | | 102 |
| VPC-70523 | 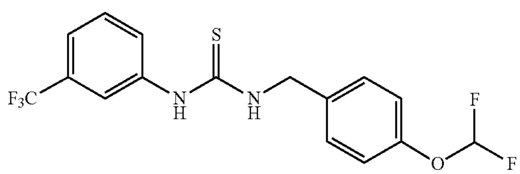 [SMILES: FC(F)Oc1ccc(CNC(=S)Nc2cccc(C(F)(F)F)c2)cc1] | ZINC20621585 | −4 | 104 | | 102 |
| VPC-70524 | 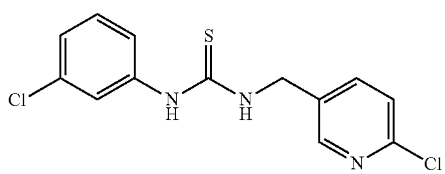 [SMILES: S=C(NCc1ccc(Cl)nc1)Nc1cccc(Cl)c1] | ZINC000006925983 | 22 | 4 | | 102 |
| VPC-70525 | 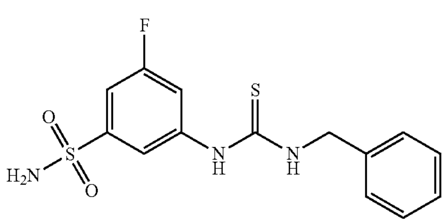 [SMILES: NS(=O)(=O)c1cc(F)cc(NC(=S)NCc2ccccc2)c1] | ZINC54988299 | 40 | 35 | | 102 |
| VPC-70532 | 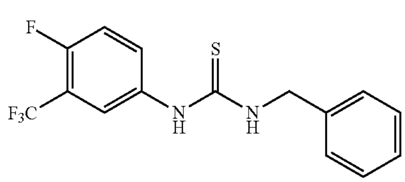 [SMILES: Fc1ccc(NC(=S)NCc2ccccc2)cc1C(F)(F)F] | ZINC921272327 | | | | 101 |

TABLE 3-continued

FORMULA I STRUCTURES

| Compound # | Structure | ZINC # | % Inhibition 5 μM | 10 μM | 12.5 μM | 25 μM |
|---|---|---|---|---|---|---|
| VPC-70215 | | ZINC000046700600 | | | | 101 |
| VPC-70498 | | ZINC763125903 | 36 | 106 | | 100 |
| VPC-70495 | | ZINC743008006 | 107 | 80 | | 100 |
| VPC-70489 | | ZINC727282890 | 38 | 86 | | 99 |
| VPC-70477 | | ZINC346751 | 3 | 30 | | 99 |
| VPC-70390 | | ZINC000009130116 | | | | 97 |
| VPC-70393 | | ZINC000009053472 | | | | 96 |

TABLE 3-continued

FORMULA I STRUCTURES

| Compound # | Structure | ZINC # | % Inhibition | | | |
|---|---|---|---|---|---|---|
| | | | 5 μM | 10 μM | 12.5 μM | 25 μM |
| VPC-70496 | (3,5-dichlorophenyl)-thiourea-CH2-(pyridin-3-yl) | ZINC000000088815 | 22 | 95 | | 96 |
| VPC-70535 | (3-CF3-phenyl)-thiourea-CH2-(2-CF3-phenyl) | ZINC745646914 | | | 95 | |
| VPC-70561 | (3-CF3-benzyl)-thiourea-CH2-(4-(2-hydroxypropan-2-yl)phenyl) | ZINC774226807 | | | 95 | |
| VPC-70021 | (3-CF3-phenyl)-urea-(3-carbamoylthiophen-2-yl) | ZINC12793756 | | | | 95 |
| VPC-70277 | 5-methoxy-indole-ethyl-NHC(O)-CH2CH2-(3-phenyl-1,2,4-oxadiazol-5-yl) | ZINC000009419770 | | | | 95 |
| VPC-70526 | (3-(phenoxymethyl)phenyl)-thiourea-CH2-phenyl | ZINC917599593 | 41 | 62 | | 94 |
| VPC-70529 | (3-CF3-phenyl)-thiourea-neopentyl | ZINC920075250 | 14 | 52 | | 94 |

TABLE 3-continued

FORMULA I STRUCTURES

| Compound # | Structure | ZINC # | % Inhibition | | | |
|---|---|---|---|---|---|---|
| | | | 5 μM | 10 μM | 12.5 μM | 25 μM |
| VPC-70530 | 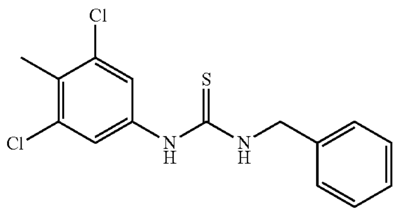 [SMILES: Cc1c(Cl)cc(NC(=S)NCc2ccccc2)cc1Cl] | ZINC920997608 | | | 94 | |
| VPC-70314 | 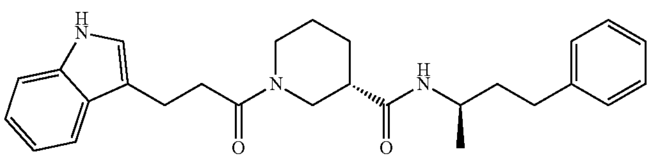 [SMILES: C[C@H](CCc1ccccc1)NC(=O)[C@H]1CCCN(C(=O)CCc2c[nH]c3ccccc23)C1] | ZINC000008765174 | | | | 93 |
| VPC-70465 | 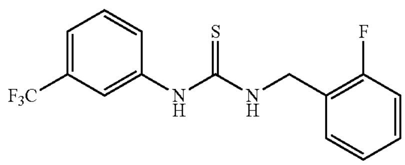 [SMILES: Fc1ccccc1CNC(=S)Nc1cccc(C(F)(F)F)c1] | ZINC000008683483 | 51 | 95 | | 92 |
| VPC-70527 | 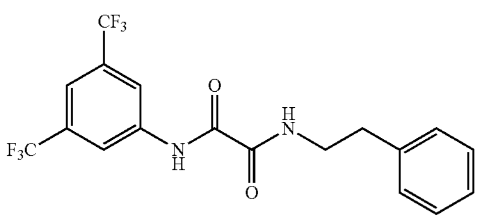 [SMILES: O=C(NCCc1ccccc1)C(=O)Nc1cc(C(F)(F)F)cc(C(F)(F)F)c1] | ZINC48586115 | 38 | 43 | | 92 |
| VPC-70478 | 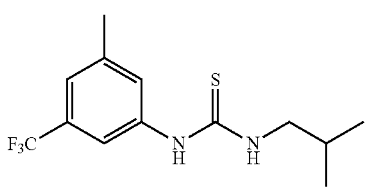 [SMILES: Cc1cc(NC(=S)NCC(C)C)cc(C(F)(F)F)c1] | ZINC792693672 | 26 | 65 | | 91 |
| VPC-70501 | 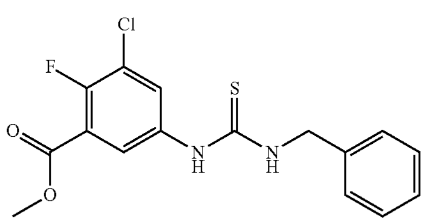 [SMILES: COC(=O)c1cc(NC(=S)NCc2ccccc2)cc(Cl)c1F] | ZINC790358193 | 34 | 37 | | 90 |
| VPC-70506 | 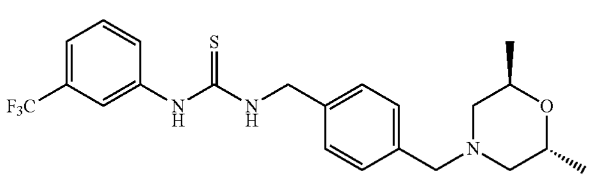 [SMILES: C[C@@H]1CN(Cc2ccc(CNC(=S)Nc3cccc(C(F)(F)F)c3)cc2)C[C@@H](C)O1] | ZINC914870928 | 73 | 66 | | 89 |

TABLE 3-continued

FORMULA I STRUCTURES

| Compound # | Structure | ZINC # | % Inhibition | | | |
|---|---|---|---|---|---|---|
| | | | 5 μM | 10 μM | 12.5 μM | 25 μM |
| VPC-70437 | 3,5-bis(trifluoromethyl)phenyl thiourea with (tetrahydrofuran-2-yl)methyl | ZINC000001121999 | 24 | 105 | | 87 |
| VPC-70458 | 3,4-dichlorophenyl thiourea with thiophen-2-ylmethyl | ZINC000000302471 | 42 | 104 | | 86 |
| VPC-70466 | 3,4-dichlorophenyl urea with 2-chlorobenzyl | ZINC000002881731 | 1 | 48 | | 86 |
| VPC-70387 | cinnamylidene-thiazolidinedione-propanamide-tryptamine | ZINC000013574717 | | | | 82 |
| VPC-70531 | benzyl thiourea phenyl methyl urea | ZINC921269106 | 0 | 27 | 47 | 81 |
| VPC-70033 | 2-nitro-4-trifluoromethyl-5-chloro-phenyl aminophenyl acetamide | ZINC04809037 | | | | 81 |
| VPC-70084 | 3,5-dichlorophenyl thiourea with pyridin-4-ylmethyl | ZINC07325649 | | | | 80 |

TABLE 3-continued

FORMULA I STRUCTURES

| Compound # | Structure | ZINC # | % Inhibition 5 μM | 10 μM | 12.5 μM | 25 μM |
|---|---|---|---|---|---|---|
| VPC-70483 | 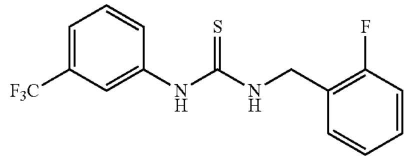 [SMILES: Fc1ccccc1CNC(=S)Nc1cccc(C(F)(F)F)c1] | ZINC726433246 | 31 | 38 | | 79 |
| VPC-70487 | 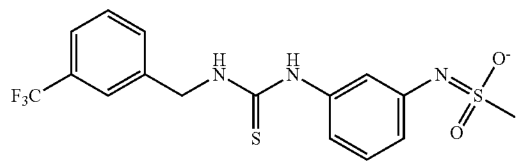 [SMILES: CS(=O)([O-])=Nc1cccc(NC(=S)NCc2cccc(C(F)(F)F)c2)c1] | ZINC726459938 | 34 | 42 | | 79 |
| VPC-70473 | 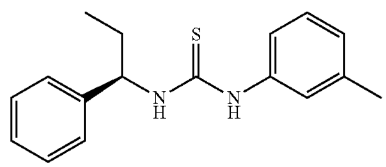 [SMILES: CC[C@@H](NC(=S)Nc1cccc(C)c1)c1ccccc1] | ZINC000013931514 | | | | 77 |
| VPC-70388 | 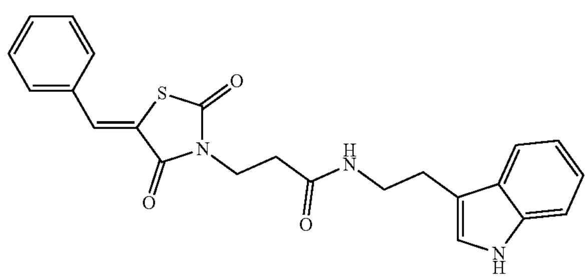 [SMILES: O=C(CCN1C(=O)S/C(=C\c2ccccc2)C1=O)NCCc1c[nH]c2ccccc12] | ZINC000009046072 | | | | 77 |
| VPC-70549 | 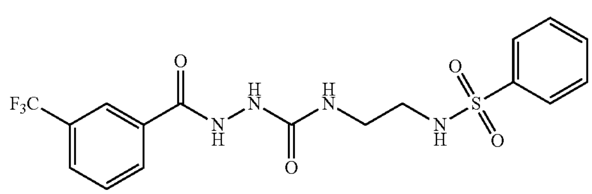 [SMILES: O=C(NCCNS(=O)(=O)c1ccccc1)NNC(=O)c1cccc(C(F)(F)F)c1] | ZINC730028134 | | | 75 | |
| VPC-70468 | 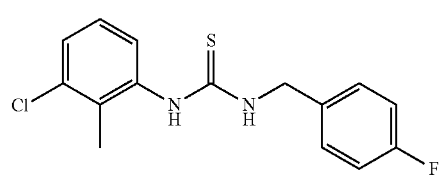 [SMILES: Cc1c(Cl)cccc1NC(=S)NCc1ccc(F)cc1] | ZINC000000307277 | 9 | 30 | | 74 |
| VPC-70381 | 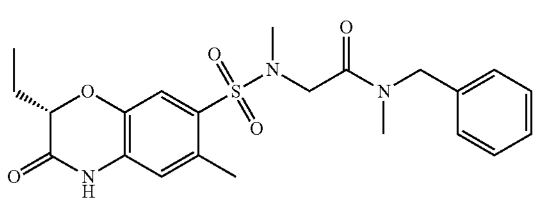 [SMILES: CC[C@@H]1Oc2cc(S(=O)(=O)N(C)CC(=O)N(C)Cc3ccccc3)c(C)cc2NC1=O] | ZINC000046056112 | | | | 74 |

TABLE 3-continued

FORMULA I STRUCTURES

| Compound # | Structure | ZINC # | % Inhibition 5 μM | 10 μM | 12.5 μM | 25 μM |
|---|---|---|---|---|---|---|
| VPC-70564 | (3-methyl-5-trifluoromethylphenyl)-N'-(isoxazol-3-ylmethyl)thiourea | ZINC792696003 | | | 73 | |
| VPC-70554 | 3-(trifluoromethyl)-N-(3-(benzylamino)-3-oxopropyl)benzamide | ZINC499670563 | | | 71 | |
| VPC-70053 | N-(3,4-dichlorobenzyl)-N'-(pyridin-3-yl)thiourea | ZINC00073052 | | | | 73 |
| VPC-70068 | (5-tert-butyl-4,5,6,7-tetrahydrobenzo[b]thiophen-2-yl)(4-carbamoylpiperidin-1-yl)methanone | ZINC33002149 | | | | 73 |

TABLE 4

FORMULA IV STRUCTURES

| Compound # | Structure | ZINC # | % Inhibition (25 μM) |
|---|---|---|---|
| VPC-70067 | (Z)-5-(2-(trifluoromethyl)benzylidene)-2-thioxothiazolidin-4-one | ZINC12616868 | 98 |
| VPC-70064 | (Z)-5-((E)-3-(furan-2-yl)allylidene)-3-methyl-2-thioxothiazolidin-4-one | ZINC12695008 | 78 |
| VPC-70005 | (Z)-3-(3-hydroxyphenyl)-5-(thiophen-2-ylmethylene)-2-thioxothiazolidin-4-one | ZINC01211334 | 65 |

TABLE 5

Below 70% Inhibition at 25 μM

| Compound # | Structure | ZINC # | % Inhibition 5 μM | 10 μM | 12.5 μM | 25 μM |
|---|---|---|---|---|---|---|
| VPC-70380 | | ZINC000064889578 | | | | 68 |
| VPC-70366 | | ZINC000040135677 | | | | 60 |
| VPC-70367 | | ZINC000006052981 | | | | 60 |
| VPC-70392 | | ZINC000010176407 | | | | 58 |
| VPC-70389 | | ZINC000009243143 | | | | 58 |
| VPC-70382 | | ZINC000003026309 | | | | 57 |

TABLE 5-continued
| | Below 70% Inhibition at 25 μM | | | | | |
|---|---|---|---|---|---|---|
| Compound # | Structure | ZINC # | \% Inhibition | | | |
| | | | 5 μM | 10 μM | 12.5 μM | 25 μM |
| VPC-70386 | 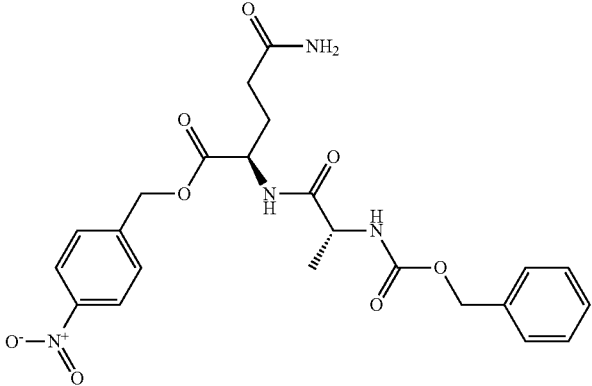 [SMILES: C[C@@H](NC(=O)OCc1ccccc1)C(=O)N[C@H](CCC(N)=O)C(=O)OCc1ccc([N+](=O)[O-])cc1] | ZINC000004065527 | | | | 55 |
| VPC-70376 | 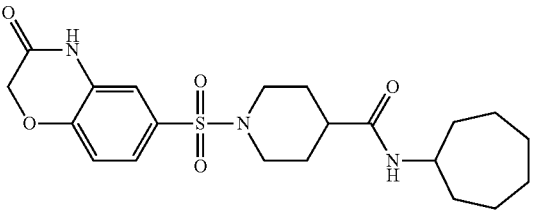 [SMILES: O=C1COc2ccc(S(=O)(=O)N3CCC(C(=O)NC4CCCCCC4)CC3)cc2N1] | ZINC000009502950 | | | | 55 |
| VPC-70395 | 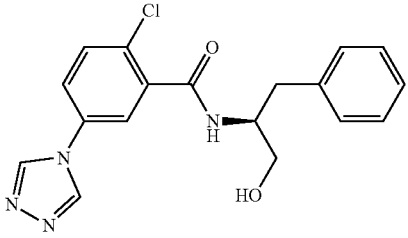 [SMILES: O=C(N[C@H](CO)Cc1ccccc1)c1cc(-n2cnnc2)ccc1Cl] | ZINC000218276666 | | | | 56 |
| VPC-70391 | 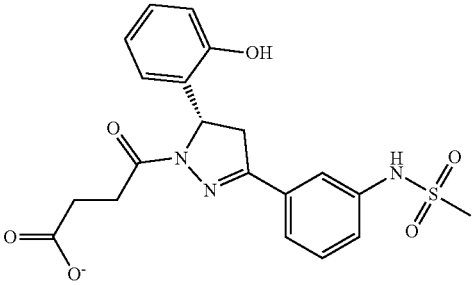 [SMILES: CS(=O)(=O)Nc1cccc(C2=NN(C(=O)CCC(=O)[O-])[C@H](c3ccccc3O)C2)c1] | ZINC000009060573 | | | | 54 |
| VPC-70394 | 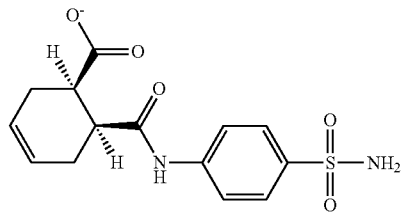 [SMILES: NS(=O)(=O)c1ccc(NC(=O)[C@H]2CC=CC[C@H]2C(=O)[O-])cc1] | ZINC000000214398 | | | | 54 |

TABLE 5-continued
Below 70% Inhibition at 25 μM
| Compound # | Structure | ZINC # | % Inhibition 5 μM | 10 μM | 12.5 μM | 25 μM |
|---|---|---|---|---|---|---|
| VPC-70405 | 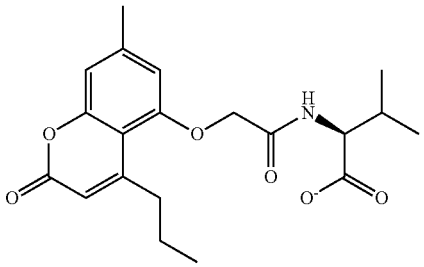 [SMILES: CCCc1cc(=O)oc2cc(C)cc(OCC(=O)N[C@H](C(=O)[O-])C(C)C)c12] | ZINC000002121723 | | | | 54 |
| VPC-70404 | 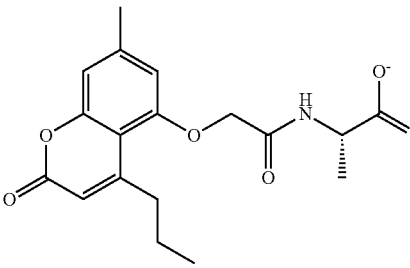 | ZINC000000487571 | | | | 53 |
| VPC-70384 | 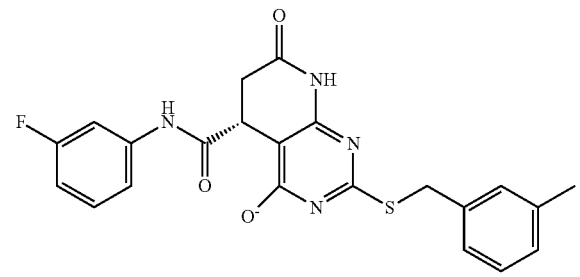 [SMILES: Cc1cccc(CSc2nc([O-])c3c(n2)NC(=O)C[C@H]3C(=O)Nc2cccc(F)c2)c1] | ZINC000046074815 | | | | 53 |
| VPC-70377 | 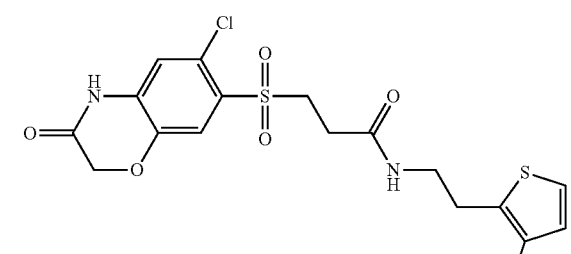 | ZINC000009440450 | | | | 52 |
| VPC-70379 | 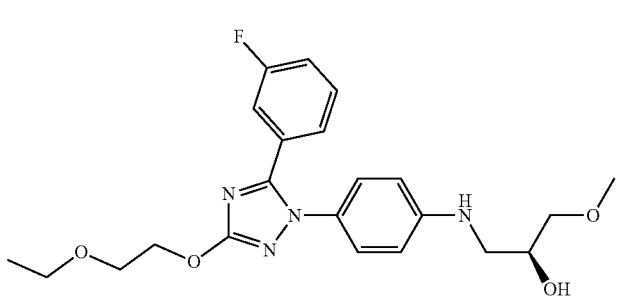 [SMILES: CCOCCOc1nc(-c2cccc(F)c2)n(-c2ccc(NC[C@H](O)COC)cc2)n1] | ZINC000036145736 | | | | 52 |

TABLE 5-continued
Below 70% Inhibition at 25 μM
| Compound # | Structure | ZINC # | % Inhibition 5 μM | 10 μM | 12.5 μM | 25 μM |
|---|---|---|---|---|---|---|
| VPC-70222 | 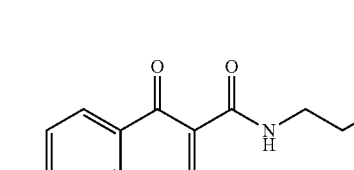 | ZINC000009796412 | | | | 68 |
| VPC-70219 | 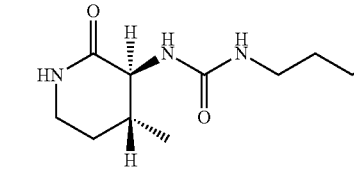 | ZINC000003335637 | | | | 67 |
| VPC-70249 | 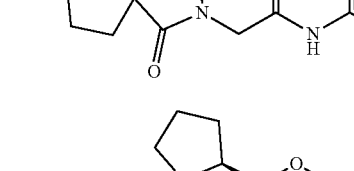 | ZINC000193817325 | | | | 65 |
| VPC-70066 | 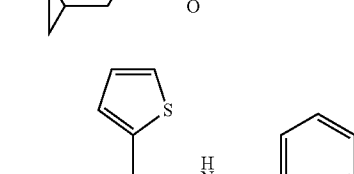 | ZINC03313540 | | | | 65 |
| VPC-70360 | 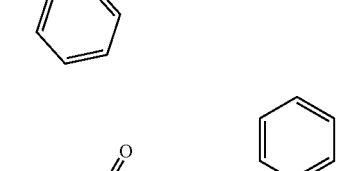 | ZINC000026417951 | | | | 64 |
| VPC-70361 | 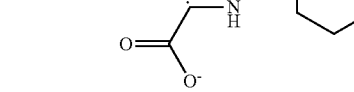 | ZINC000012905963 | | | | 61 |
| VPC-70318 | 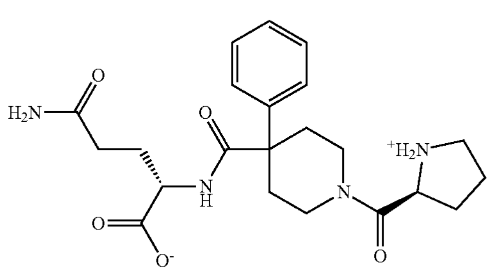 [SMILES: NC(=O)CC[C@H](NC(=O)C1(c2ccccc2)CCN(C(=O)[C@@H]2CCC[NH2+]2)CC1)C(=O)[O-]] | ZINC000008968624 | | | | 54 |

TABLE 5-continued

| | Below 70% Inhibition at 25 μM | | | | | |
|---|---|---|---|---|---|---|
| Compound # | Structure | ZINC # | \% Inhibition | | | |
| | | | 5 μM | 10 μM | 12.5 μM | 25 μM |
| VPC-70343 | | ZINC000013460087 | | | | 54 |
| VPC-70356 | | ZINC000096011836 | | | | 53 |
| VPC-70027 | | ZINC06975402 | | | | 53 |
| VPC-70209 | | ZINC000004583705 | | | | 52 |
| VPC-70146 | | ZINC000004648649 | | | | 52 |
| VPC-70355 | | ZINC000008881483 | | | | 51 |

TABLE 5-continued
Below 70% Inhibition at 25 μM
| Compound # | Structure | ZINC # | % Inhibition 5 μM | 10 μM | 12.5 μM | 25 μM |
|---|---|---|---|---|---|---|
| VPC-70345 | 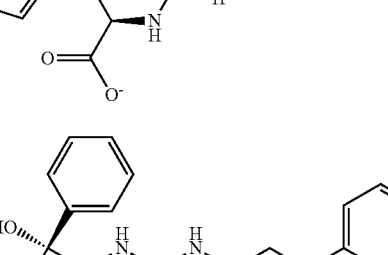 | ZINC000013236186 | | | | 51 |
| VPC-70205 | 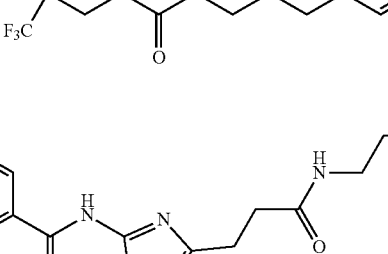 | ZINC000070636616 | | | | 50 |
| VPC-70131 | 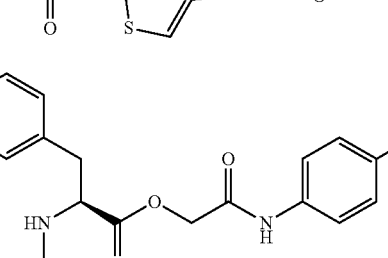 | ZINC000011834898 | | | | 50 |
| VPC-70339 | 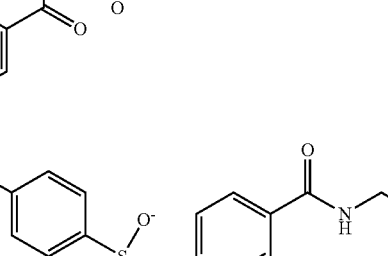 | ZINC000002642231 | | | | 50 |
| VPC-70341 | 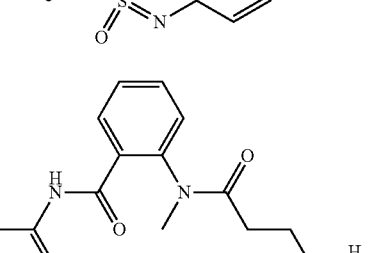 | ZINC000013109284 | | | | 50 |
| VPC-70340 | 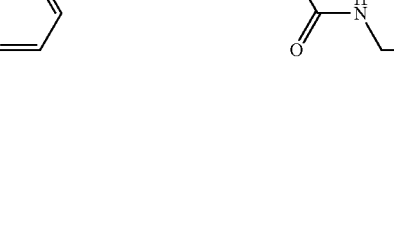 | ZINC000014095493 | | | | 49 |

TABLE 5-continued

| | Below 70% Inhibition at 25 μM | | | | | |
|---|---|---|---|---|---|---|
| Compound # | Structure | ZINC # | \% Inhibition | | | |
| | | | 5 μM | 10 μM | 12.5 μM | 25 μM |
| VPC-70344 | | ZINC000225552803 | | | | 49 |
| VPC-70358 | | ZINC000014185488 | | | | 48 |
| VPC-70240 | | ZINC000058356756 | | | | 48 |
| VPC-70267 | | ZINC000095401009 | | | | 47 |
| VPC-70211 | | ZINC000014094353 | | | | 47 |
| VPC-70252 | | ZINC000058282342 | | | | 45 |
| VPC-70283 | | ZINC000220134452 | | | | 45 |

TABLE 5-continued

Below 70% Inhibition at 25 μM

| Compound # | Structure | ZINC # | % Inhibition 5 μM | 10 μM | 12.5 μM | 25 μM |
|---|---|---|---|---|---|---|
| VPC-70359 | 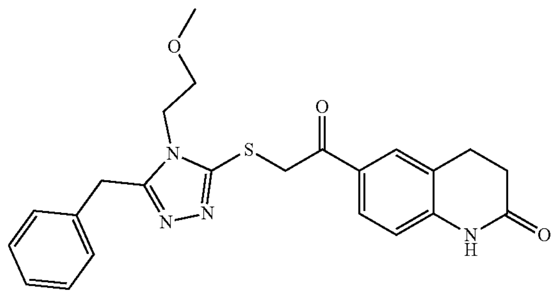 [SMILES: COCCn1c(Cc2ccccc2)nnc1SCC(=O)c1ccc2c(c1)CCC(=O)N2] | ZINC000009670218 | | | | 41 |
| VPC-70158 | 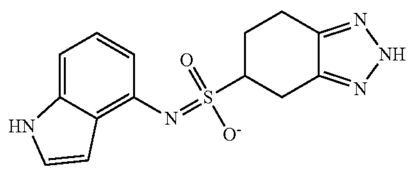 [SMILES: O=S([O-])(=Nc1cccc2[nH]ccc12)C1CCc2n[nH]nc2C1] | ZINC000225797127 | | | | 41 |
| VPC-70255 | 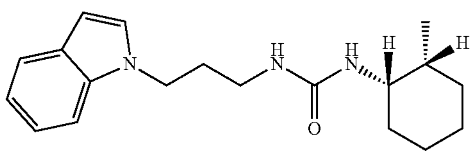 [SMILES: C[C@@H]1CCCC[C@@H]1NC(=O)NCCCn1ccc2ccccc21] | ZINC000040024098 | | | | 40 |
| VPC-70216 | 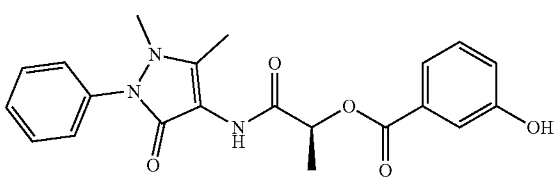 [SMILES: Cc1c(NC(=O)[C@H](C)OC(=O)c2cccc(O)c2)c(=O)n(-c2ccccc2)n1C] | ZINC000005754766 | | | | 40 |
| VPC-70163 | 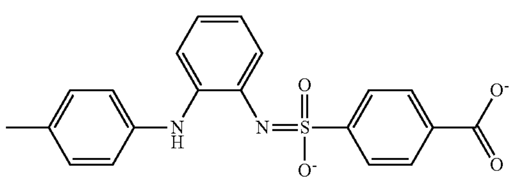 [SMILES: Cc1ccc(Nc2ccccc2N=S(=O)([O-])c2ccc(C(=O)[O-])cc2)cc1] | ZINC000013059960 | | | | 39 |
| VPC-70266 | 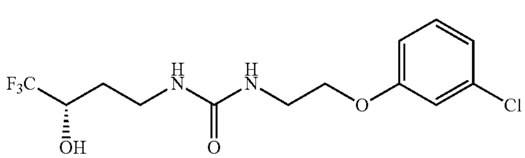 [SMILES: O=C(NCCOc1cccc(Cl)c1)NCC[C@H](O)C(F)(F)F] | ZINC000096413285 | | | | 38 |
| VPC-70247 | 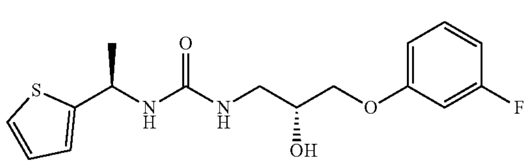 [SMILES: C[C@@H](NC(=O)NC[C@@H](O)COc1cccc(F)c1)c1cccs1] | ZINC000044955217 | | | | 35 |
| VPC-70261 | 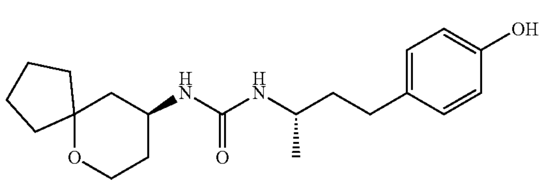 [SMILES: C[C@@H](CCc1ccc(O)cc1)NC(=O)N[C@H]1CCOC2(CCCC2)C1] | ZINC000095426104 | | | | 35 |

TABLE 5-continued

Below 70% Inhibition at 25 μM

| Compound # | Structure | ZINC # | % Inhibition 5 μM | 10 μM | 12.5 μM | 25 μM |
|---|---|---|---|---|---|---|
| VPC-70258 | 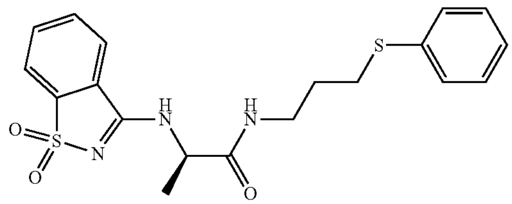 [SMILES: C[C@@H](NC1=NS(=O)(=O)c2ccccc21)C(=O)NCCCSc1ccccc1] | ZINC9738035 | | | | 34 |
| VPC-70236 | 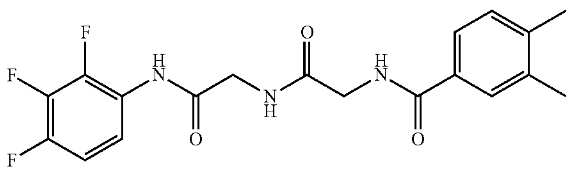 [SMILES: Cc1ccc(C(=O)NCC(=O)NCC(=O)Nc2ccc(F)c(F)c2F)cc1C] | ZINC000005273329 | | | | 32 |
| VPC-70263 | 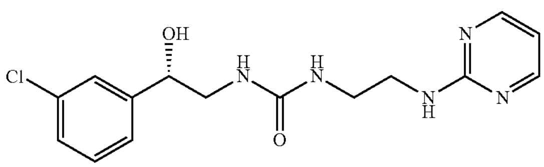 [SMILES: O=C(NCCNc1ncccn1)NC[C@@H](O)c1cccc(Cl)c1] | ZINC000048278811 | | | | 32 |

TABLE 6

Additional Compounds

| Compound # | Structure | ZINC # | % Inhibition 5 μM | 10 μM | 12.5 μM | 25 μM |
|---|---|---|---|---|---|---|
| VPC-70551 | 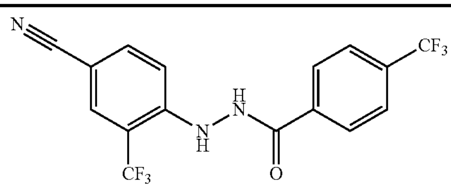 | ZINC799750908 | | | | 91 |
| VPC-70127 | 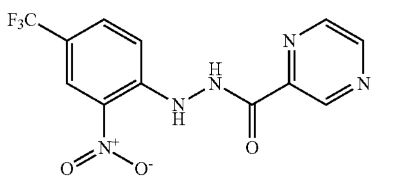 [SMILES: O=C(NNc1ccc(C(F)(F)F)cc1[N+](=O)[O-])c1cnccn1] | ZINC21285336 | | | | 106 |

Furthermore, VPC-70551 had an $IC_{50}$ of 4 μM and a half-life of 140 minutes.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

REFERENCES

[1] C. V. Dang, MYC on the path to cancer, Cell, 149 (2012) 22-35.

[2] C. V. Dang, MYC, metabolism, cell growth, and tumorigenesis, Cold Spring Harbor perspectives in medicine, 3 (2013).

[3] C. V. Dang, L. M. Resar, E. Emison, S. Kim, Q. Li, J. E. Prescott, D. Wonsey, K. Zeller, Function of the c-Myc oncogenic transcription factor, Experimental cell research, 253 (1999) 63-77.

[4] R. Ponzielli, S. Katz, D. Barsyte-Lovejoy, L. Z. Penn, Cancer therapeutics: targeting the dark side of Myc, European journal of cancer, 41 (2005) 2485-2501.

[5] M. Huang, W. A. Weiss, Neuroblastoma and MYCN, Cold Spring Harbor perspectives in medicine, 3 (2013) a014415.

[6] Z. E. Stine, Z. E. Walton, B. J. Altman, A. L. Hsieh, C. V. Dang, MYC, Metabolism, and Cancer, Cancer discovery, 5 (2015) 1024-1039.

[7] S. B. McMahon, MYC and the control of apoptosis, Cold Spring Harbor perspectives in medicine, 4 (2014) a014407.

[8] M. Gabay, Y. Li, D. W. Felsher, MYC activation is a hallmark of cancer initiation and maintenance, Cold Spring Harbor perspectives in medicine, 4 (2014).

[9] D. Horiuchi, B. Anderton, A. Goga, Taking on challenging targets: making MYC druggable, American Society of Clinical Oncology educational book. American Society of Clinical Oncology. Meeting, (2014) e497-502.

[10] C. M. Koh, C. J. Bieberich, C. V. Dang, W. G. Nelson, S. Yegnasubramanian, A. M. De Marzo, MYC and Prostate Cancer, Genes & cancer, 1 (2010) 617-628.

[11] P. C. Boutros, M. Fraser, N. J. Harding, R. de Borja, D. Trudel, E. Lalonde, A. Meng, P. H. Hennings-Yeomans, A. McPherson, V. Y. Sabelnykova, A. Zia, N. S. Fox, J. Livingstone, Y. J. Shiah, J. Wang, T. A. Beck, C. L. Have, T. Chong, M. Sam, J. Johns, L. Timms, N. Buchner, A. Wong, J. D. Watson, T. T. Simmons, C. P'ng, G. Zafarana, F. Nguyen, X. Luo, K. C. Chu, S. D. Prokopec, J. Sykes, A. Dal Pra, A. Berlin, A. Brown, M. A. Chan-Seng-Yue, F. Yousif, R. E. Denroche, L. C. Chong, G. M. Chen, E. Jung, C. Fung, M. H. Starmans, H. Chen, S. K. Govind, J. Hawley, A. D'Costa, M. Pintilie, D. Waggott, F. Hach, P. Lambin, L. B. Muthuswamy, C. Cooper, R. Eeles, D. Neal, B. Tetu, C. Sahinalp, L. D. Stein, N. Fleshner, S. P. Shah, C. C. Collins, T. J. Hudson, J. D. McPherson, T. van der Kwast, R. G. Bristow, Spatial genomic heterogeneity within localized, multifocal prostate cancer, Nature genetics, 47 (2015) 736-745.

[12] A. W. Wyatt, M. E. Gleave, Targeting the adaptive molecular landscape of castration-resistant prostate cancer, EMBO molecular medicine, 7 (2015) 878-894.

[13] H. Beltran, S. Tomlins, A. Aparicio, V. Arora, D. Rickman, G. Ayala, J. Huang, L. True, M. E. Gleave, H. Soule, C. Logothetis, M. A. Rubin, Aggressive variants of castration-resistant prostate cancer, Clinical cancer research: an official journal of the American Association for Cancer Research, 20 (2014) 2846-2850.

[14] H. Beltran, D. Prandi, J. M. Mosquera, M. Benelli, L. Puca, J. Cyrta, C. Marotz, E. Giannopoulou, B. V. Chakravarthi, S. Varambally, S. A. Tomlins, D. M. Nanus, S. T. Tagawa, E. M. Van Allen, O. Elemento, A. Sboner, L. A. Garraway, M. A. Rubin, F. Demichelis, Divergent clonal evolution of castration-resistant neuroendocrine prostate cancer, Nature medicine, 22 (2016) 298-305.

[15] H. Beltran, D. S. Rickman, K. Park, S. S. Chae, A. Sboner, T. Y. MacDonald, Y. Wang, K. L. Sheikh, S. Terry, S. T. Tagawa, R. Dhir, J. B. Nelson, A. de la Taille, Y. Allory, M. B. Gerstein, S. Perner, K. J. Pienta, A. M. Chinnaiyan, Y. Wang, C. C. Collins, M. E. Gleave, F. Demichelis, D. M. Nanus, M. A. Rubin, Molecular characterization of neuroendocrine prostate cancer and identification of new drug targets, Cancer discovery, 1 (2011) 487-495.

[16] D. Bernard, A. Pourtier-Manzanedo, J. Gil, D. H. Beach, Myc confers androgen-independent prostate cancer cell growth, The Journal of clinical investigation, 112 (2003) 1724-1731.

[17] J. H. Kim, S. M. Dhanasekaran, R. Mehra, S. A. Tomlins, W. Gu, J. Yu, C. Kumar-Sinha, X. Cao, A. Dash, L. Wang, D. Ghosh, K. Shedden, J. E. Montie, M. A. Rubin, K. J. Pienta, R. B. Shah, A. M. Chinnaiyan, Integrative analysis of genomic aberrations associated with prostate cancer progression, Cancer research, 67 (2007) 8229-8239.

[18] S. J. Barfeld, A. Urbanucci, H. M. Itkonen, L. Fazli, J. L. Hicks, B. Thiede, P. S. Rennie, S. Yegnasubramanian, A. M. DeMarzo, I. G. Mills, c-Myc Antagonises the Transcriptional Activity of the Androgen Receptor in Prostate Cancer Affecting Key Gene Networks, EBioMedicine, 18 (2017) 83-93.

[19] A. V. Lapuk, S. V. Volik, Y. Wang, C. C. Collins, The role of mRNA splicing in prostate cancer, Asian journal of andrology, 16 (2014) 515-521.

[20] N. Nadiminty, R. Tummala, C. Liu, W. Lou, C. P. Evans, A. C. Gao, NF-kappaB2/p52:c-Myc:hnRNPA1 Pathway Regulates Expression of Androgen Receptor Splice Variants and Enzalutamide Sensitivity in Prostate Cancer, Molecular cancer therapeutics, 14 (2015) 1884-1895.

[21] R. Hu, C. Lu, E. A. Mostaghel, S. Yegnasubramanian, M. Gurel, C. Tannahill, J. Edwards, W. B. Isaacs, P. S. Nelson, E. Bluemn, S. R. Plymate, J. Luo, Distinct transcriptional programs mediated by the ligand-dependent full-length androgen receptor and its splice variants in castration-resistant prostate cancer, Cancer research, 72 (2012) 3457-3462.

[22] S. Akamatsu, T. Inoue, O. Ogawa, M. E. Gleave, Clinical and molecular features of treatment-related neuroendocrine prostate cancer, International journal of urology: official journal of the Japanese Urological Association, 25 (2018) 345-351.

[23] E. M. Blackwood, R. N. Eisenman, Max: a helix-loop-helix zipper protein that forms a sequence-specific DNA-binding complex with Myc, Science, 251 (1991) 1211-1217.

[24] G. J. Kato, W. M. Lee, L. L. Chen, C. V. Dang, Max: functional domains and interaction with c-Myc, Genes & development, 6 (1992) 81-92.

[25] W. D. Thomas, A. Raif, L. Hansford, G. Marshall, N-myc transcription molecule and oncoprotein, The international journal of biochemistry & cell biology, 36 (2004) 771-775.

[26] M. Conacci-Sorrell, L. McFerrin, R. N. Eisenman, An overview of MYC and its interactome, Cold Spring Harbor perspectives in medicine, 4 (2014) a014357.

[27] J. Michel, R. Cuchillo, The impact of small molecule binding on the energy landscape of the intrinsically disordered protein C-myc, PloS one, 7 (2012) e41070.

[28] F. Jin, C. Yu, L. Lai, Z. Liu, Ligand clouds around protein clouds: a scenario of ligand binding with intrinsically disordered proteins, PLoS computational biology, 9 (2013) e1003249.

[29] C. Yu, X. Niu, F. Jin, Z. Liu, C. Jin, L. Lai, Structure-Based Inhibitor Design for the Intrinsically Disordered Protein c-Myc, Scientific reports, 6 (2016) 22298.

[30] B. Luscher, L. G. Larsson, The basic region/helix-loop-helix/leucine zipper domain of Myc proto-oncoproteins: function and regulation, Oncogene, 18 (1999) 2955-2966.

[31] A. Sabo, B. Amati, Genome recognition by MYC, Cold Spring Harbor perspectives in medicine, 4 (2014).

[32] P. B. Rahl, R. A. Young, MYC and transcription elongation, Cold Spring Harbor perspectives in medicine, 4 (2014) a020990.

[33] A. R. Ferre-D'Amare, G. C. Prendergast, E. B. Ziff, S. K. Burley, Recognition by Max of its cognate DNA through a dimeric b/HLH/Z domain, Nature, 363 (1993) 38-45.

[34] S. K. Nair, S. K. Burley, X-ray structures of Myc-Max and Mad-Max recognizing DNA. Molecular bases of regulation by proto-oncogenic transcription factors, Cell, 112 (2003) 193-205.

[35] L. Soucek, J. Whitfield, C. P. Martins, A. J. Finch, D. J. Murphy, N. M. Sodir, A. N. Karnezis, L. B. Swigart, S. Nasi, G. I. Evan, Modelling Myc inhibition as a cancer therapy, Nature, 455 (2008) 679-683.

[36] L. Soucek, J. R. Whitfield, N. M. Sodir, D. Masso-Valles, E. Serrano, A. N. Karnezis, L. B. Swigart, G. I. Evan, Inhibition of Myc family proteins eradicates KRas-driven lung cancer in mice, Genes & development, 27 (2013) 504-513.

[37] X. Yin, C. Giap, J. S. Lazo, E. V. Prochownik, Low molecular weight inhibitors of Myc-Max interaction and function, Oncogene, 22 (2003) 6151-6159.

[38] J. L. Yap, H. Wang, A. Hu, J. Chauhan, K. Y. Jung, R. B. Gharavi, E. V. Prochownik, S. Fletcher, Pharmacophore identification of c-Myc inhibitor 10074-G5, Bioorganic & medicinal chemistry letters, 23 (2013) 370-374.

[39] D. Stellas, M. Szabolcs, S. Koul, Z. Li, A. Polyzos, C. Anagnostopoulos, Z. Cournia, C. Tamvakopoulos, A. Klinakis, A. Efstratiadis, Therapeutic effects of an anti-Myc drug on mouse pancreatic cancer, Journal of the National Cancer Institute, 106 (2014).

[40] J. R. Hart, A. L. Garner, J. Yu, Y. Ito, M. Sun, L. Ueno, J. K. Rhee, M. M. Baksh, E. Stefan, M. Hartl, K. Bister, P. K. Vogt, K. D. Janda, Inhibitor of MYC identified in a Krohnke pyridine library, Proceedings of the National Academy of Sciences of the United States of America, 111 (2014) 12556-12561.

[41] J. R. Whitfield, M. E. Beaulieu, L. Soucek, Strategies to Inhibit Myc and Their Clinical Applicability, Frontiers in cell and developmental biology, 5 (2017) 10.

[42] C. M. Koh, A. Sabo, E. Guccione, Targeting MYC in cancer therapy: RNA processing offers new opportunities, BioEssays: news and reviews in molecular, cellular and developmental biology, 38 (2016) 266-275.

[43] M. R. McKeown, J. E. Bradner, Therapeutic strategies to inhibit MYC, Cold Spring Harbor perspectives in medicine, 4 (2014).

[44] D. S. Rickman, J. H. Schulte, M. Eilers, The Expanding World of N-MYC-Driven Tumors, Cancer discovery, 8 (2018) 150-163.

[45] A. V. Follis, D. I. Hammoudeh, H. Wang, E. V. Prochownik, S. J. Metallo, Structural rationale for the coupled binding and unfolding of the c-Myc oncoprotein by small molecules, Chemistry & biology, 15 (2008) 1149-1155.

[46] D. I. Hammoudeh, A. V. Follis, E. V. Prochownik, S. J. Metallo, Multiple independent binding sites for small-molecule inhibitors on the oncoprotein c-Myc, Journal of the American Chemical Society, 131 (2009) 7390-7401.

[47] H. Wang, D. I. Hammoudeh, A. V. Follis, B. E. Reese, J. S. Lazo, S. J. Metallo, E. V. Prochownik, Improved low molecular weight Myc-Max inhibitors, Molecular cancer therapeutics, 6 (2007) 2399-2408.

[48] H. Wang, J. Chauhan, A. Hu, K. Pendleton, J. L. Yap, P. E. Sabato, J. W. Jones, M. Perri, J. Yu, E. Cione, M. A. Kane, S. Fletcher, E. V. Prochownik, Disruption of Myc-Max heterodimerization with improved cell-penetrating analogs of the small molecule 10074-G5, Oncotarget, 4 (2013) 936-947.

[49] J. Guo, R. A. Parise, E. Joseph, M. J. Egorin, J. S. Lazo, E. V. Prochownik, J. L. Eiseman, Efficacy, pharmacokinetics, tisssue distribution, and metabolism of the Myc-Max disruptor, 10058-F4 [Z,E]-5-[4-ethylbenzylidene]-2-thioxothiazolidin-4-one, in mice, Cancer chemotherapy and pharmacology, 63 (2009) 615-625.

[50] D. M. Clausen, J. Guo, R. A. Parise, J. H. Beumer, M. J. Egorin, J. S. Lazo, E. V. Prochownik, J. L. Eiseman, In vitro cytotoxicity and in vivo efficacy, pharmacokinetics, and metabolism of 10074-G5, a novel small-molecule inhibitor of c-Myc/Max dimerization, The Journal of pharmacology and experimental therapeutics, 335 (2010) 715-727.

[51] Molecular Operating Environment (MOE), 2013.08; Chemical Computing Group ULC, 1010 Sherbooke St. West, Suite #910, Montreal, QC, Canada, H3A 2R7, 2018.

[52] L. A. Jung, A. Gebhardt, W. Koelmel, C. P. Ade, S. Walz, J. Kuper, B. von Eyss, S. Letschert, C. Redel, L. d'Artista, A. Biankin, L. Zender, M. Sauer, E. Wolf, G. Evan, C. Kisker, M. Eilers, OmoMYC blunts promoter invasion by oncogenic MYC to inhibit gene expression characteristic of MYC-dependent tumors, Oncogene, 36 (2017) 1911-1924.

[53] J. J. Irwin, B. K. Shoichet, ZINC—a free database of commercially available compounds for virtual screening, Journal of chemical information and modeling, 45 (2005) 177-182.

[54] J. J. Irwin, T. Sterling, M. M. Mysinger, E. S. Bolstad, R. G. Coleman, ZINC: a free tool to discover chemistry for biology, Journal of chemical information and modeling, 52 (2012) 1757-1768.

[55] R. A. Friesner, J. L. Banks, R. B. Murphy, T. A. Halgren, J. J. Klicic, D. T. Mainz, M. P. Repasky, E. H. Knoll, M. Shelley, J. K. Perry, D. E. Shaw, P. Francis, P. S. Shenkin, Glide: a new approach for rapid, accurate docking and scoring. 1. Method and assessment of docking accuracy, Journal of medicinal chemistry, 47 (2004) 1739-1749.

[56] T. A. Halgren, R. B. Murphy, R. A. Friesner, H. S. Beard, L. L. Frye, W. T. Pollard, J. L. Banks, Glide: a new approach for rapid, accurate docking and scoring. 2. Enrichment factors in database screening, Journal of medicinal chemistry, 47 (2004) 1750-1759.

[57] Schrödinger Release 2018-1: Maestro, Schrödinger, LLC, New York, N. Y., 2018.

[58] M. J. Huang, Y. C. Cheng, C. R. Liu, S. Lin, H. E. Liu, A small-molecule c-Myc inhibitor, 10058-F4, induces cell-cycle arrest, apoptosis, and myeloid differentiation of human acute myeloid leukemia, Experimental hematology, 34 (2006) 1480-1489.

[59] N. Lallous, K. Dalal, A. Cherkasov, P. S. Rennie, Targeting alternative sites on the androgen receptor to treat castration-resistant prostate cancer, International journal of molecular sciences, 14 (2013) 12496-12519.

[60] P. Axerio-Cilies, N. A. Lack, M. R. Nayana, K. H. Chan, A. Yeung, E. Leblanc, E. S. Guns, P. S. Rennie, A. Cherkasov, Inhibitors of androgen receptor activation function-2 (AF2) site identified through virtual screening, Journal of medicinal chemistry, 54 (2011) 6197-6205.

[61] N. A. Lack, P. Axerio-Cilies, P. Tavassoli, F. Q. Han, K. H. Chan, C. Feau, E. LeBlanc, E. T. Guns, R. K. Guy, P. S. Rennie, A. Cherkasov, Targeting the binding function 3 (BF3) site of the human androgen receptor through virtual screening, Journal of medicinal chemistry, 54 (2011) 8563-8573.

[62] R. S. Munuganti, E. Leblanc, P. Axerio-Cilies, C. Labriere, K. Frewin, K. Singh, M. D. Hassona, N. A. Lack, H. Li, F. Ban, E. Tomlinson Guns, R. Young, P. S. Rennie, A. Cherkasov, Targeting the binding function 3 (BF3) site of the androgen receptor through virtual screening. 2. development of 2-((2-phenoxyethyl) thio)-1H-benzimidazole derivatives, Journal of medicinal chemistry, 56 (2013) 1136-1148.

[63] R. S. Munuganti, M. D. Hassona, E. Leblanc, K. Frewin, K. Singh, D. Ma, F. Ban, M. Hsing, H. Adomat, N. Lallous, C. Andre, J. P. Jonadass, A. Zoubeidi, R. N. Young, E. T. Guns, P. S. Rennie, A. Cherkasov, Identification of a potent antiandrogen that targets the BF3 site of the androgen receptor and inhibits enzalutamide-resistant prostate cancer, Chemistry & biology, 21 (2014) 1476-1485.

[64] F. Ban, E. Leblanc, H. Li, R. S. Munuganti, K. Frewin, P. S. Rennie, A. Cherkasov, Discovery of 1H-indole-2-carboxamides as novel inhibitors of the androgen receptor binding function 3 (BF3), Journal of medicinal chemistry, 57 (2014) 6867-6872.

[65] H. Li, M. D. Hassona, N. A. Lack, P. Axerio-Cilies, E. Leblanc, P. Tavassoli, N. Kanaan, K. Frewin, K. Singh, H. Adomat, K. J. Bohm, H. Prinz, E. T. Guns, P. S. Rennie, A. Cherkasov, Characterization of a new class of androgen receptor antagonists with potential therapeutic application in advanced prostate cancer, Molecular cancer therapeutics, 12 (2013) 2425-2435.

[66] H. Li, F. Ban, K. Dalal, E. Leblanc, K. Frewin, D. Ma, H. Adomat, P. S. Rennie, A. Cherkasov, Discovery of small-molecule inhibitors selectively targeting the DNA-binding domain of the human androgen receptor, Journal of medicinal chemistry, 57 (2014) 6458-6467.

[67] K. Dalal, M. Roshan-Moniri, A. Sharma, H. Li, F. Ban, M. D. Hassona, M. Hsing, K. Singh, E. LeBlanc, S. Dehm, E. S. Tomlinson Guns, A. Cherkasov, P. S. Rennie, Selectively targeting the DNA-binding domain of the androgen receptor as a prospective therapy for prostate cancer, The Journal of biological chemistry, 289 (2014) 26417-26429.

[68] P. C. Hawkins, A. G. Skillman, A. Nicholls, Comparison of shape-matching and docking as virtual screening tools, Journal of medicinal chemistry, 50 (2007) 74-82.

[69] OpenEye Scientific Software, Santa Fe, NM http://www.eyesopen.com (last accessed May, 2018).

[70] T. Sterling, J. J. Irwin, ZINC 15—Ligand Discovery for Everyone, Journal of chemical information and modeling, 55 (2015) 2324-2337.

[71] P. C. Hawkins, A. G. Skillman, G. L. Warren, B. A. Ellingson, M. T. Stahl, Conformer generation with OMEGA: algorithm and validation using high quality structures from the Protein Databank and Cambridge Structural Database, Journal of chemical information and modeling, 50 (2010) 572-584.

[72] M. A. Neves, M. Totrov, R. Abagyan, Docking and scoring with ICM: the benchmarking results and strategies for improvement, Journal of computer-aided molecular design, 26 (2012) 675-686.

[73] M. McGann, FRED pose prediction and virtual screening accuracy, Journal of chemical information and modeling, 51 (2011) 578-596.

[74] M. McGann, FRED and HYBRID docking performance on standardized datasets, Journal of computer-aided molecular design, 26 (2012) 897-906.

[75] mol_rmsd Calculate RMSD's for docking results, Scientific Vector Language (SVL) source code provided by Chemical Computing Group ULC, 1010 Sherbooke St. West, Suite #910, Montreal, QC, Canada, H3A 2R7, 2018.

[76] scoring Analysis tool for non-bonded intermolecular interactions: H-bonds, transition metal, water bridges, hydrophobic, Scientific Vector Language (SVL) source code provided by Chemical Computing Group ULC, 1010 Sherbooke St. West, Suite #910, Montreal, QC, Canada, H3A 2R7, 2018.

[77] A. Cherkasov, E. N. Muratov, D. Fourches, A. Varnek, Baskin, II, M. Cronin, J. Dearden, P. Gramatica, Y. C. Martin, R. Todeschini, V. Consonni, V. E. Kuz'min, R. Cramer, R. Benigni, C. Yang, J. Rathman, L. Terfloth, J. Gasteiger, A. Richard, A. Tropsha, QSAR modeling: where have you been? Where are you going to?, Journal of medicinal chemistry, 57 (2014) 4977-5010.

[78] N. Paul, L. A. Carabet, N. Lallous, T. Yamazaki, M. E. Gleave, P. S. Rennie, A. Cherkasov, Cheminformatics Modeling of Adverse Drug Responses by Clinically Relevant Mutants of Human Androgen Receptor, Journal of chemical information and modeling, 56 (2016) 2507-2516.

[79] F. Ban, K. Dalal, H. Li, E. LeBlanc, P. S. Rennie, A. Cherkasov, Best Practices of Computer-Aided Drug Discovery: Lessons Learned from the Development of a Preclinical Candidate for Prostate Cancer with a New Mechanism of Action, Journal of chemical information and modeling, 57 (2017) 1018-1028.

[80] Schrödinger Release 2018-1: FEP+, Schrödinger, New York, N. Y., 2018.

[81] R. Abel, L. Wang, E. D. Harder, B. J. Berne, R. A. Friesner, Advancing Drug Discovery through Enhanced Free Energy Calculations, Accounts of chemical research, 50 (2017) 1625-1632.

[82] B. Kuhn, M. Tichy, L. Wang, S. Robinson, R. E. Martin, A. Kuglstatter, J. Benz, M. Giroud, T. Schirmeister, R. Abel, F. Diederich, J. Hert, Prospective Evaluation of Free Energy Calculations for the Prioritization of Cathepsin L Inhibitors, Journal of medicinal chemistry, 60 (2017) 2485-2497.

[83] L. Wang, Y. Deng, Y. Wu, B. Kim, D. N. LeBard, D. Wandschneider, M. Beachy, R. A. Friesner, R. Abel, Accurate Modeling of Scaffold Hopping Transformations in Drug Discovery, Journal of chemical theory and computation, 13 (2017) 42-54.

[84] E. Harder, W. Damm, J. Maple, C. Wu, M. Reboul, J. Y. Xiang, L. Wang, D. Lupyan, M. K. Dahlgren, J. L. Knight, J. W. Kaus, D. S. Cerutti, G. Krilov, W. L. Jorgensen, R. Abel, R. A. Friesner, OPLS3: A Force Field Providing Broad Coverage of Drug-like Small Molecules and Proteins, Journal of chemical theory and computation, 12 (2016) 281-296.

[85] L. Wang, Y. Wu, Y. Deng, B. Kim, L. Pierce, G. Krilov, D. Lupyan, S. Robinson, M. K. Dahlgren, J. Greenwood, D. L. Romero, C. Masse, J. L. Knight, T. Steinbrecher, T. Beuming, W. Damm, E. Harder, W. Sherman, M. Brewer, R. Wester, M. Murcko, L. Frye, R. Farid, T. Lin, D. L. Mobley, W. L. Jorgensen, B. J. Berne, R. A. Friesner, R. Abel, Accurate and reliable prediction of relative ligand binding potency in prospective drug discovery by way of a modern free-energy calculation protocol and force field, Journal of the American Chemical Society, 137 (2015) 2695-2703.

[86] ADMET Predictor 8.5. http://www.simulations-plus.com/software/admetpredictor/(last accessed May, 2018).

[87] G. M. Sastry, M. Adzhigirey, T. Day, R. Annabhimoju, W. Sherman, Protein and ligand preparation: parameters, protocols, and influence on virtual screening enrichments, Journal of computer-aided molecular design, 27 (2013) 221-234.

[88] Schrödinger Release 2018-1: Schrödinger Suite 2018-1 Protein Preparation Wizard; Epik, Schrödinger, LLC, New York, N. Y., 2016; Impact, Schrödinger, LLC, New York, N. Y., 2016; Prime, Schrödinger, LLC, New York, N. Y., 2018.

We claim:

1. A method of cancer treatment, the method comprising administering a compound having the structure

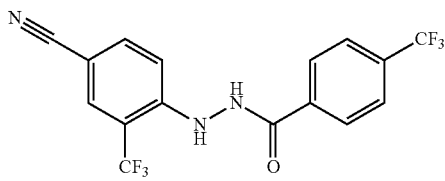 [SMILES: N#Cc1ccc(NNC(=O)c2ccc(C(F)(F)F)cc2)c(C(F)(F)F)c1]

to a patient in need thereof,
wherein the cancer is selected from one or more of the following: prostate cancer; breast cancer; colon cancer; cervical cancer; small-cell lung carcinoma; neuroblastomas; osteosarcoma; glioblastoma; melanoma; and myeloid leukaemia.

2. The method of claim 1, wherein the cancer is selected from prostate cancer, breast cancer, colon cancer, cervical cancer, and small-cell lung carcinoma.

3. The method of claim 1, wherein the cancer is prostate cancer.

4. The method of claim 1, wherein the cancer is breast cancer.

5. The method of claim 1, wherein the cancer is colon cancer.

6. The method of claim 1, wherein the cancer is cervical cancer.

7. The method of claim 1, wherein the cancer is small-cell lung carcinoma.

8. The method of claim 1, wherein the cancer is a neuroblastoma.

9. The method of claim 1, wherein the cancer is an osteosarcoma.

10. The method of claim 1, wherein the cancer is a glioblastoma.

11. The method of claim 1, wherein the cancer is a melanoma.

12. The method of claim 1, wherein the cancer is a myeloid leukaemia.

* * * * *

UNITED STATES PATENT AND TRADEMARK OFFICE
CERTIFICATE OF CORRECTION

PATENT NO. : 12,017,975 B2
APPLICATION NO. : 17/966227
DATED : June 25, 2024
INVENTOR(S) : Artem Tcherkassov et al.

It is certified that error appears in the above-identified patent and that said Letters Patent is hereby corrected as shown below:

In the Specification

Column 27,
Line 25, "$E^{6\ may\ be\ H,\ CH}{}_{3}$," should read --$E^6$ may be H, $CH_3$,--

Column 47,
Line 47, "Myc-negative 14015.19 cells" should read --Myc-negative HO15.19 cells--

Column 54,
Line 47, "knockout 11015.19 cell" should read --knockout HO15.19 cell--

Column 54,
Line 48, "proliferation of the 11015.19 cell" should read --proliferation of the HO15.19 cell--

Signed and Sealed this
Eighth Day of October, 2024

Katherine Kelly Vidal
*Director of the United States Patent and Trademark Office*